(12) United States Patent
Chu et al.

(10) Patent No.: US 9,752,925 B2
(45) Date of Patent: Sep. 5, 2017

(54) OPTICAL SENSOR

(71) Applicant: Taiwan Biophotonic Corporation, Zhubei (TW)

(72) Inventors: Chang-Sheng Chu, Zhubei (TW); Yu-Tang Li, Zhubei (TW); Yeh-Wen Lee, Zhubei (TW); Chih-Hsun Fan, Zhubei (TW); Lung-Pin Chung, Zhubei (TW); Jyh-Chern Chen, Zhubei (TW); Shuang-Chao Chung, Zhubei (TW)

(73) Assignee: Taiwan Biophotonic Corporation, Hsinchu (TW)

( * ) Notice: Subject to any disclaimer, the term of this patent is extended or adjusted under 35 U.S.C. 154(b) by 0 days.

(21) Appl. No.: 14/997,261

(22) Filed: Jan. 15, 2016

(65) Prior Publication Data

US 2016/0238443 A1 Aug. 18, 2016

Related U.S. Application Data

(60) Provisional application No. 62/115,648, filed on Feb. 13, 2015.

(51) Int. Cl.
*G01J 1/42* (2006.01)
*G01J 1/04* (2006.01)
(Continued)

(52) U.S. Cl.
CPC .......... *G01J 1/0459* (2013.01); *A61B 5/14552* (2013.01); *A61B 5/681* (2013.01); *G01J 1/0271* (2013.01); *G01J 1/0437* (2013.01); *G01J 1/08* (2013.01); *G01J 1/4228* (2013.01); *G01J 1/44* (2013.01); *H01L 31/0203* (2013.01); *H01L 31/0232* (2013.01); *H01L 31/02325* (2013.01);
(Continued)

(58) Field of Classification Search
CPC .......... G01J 1/0271; G01J 1/42; G01J 1/4228; G01J 1/0459; H01L 33/52; H01L 33/54; H01L 33/58; H01L 31/0203; H01L 31/125
See application file for complete search history.

(56) References Cited

U.S. PATENT DOCUMENTS

| 5,103,085 A | * | 4/1992 | Zimmerman | G01S 17/06 250/214 B |
| 5,317,149 A | * | 5/1994 | Uebbing | G01D 5/34715 250/216 |

(Continued)

FOREIGN PATENT DOCUMENTS

| JP | 9-148620 | 6/1997 |
| JP | 11-177125 | 7/1999 |

(Continued)

*Primary Examiner* — John Lee
(74) *Attorney, Agent, or Firm* — Steven Reiss

(57) ABSTRACT

The present disclosure relates to an optical sensor module, an optical sensing accessory, and an optical sensing device. An optical sensor module comprises a light source, a photodetector, and a substrate. The light source is configured to convert electric power into radiant energy and emit light to an object surface. The photodetector is configured to receive the light from an object surface and convert radiant energy into electrical current or voltage. An optical sensing accessory and an optical sensing device comprise the optical sensor module and other electronic modules to have further applications.

19 Claims, 62 Drawing Sheets

(51) Int. Cl.

| | |
|---|---|
| *G01J 1/44* | (2006.01) |
| *A61B 5/1455* | (2006.01) |
| *A61B 5/00* | (2006.01) |
| *H01L 31/0203* | (2014.01) |
| *H01L 31/0232* | (2014.01) |
| *H01L 31/173* | (2006.01) |
| *H04B 10/071* | (2013.01) |
| *G01J 1/02* | (2006.01) |
| *G01J 1/08* | (2006.01) |
| *H01L 31/12* | (2006.01) |
| *H01L 33/54* | (2010.01) |
| *H01L 33/58* | (2010.01) |

(52) U.S. Cl.
CPC ...... *H01L 31/02327* (2013.01); *H01L 31/125* (2013.01); *H01L 31/173* (2013.01); *H01L 33/54* (2013.01); *H01L 33/58* (2013.01); *H04B 10/071* (2013.01); *A61B 2560/0443* (2013.01); *A61B 2562/0233* (2013.01); *A61B 2562/164* (2013.01); *A61B 2562/227* (2013.01)

(56) References Cited

U.S. PATENT DOCUMENTS

| | | | | |
|---|---|---|---|---|
| 7,317,183 B2 * | 1/2008 | Wong | G01D 5/34707 | 250/231.13 |
| 7,385,178 B2 * | 6/2008 | Chin | G01D 5/34715 | 250/231.13 |
| 7,486,386 B1 * | 2/2009 | Holcombe | G01C 3/08 | 356/4.01 |
| 7,795,576 B2 * | 9/2010 | Chin | G01D 5/34715 | 250/231.13 |
| 7,907,061 B2 * | 3/2011 | Lin | G06F 1/3203 | 340/686.6 |
| 8,193,483 B2 * | 6/2012 | Chin | G01D 5/34715 | 250/231.13 |
| 8,362,496 B1 * | 1/2013 | Tu | H01L 25/167 | 257/80 |
| 8,400,687 B2 * | 3/2013 | Okawa | G07D 7/121 | 194/207 |
| 8,558,161 B2 * | 10/2013 | Ong | G02B 3/02 | 250/216 |
| 8,649,069 B2 * | 2/2014 | Okawa | G07D 7/121 | 194/207 |
| 8,841,597 B2 * | 9/2014 | Costello | G01D 11/245 | 250/221 |
| 8,946,620 B2 * | 2/2015 | Loong | G01S 17/026 | 250/221 |
| 8,946,747 B2 * | 2/2015 | Reiherzer | H01L 33/505 | 257/100 |
| 8,957,580 B2 * | 2/2015 | Reiherzer | F21K 9/56 | 313/498 |
| 9,018,663 B2 * | 4/2015 | Tasaki | H01L 33/58 | 257/98 |
| 9,088,282 B2 * | 7/2015 | Holenarsipur | H03K 17/955 | |
| 9,098,124 B2 * | 8/2015 | Holenarsipur | G06F 3/03 | |
| 9,275,974 B2 * | 3/2016 | Kaschner | H01L 25/042 | |
| 9,291,495 B2 * | 3/2016 | Land | G01S 17/026 | |
| 2002/0185651 A1 | 12/2002 | Sommers | | |
| 2004/0236227 A1 | 11/2004 | Gueissaz | | |
| 2005/0135724 A1 * | 6/2005 | Helvajian | B64G 1/10 | 385/14 |
| 2007/0003289 A1 * | 1/2007 | Tan | H04B 10/1127 | 398/164 |
| 2007/0090282 A1 * | 4/2007 | Chin | G01D 5/34715 | 250/231.13 |
| 2008/0208009 A1 | 8/2008 | Shklarski | | |
| 2008/0292360 A1 * | 11/2008 | Hirai | G01N 21/55 | 399/220 |
| 2008/0296589 A1 * | 12/2008 | Speier | H01L 33/642 | 257/82 |
| 2009/0080217 A1 * | 3/2009 | Schubert | G02B 27/286 | 362/612 |
| 2009/0295265 A1 * | 12/2009 | Tabuchi | H01L 33/56 | 313/112 |
| 2010/0230693 A1 * | 9/2010 | Tran | H01L 33/483 | 257/98 |
| 2011/0043871 A1 * | 2/2011 | Okawa | G07D 7/121 | 358/474 |
| 2011/0121181 A1 * | 5/2011 | Costello | G01S 7/4813 | 250/338.1 |
| 2012/0037793 A1 * | 2/2012 | Ong | G02B 3/02 | 250/216 |
| 2012/0160994 A1 * | 6/2012 | Costello | G01D 11/245 | 250/221 |
| 2012/0165759 A1 * | 6/2012 | Rogers | A61B 5/6867 | 604/264 |
| 2012/0176599 A1 * | 7/2012 | Leung | G01N 21/31 | 356/39 |
| 2012/0319573 A1 * | 12/2012 | Shi | H01L 33/507 | 313/512 |
| 2013/0037705 A1 * | 2/2013 | Soo | G01D 5/34715 | 250/231.13 |
| 2013/0207141 A1 * | 8/2013 | Reiherzer | H01L 33/505 | 257/98 |
| 2014/0051955 A1 | 2/2014 | Tiao et al. | | |
| 2014/0103199 A1 * | 4/2014 | Loong | G01S 17/026 | 250/214.1 |
| 2014/0124967 A1 * | 5/2014 | Ozaki | B29D 11/0074 | 264/2.7 |
| 2014/0132578 A1 * | 5/2014 | Zheng | G09G 5/10 | 345/207 |
| 2014/0191110 A1 * | 7/2014 | Holenarsipur | G06F 3/03 | 250/206 |
| 2014/0213323 A1 * | 7/2014 | Holenarsipur | H03K 17/955 | 455/566 |
| 2014/0231625 A1 * | 8/2014 | Chang | G01J 1/4204 | 250/208.1 |
| 2014/0267202 A1 * | 9/2014 | Zheng | G01J 1/4204 | 345/207 |
| 2014/0299896 A1 * | 10/2014 | Xu | H01L 33/54 | 257/88 |
| 2014/0305900 A1 * | 10/2014 | Rogers | H05K 13/0023 | 216/13 |
| 2014/0371601 A1 | 12/2014 | Fei | | |
| 2015/0018647 A1 | 1/2015 | Mandel et al. | | |
| 2015/0048407 A1 * | 2/2015 | Peil | F21K 9/00 | 257/98 |
| 2015/0249734 A1 * | 9/2015 | Rudmann | G01S 17/026 | 455/556.1 |
| 2016/0039974 A1 * | 2/2016 | Sun | C08G 69/32 | 264/1.1 |
| 2016/0054175 A1 * | 2/2016 | Jia | G01J 1/4204 | 250/216 |
| 2016/0056351 A1 * | 2/2016 | Yang | H01L 33/60 | 257/98 |
| 2016/0091364 A1 * | 3/2016 | Tu | G01J 1/42 | 250/216 |
| 2016/0238443 A1 * | 8/2016 | Chu | A61B 5/14552 | |

FOREIGN PATENT DOCUMENTS

| | | |
|---|---|---|
| JP | P2000-174350 | 6/2000 |
| JP | P2002-134793 | 5/2002 |
| JP | 2006-102159 | 4/2006 |
| JP | 2010-034189 | 2/2010 |
| JP | 2010-147040 | 7/2010 |
| JP | 2012-114474 | 6/2012 |
| JP | P2012-114474 | 6/2012 |
| TW | 201409014 | 3/2014 |
| TW | 201505133 | 2/2015 |
| WO | 2006/006158 | 1/2006 |
| WO | 2014/050612 | 4/2014 |

* cited by examiner

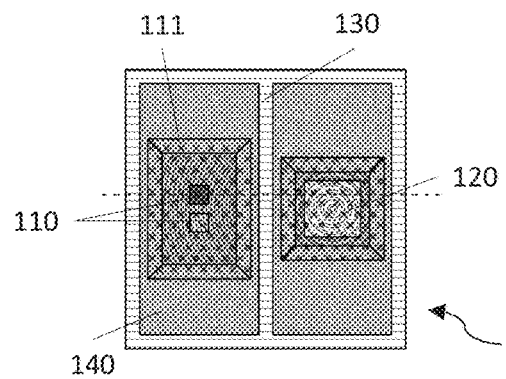
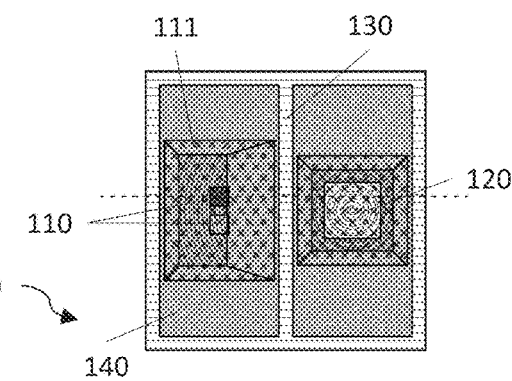
FIG. 2A  FIG. 3A
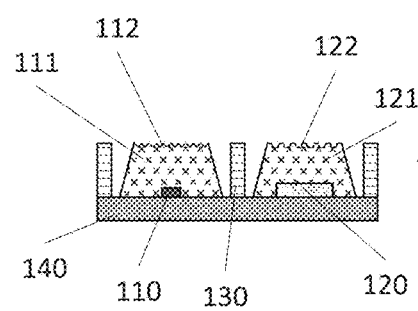
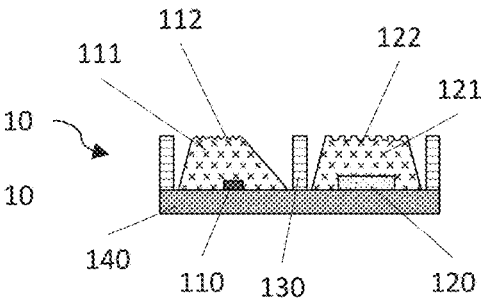
FIG. 2B  FIG. 3B
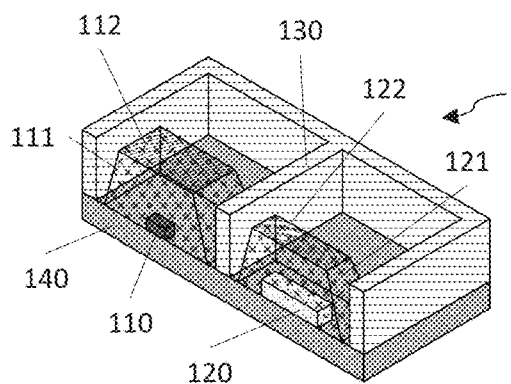
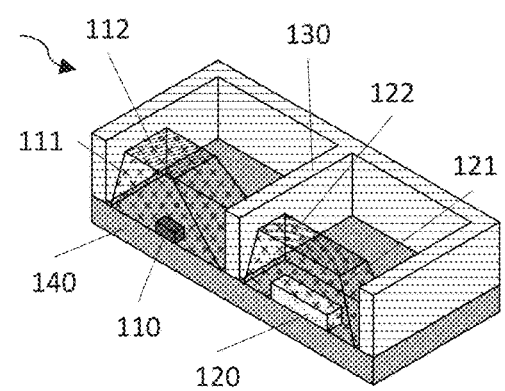
FIG. 2C  FIG. 3C

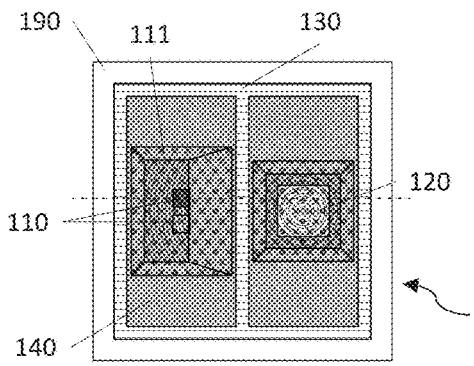
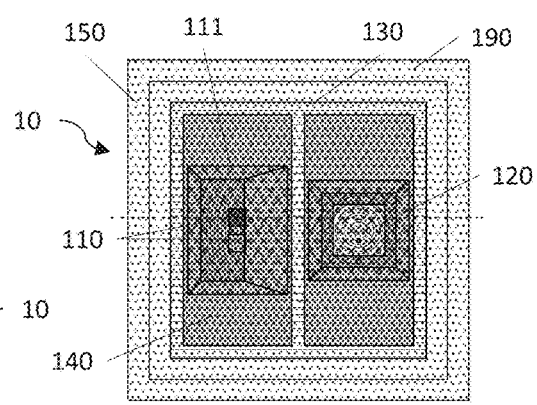
FIG. 6A    FIG. 7A
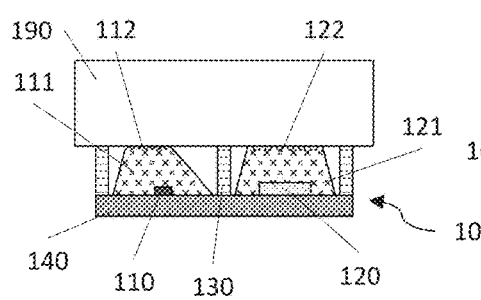
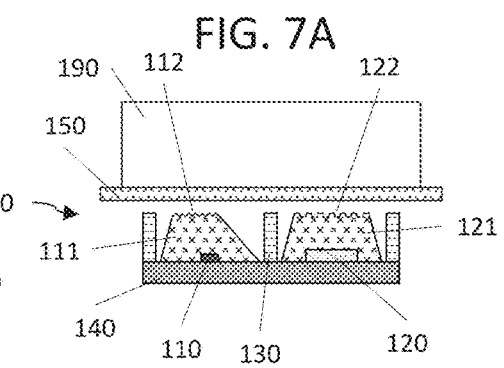
FIG. 6B    FIG. 7B
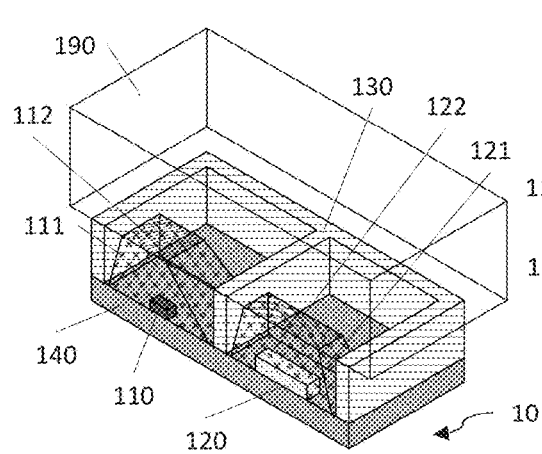
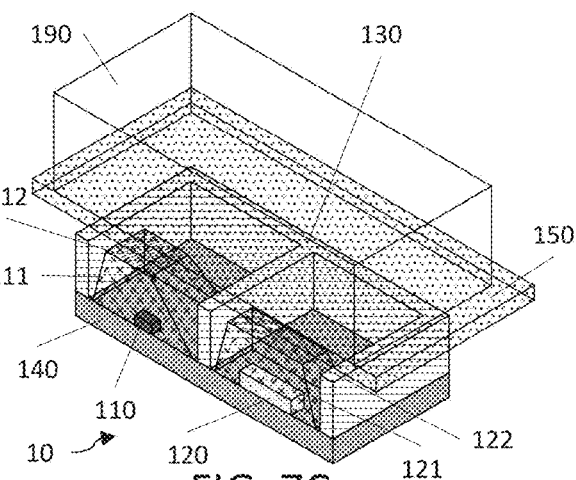
FIG. 6C    FIG. 7C

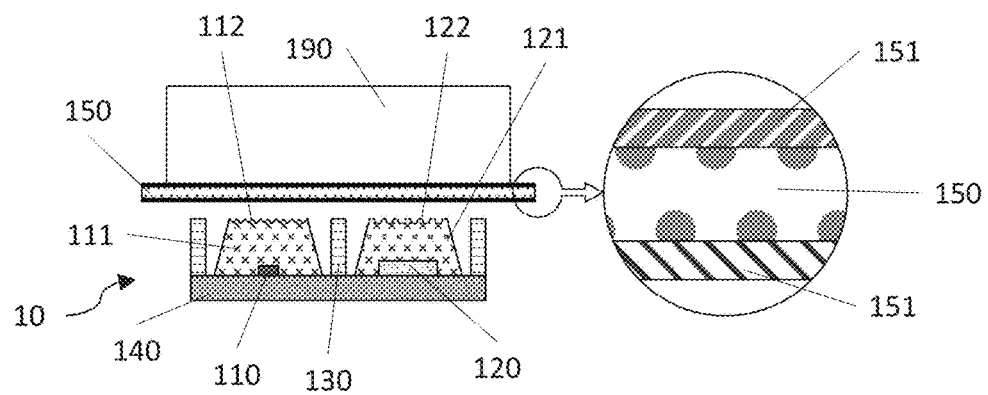
FIG. 8A  FIG. 8B
FIG. 9A
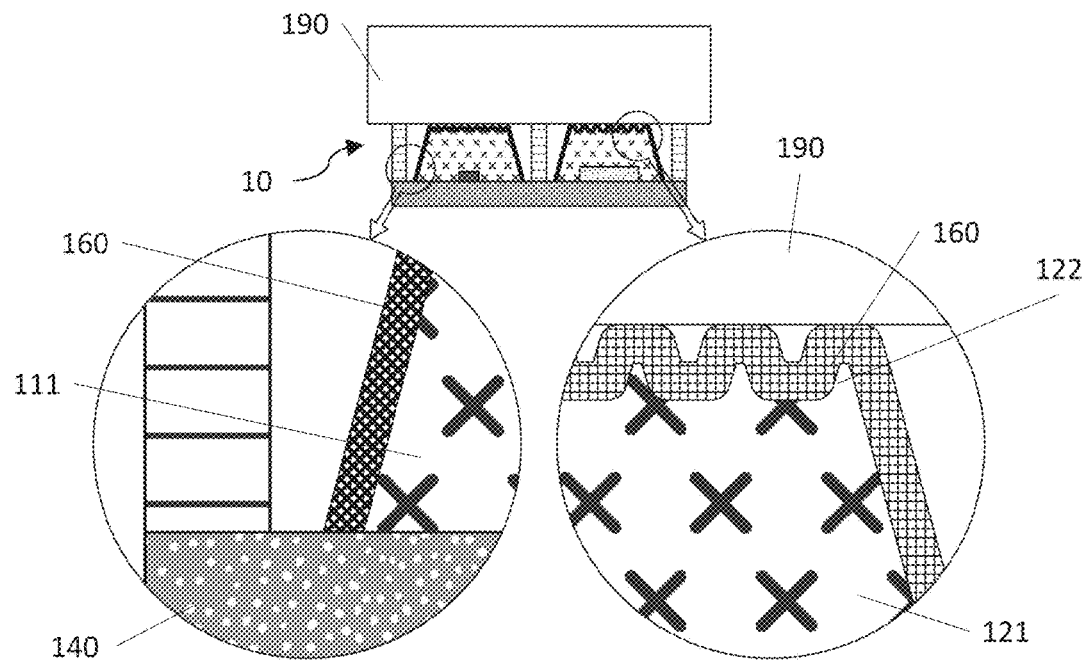
FIG. 9B  FIG. 9C

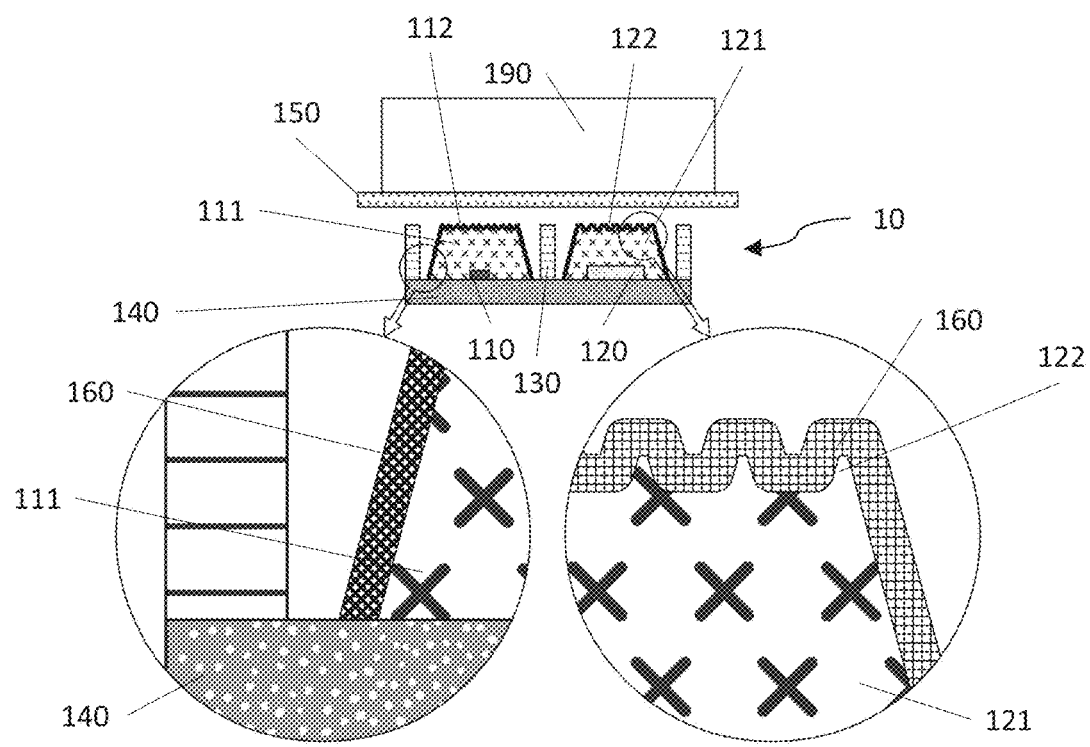

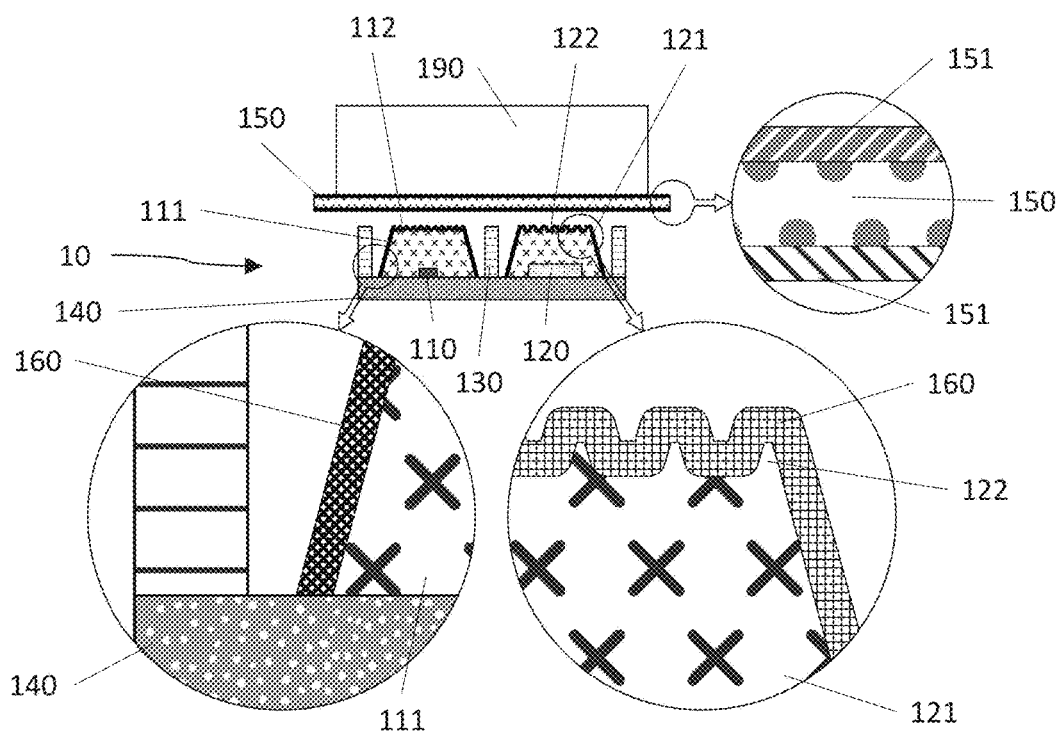

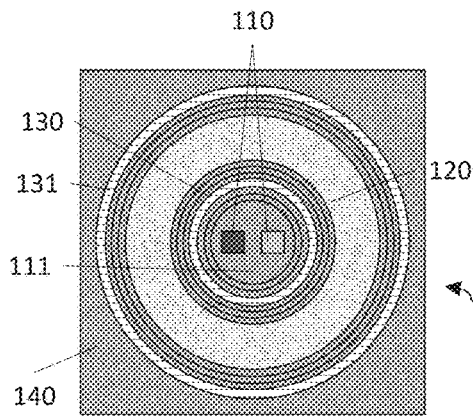
FIG. 12A
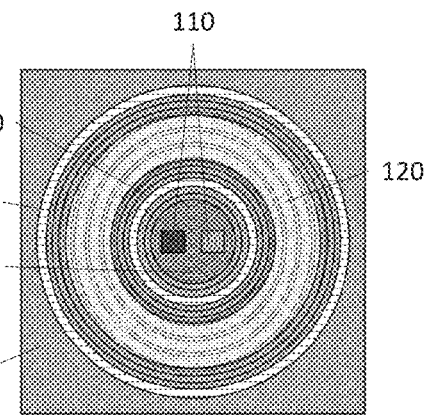
FIG. 13A
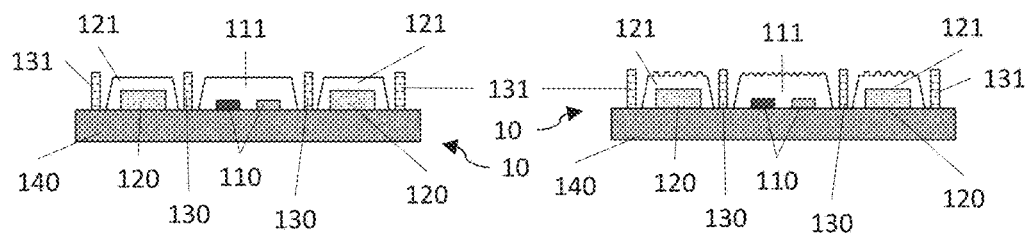
FIG. 12B
FIG. 13B
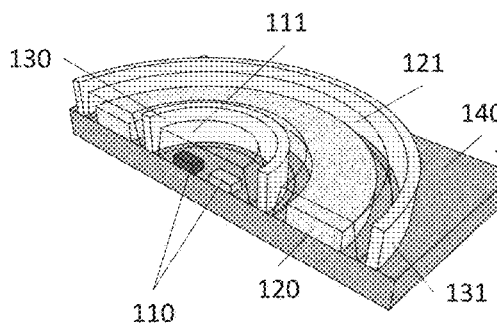
FIG. 12C
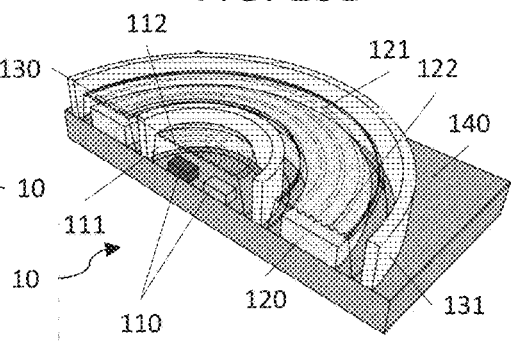
FIG. 13C

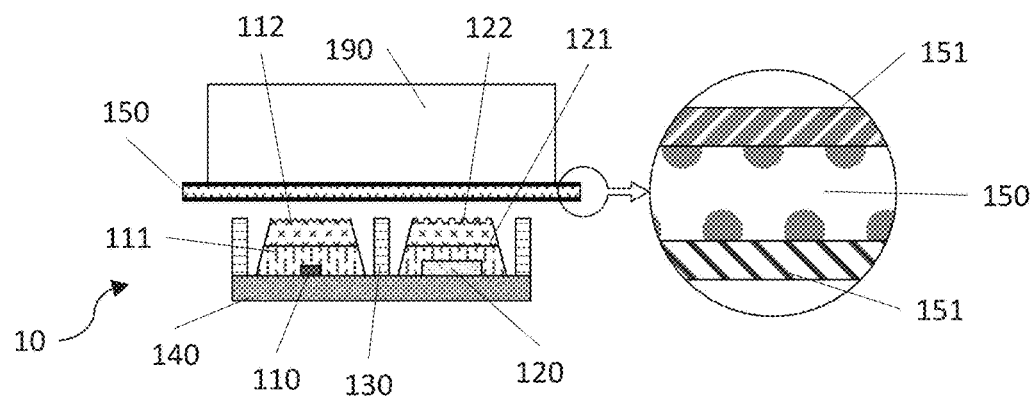
FIG. 39A  FIG. 39B
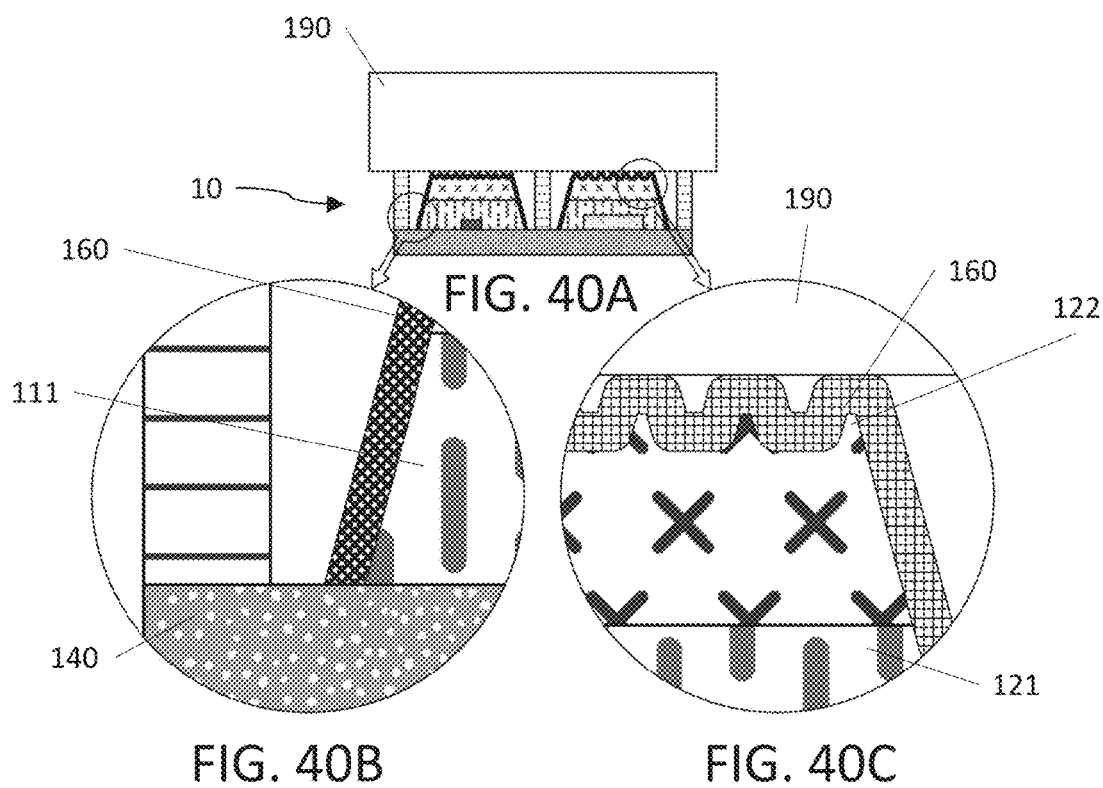
FIG. 40A
FIG. 40B  FIG. 40C

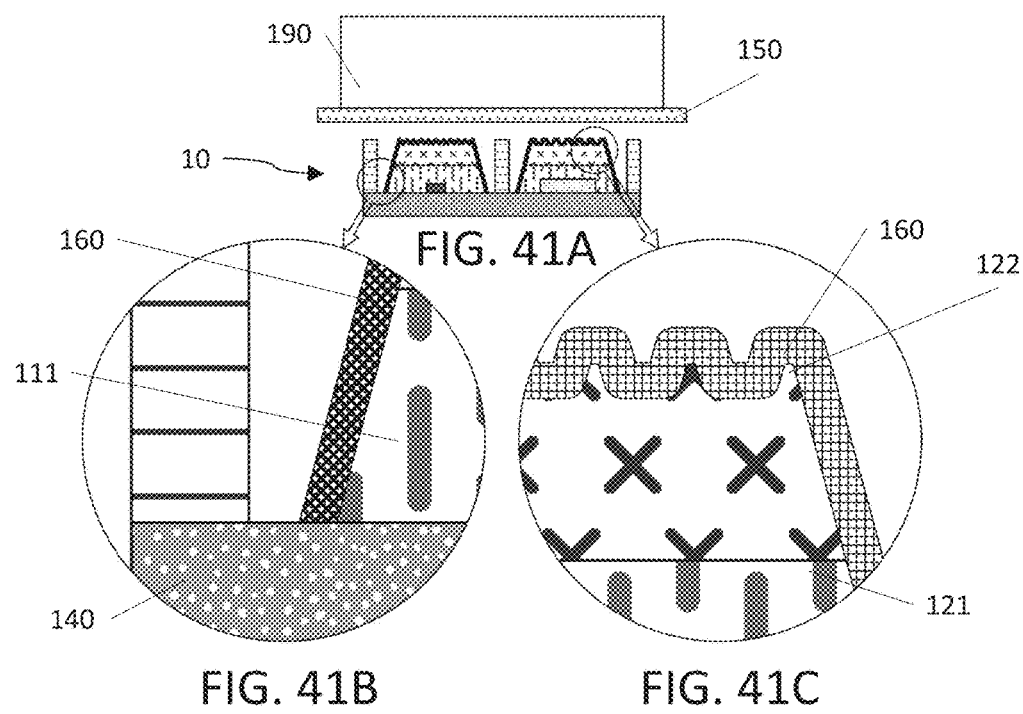

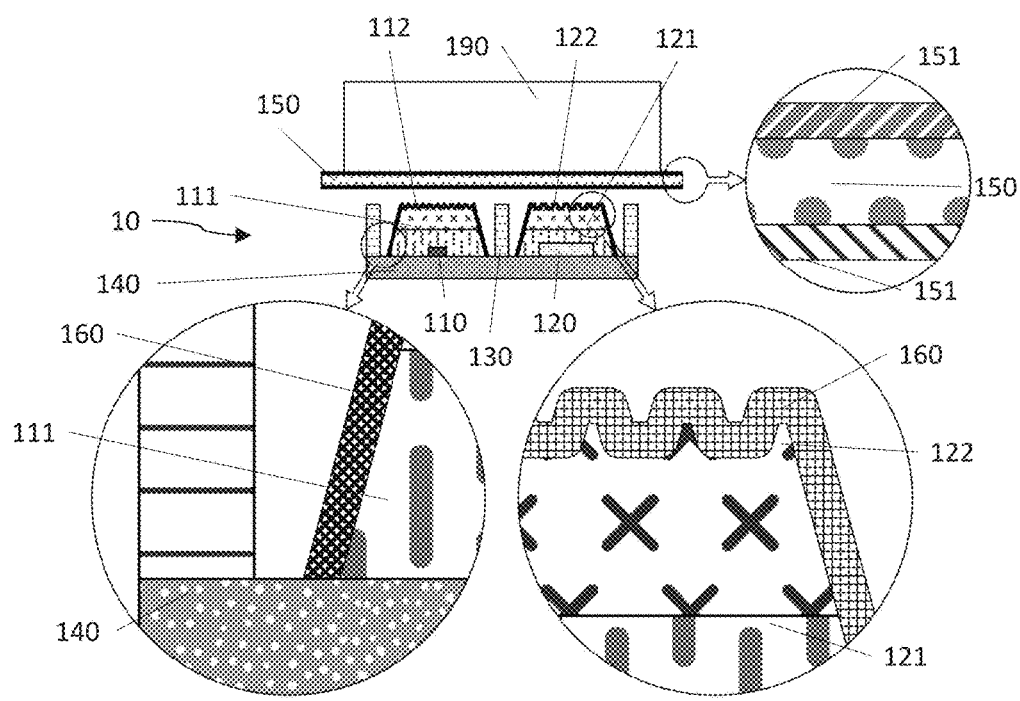

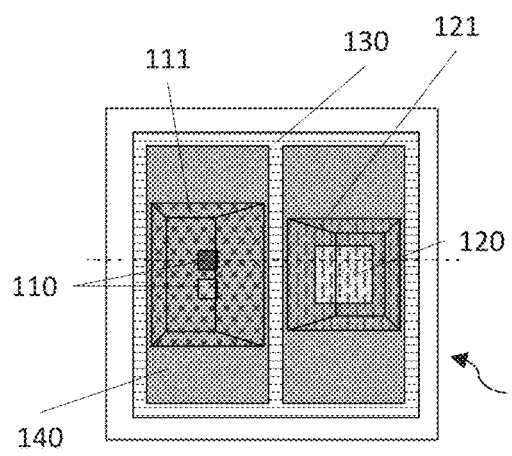
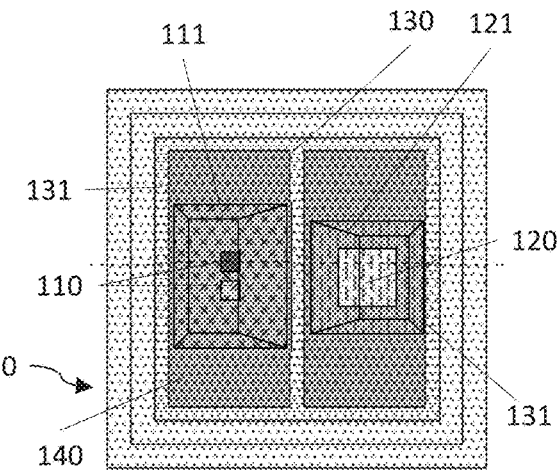
FIG. 47A  FIG. 48A
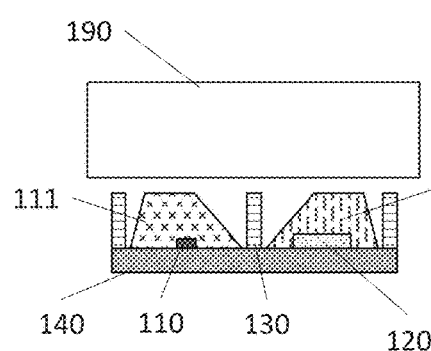
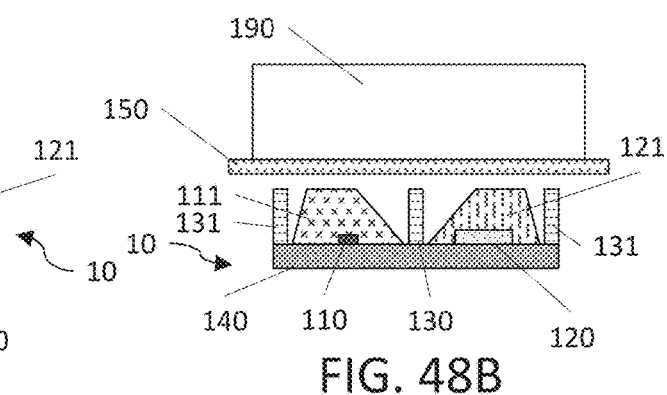
FIG. 47B  FIG. 48B

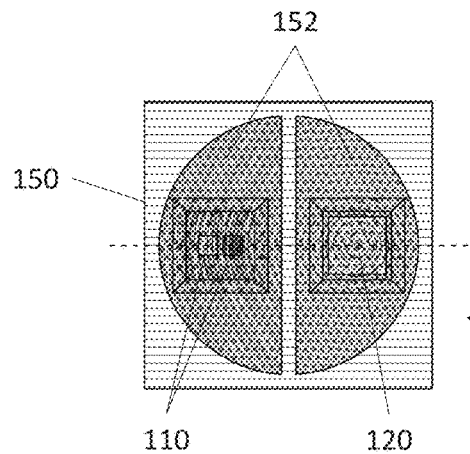
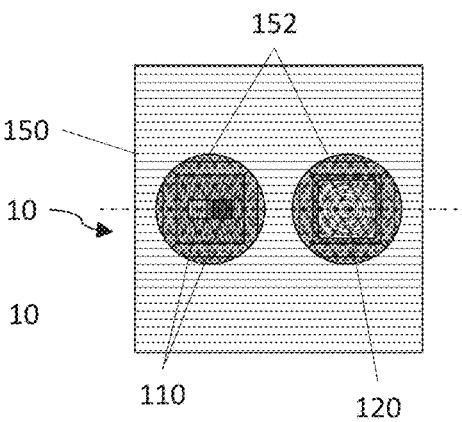
FIG. 51A  FIG. 52A
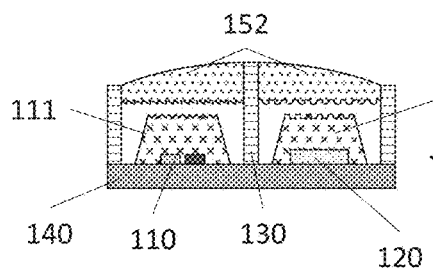
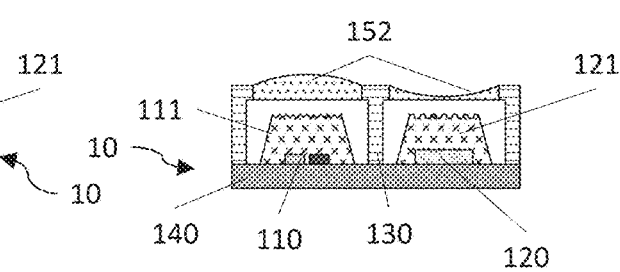
FIG. 51B  FIG. 52B
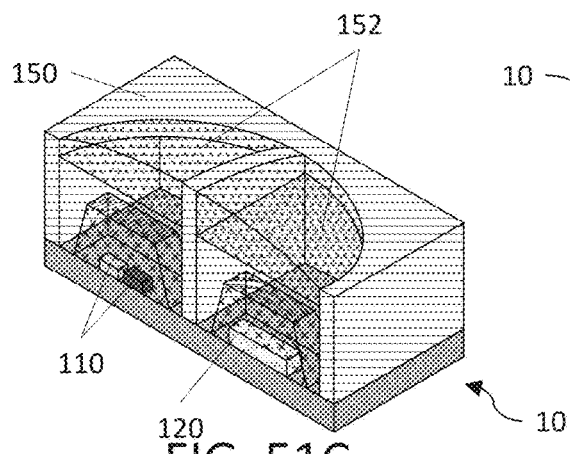
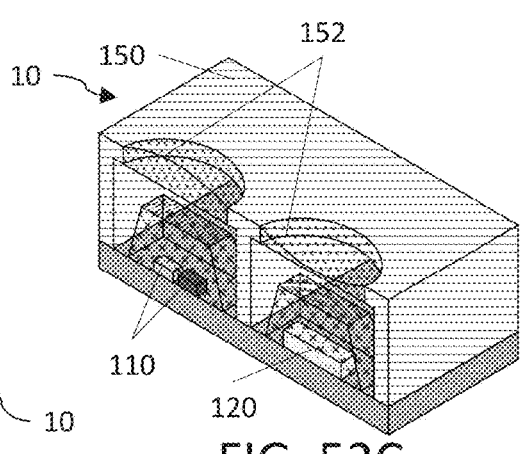
FIG. 51C  FIG. 52C

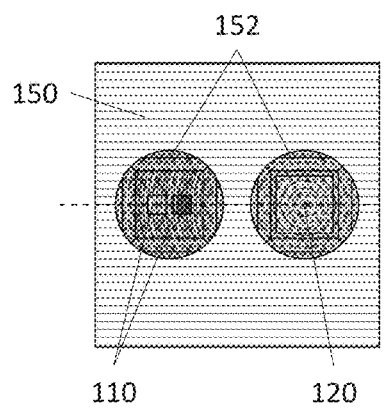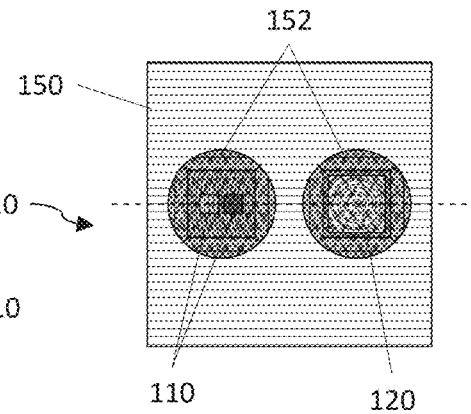
FIG. 53A  FIG. 54A
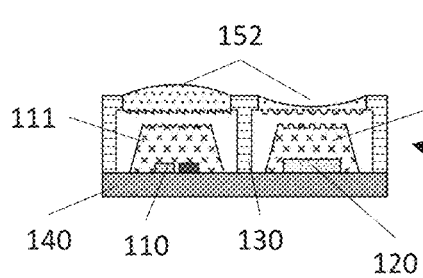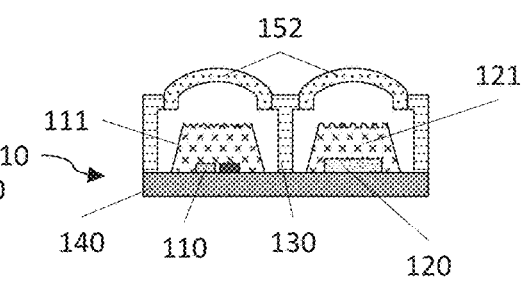
FIG. 53B  FIG. 54B
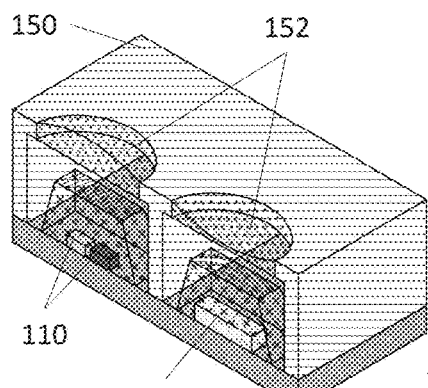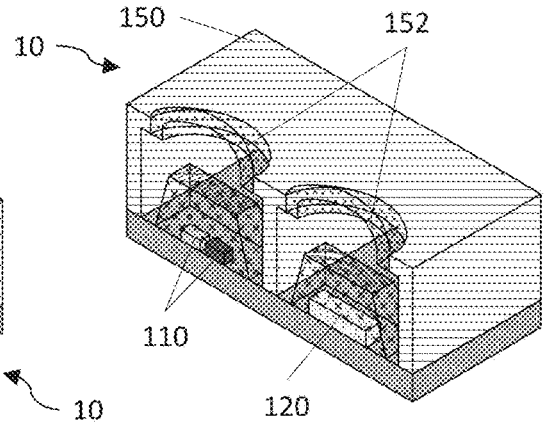
FIG. 53C  FIG. 54C

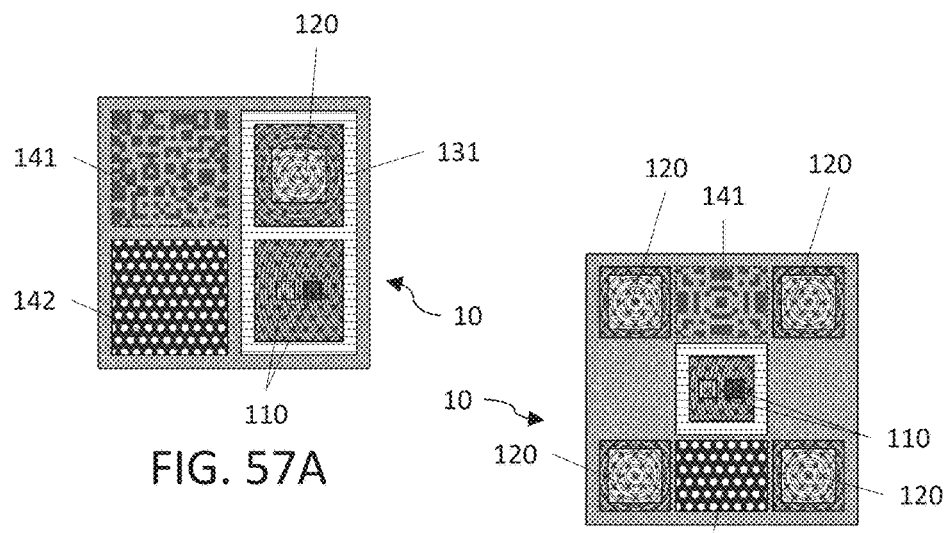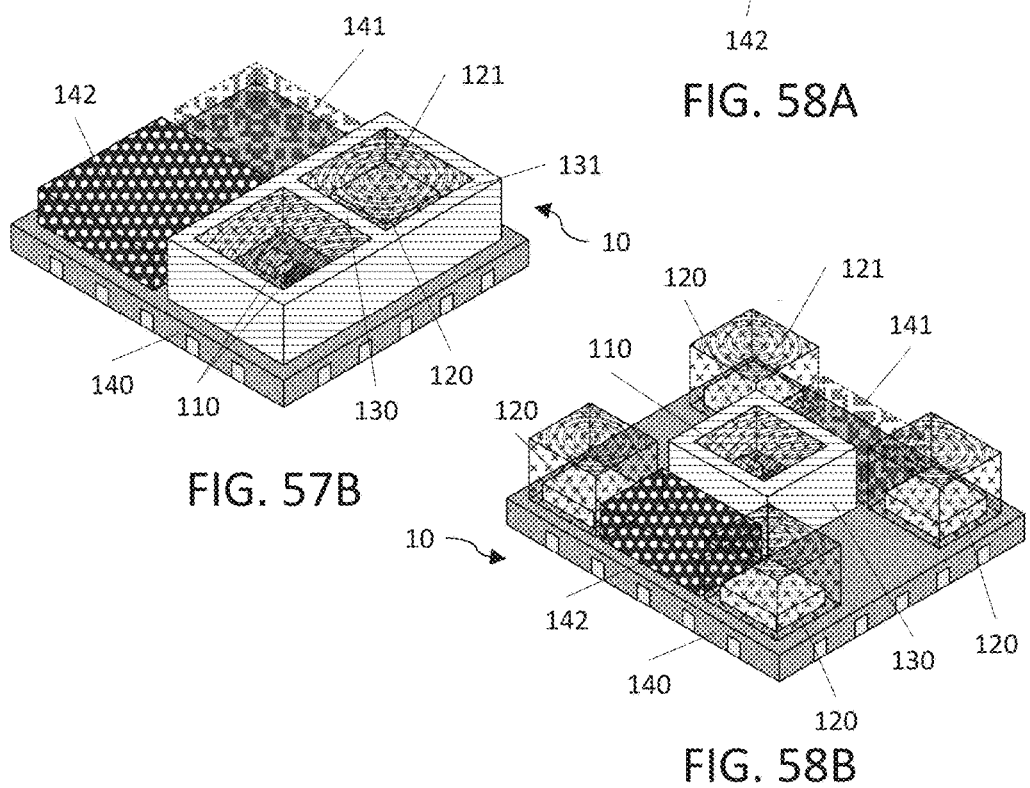

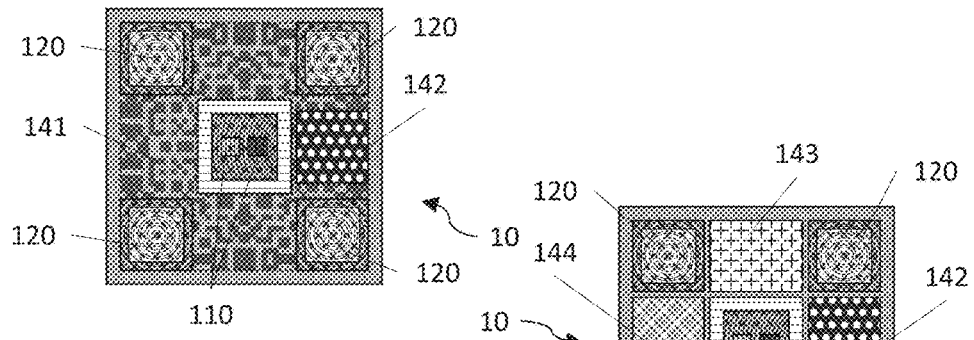
FIG. 59A
FIG. 60A
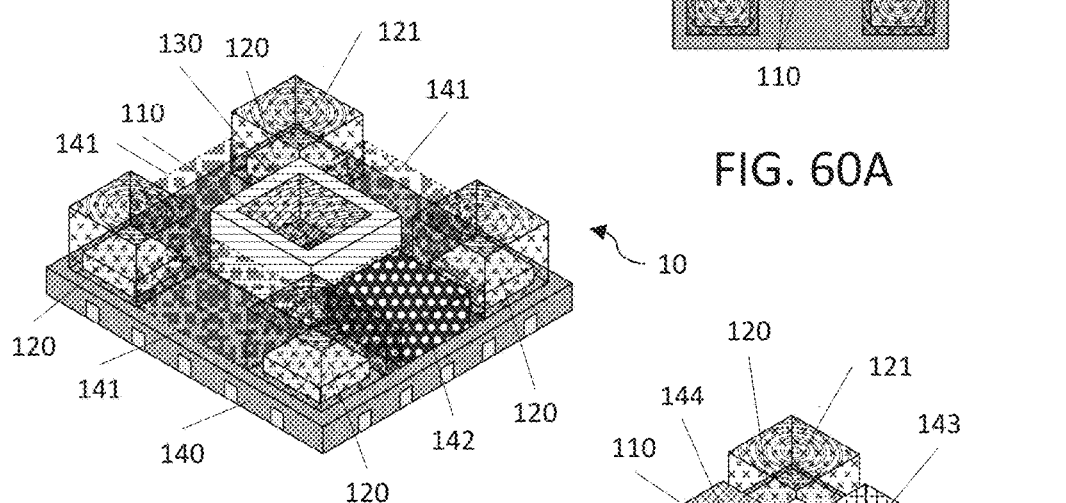
FIG. 59B
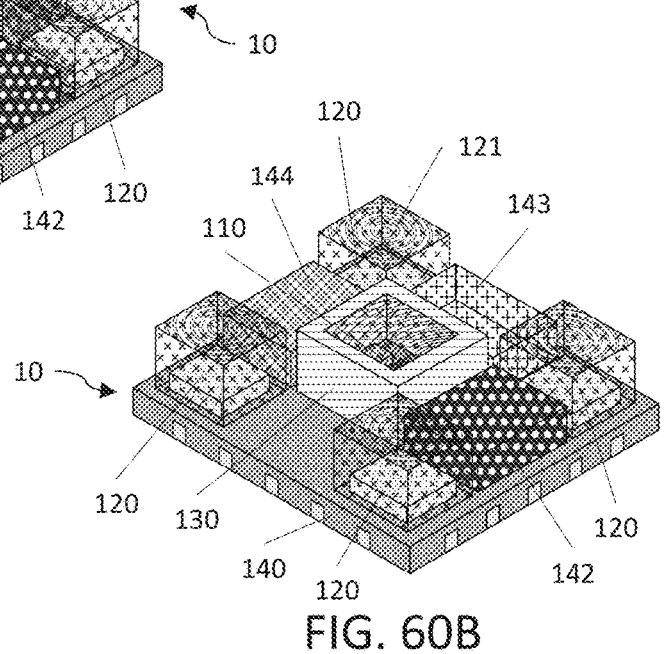
FIG. 60B

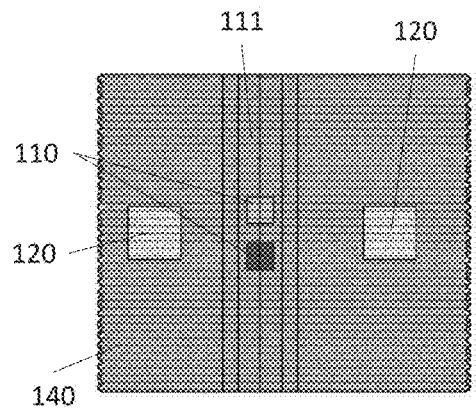
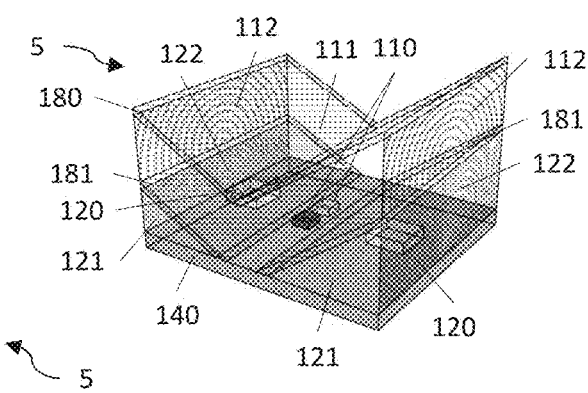
FIG. 63A
FIG. 63C
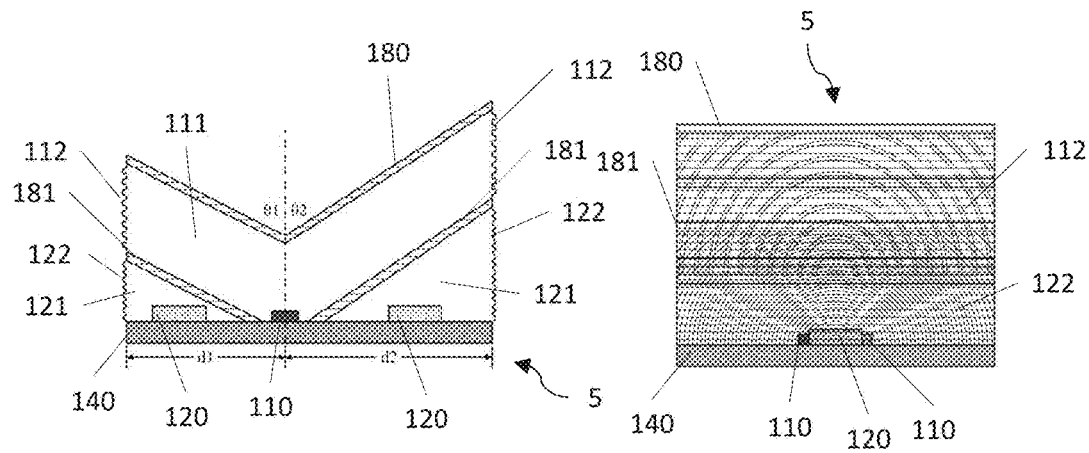
FIG. 63B
FIG. 63D

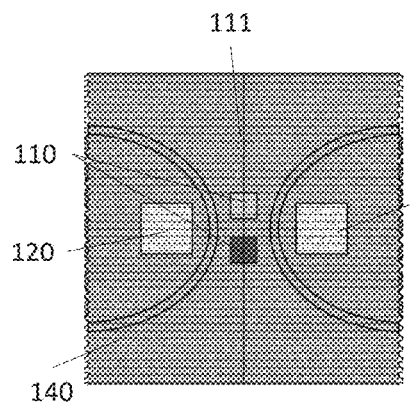
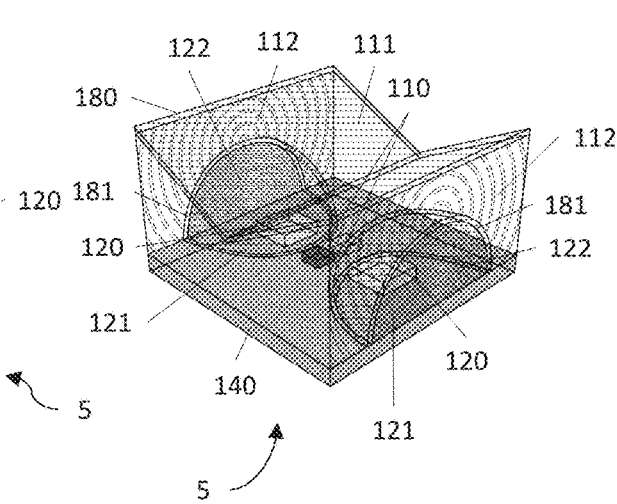
FIG. 65A
FIG. 65C
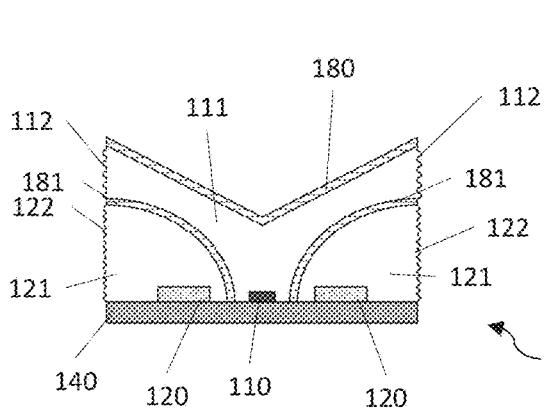
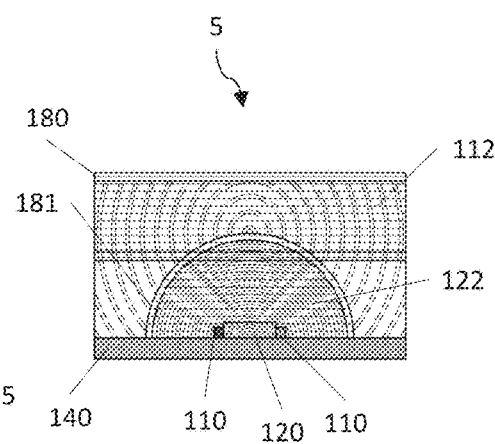
FIG. 65B
FIG. 65D

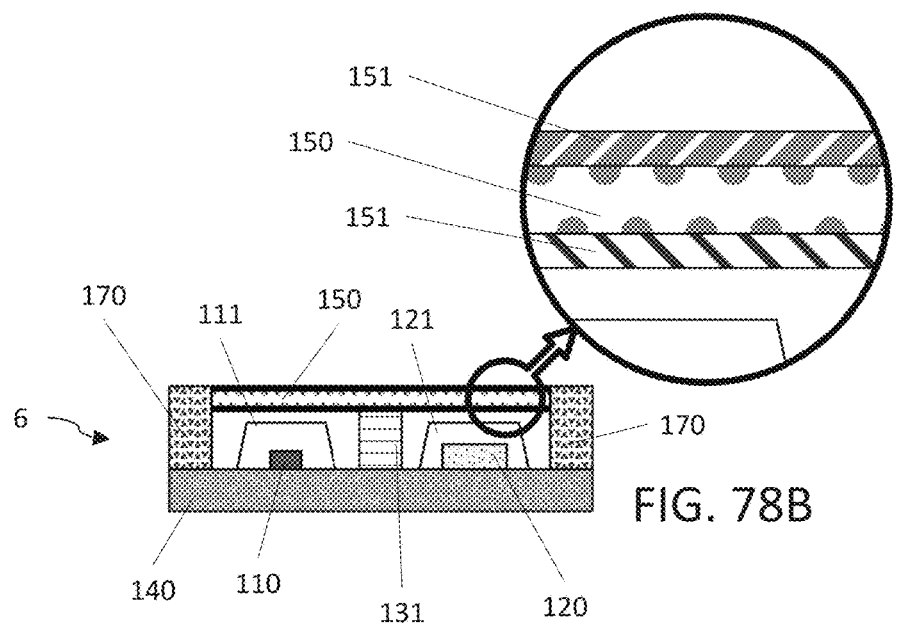
FIG. 78B
FIG. 78A
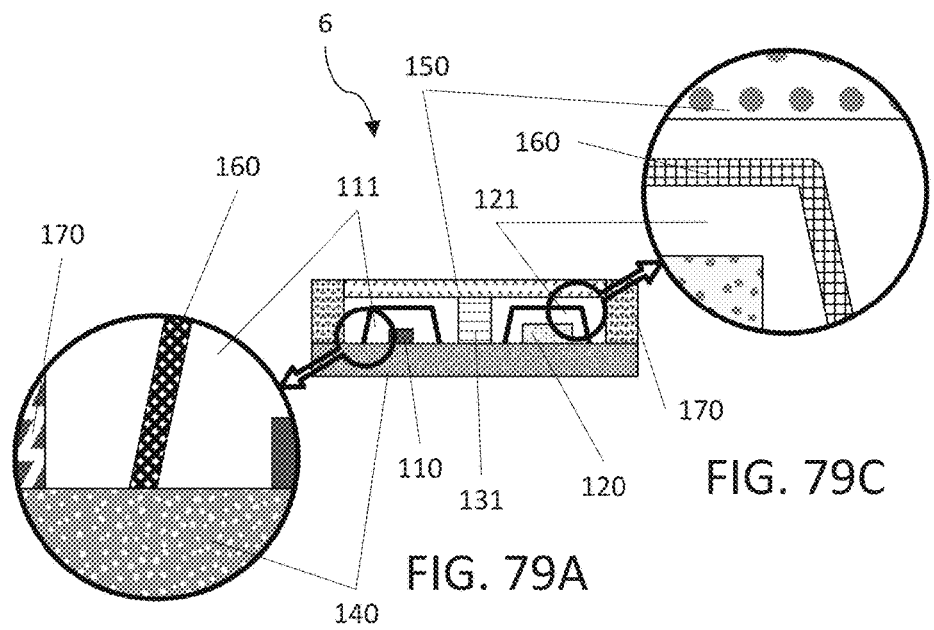
FIG. 79C
FIG. 79A
FIG. 79B

OPTICAL SENSOR

FIELD

The disclosure relates generally to optical sensors and associated applications to collect and manage the signals.

BACKGROUND

The reflective optical sensor module emits light and measures the amount of reflected light from an object. The optical sensor module converts electrical current into light, which is directed onto the surface of an object, and converts the reflected light into electrical signals. The incident light can then be reflected by the object, absorbed by the object, or scattered by the object. A portion of reflected and scattered light can reach a photodetector of the optical sensor module; the received reflected and scattered light produces a corresponding signal. The acquired optical signals may be computed as useful information, especially physiological information, such as the blood oxygen saturation level, which is based on the light absorption rate of particular wavelengths. Further physiological information may be derived from the acquired optical information at multiple parts of human body. People confront a problem with obtaining information simultaneously from multiple parts of human body or reproducibly at the exact same sites. Previous solution is either to measure multiple regions sequentially, or to combine several sensor devices for multi-site measurement. However, simply applying a sensing device or several independent sensing devices on multiple sites introduces additional temporal or spatial errors (for example, from phase differences, or inter-experimental variation).

BRIEF DESCRIPTION OF THE DRAWINGS

Implementations of the present technology will now be described, by way of example only, with reference to the attached figures.

FIG. 2A-2C are schematic diagrams of a top view, cross-sectional view, and oblique sectional view, respectively, of an optical sensor in accordance with an embodiment of the present disclosure.

FIG. 3A-3C are schematic diagrams of a top view, cross-sectional view, and oblique sectional view, respectively, of an optical sensor in accordance with an embodiment of the present disclosure.

FIG. 6A-6C are schematic diagrams of a top view, cross-sectional view, and oblique sectional view, respectively, of an optical sensor with an object surface in accordance with an embodiment of the present disclosure.

FIG. 7A-7C are schematic diagrams of an optical sensor module comprising a cover applied on an object surface.

FIG. 8A is a cross-sectional view of an optical sensor module comprising a cover applied on an object surface; FIG. 8B is a partial enlarged view of the double-sided thin film cover.

FIG. 9A is a cross-sectional view of the thin film coated encapsulants; FIG. 9B is a partial enlarged view of the first thin film coated encapsulant; FIG. 9C is a partial enlarged view of the second thin film coated encapsulant.

FIG. 10A is a cross-sectional view of the optical sensor module comprising a cover and the thin film coated encapsulants; FIG. 10B is a partial enlarged view of the first thin film coated encapsulant; FIG. 10C is a partial enlarged view of the second thin film coated encapsulant.

FIG. 11A is a cross-sectional view of the optical sensor module comprising a double-sided thin film cover and the thin film coated encapsulants; FIG. 11B is a partial enlarged view of the double-sided thin film cover, FIG. 11C is a partial enlarged view of the first thin film coated encapsulant, and FIG. 11D is a partial enlarged view of the second thin film coated encapsulant.

FIG. 12A-12C are schematic diagrams of a top view, cross-sectional view, and oblique sectional view, respectively, of an optical sensor module in accordance with one embodiment of the present disclosure.

FIG. 13A-13C are schematic diagrams of a top view, cross-sectional view, and oblique sectional view, respectively, of an optical sensor module in accordance with an embodiment of the present disclosure.

FIG. 39A is a cross-sectional view of the optical sensor module comprising a double-sided thin film cover and the thin film coated encapsulants applied on an object surface; FIG. 39B is a partial enlarged view of the double-sided thin film cover.

FIG. 40A is a cross-sectional view of the optical sensor module comprising the thin film coated encapsulants applied on an object surface; FIG. 40B is a partial enlarged view of the first thin film coated encapsulant; FIG. 40C is a partial enlarged view of the second thin film coated encapsulant.

FIG. 41A is a cross-sectional view of the optical sensor module comprising a double-sided thin film cover and the thin film coated encapsulants applied on an object surface; FIG. 41B is a partial enlarged view of the first thin film coated encapsulant; FIG. 41C is a partial enlarged view of the second thin film coated encapsulant.

FIG. 42A is a cross-sectional view of the optical sensor module comprising a double-sided thin film cover and the thin film coated encapsulants applied on an object surface; FIG. 42B is a partial enlarged view of the double-sided thin film cover; FIG. 42C is a partial enlarged view of the first thin film coated encapsulant; FIG. 42D is a partial enlarged view of the second thin film coated encapsulant.

FIG. 47A-47B are schematic diagrams of a top view and cross-sectional view of an optical sensor module applied to an object surface in accordance with an embodiment of the present disclosure.

FIG. 48A-48B are schematic diagrams of a top view and cross-sectional view of an optical sensor module comprising a cover applied to an object surface in accordance with an embodiment of the present disclosure.

FIG. 51A-51C are schematic diagrams of a top view, cross-sectional view, and oblique sectional view, respectively, of an optical sensor module comprising a cover in accordance with an embodiment of the present disclosure.

FIG. 52A-52C are schematic diagrams of a top view, cross-sectional view, and oblique sectional view, respectively, of an optical sensor module comprising a cover in accordance with an embodiment of the present disclosure.

FIG. 53A-53C are schematic diagrams of a top view, cross-sectional view, and oblique sectional view, respectively, of an optical sensor module comprising a cover in accordance with an embodiment of the present disclosure.

FIG. 54A-54C are schematic diagrams of a top view, cross-sectional view, and oblique sectional view, respectively, of an optical sensor module comprising a cover in accordance with an embodiment of the present disclosure.

FIG. 57A-57B are schematic diagrams of a top view and oblique view, respectively, of an optical sensor module comprising an analogue front end and a microcontroller in accordance with an embodiment of the present disclosure.

FIG. 58A-58B are schematic diagrams of a top view and oblique view, respectively, of an optical sensor module comprising an analogue front end and a microcontroller in accordance with an embodiment of the present disclosure.

FIG. 59A-59B are schematic diagrams of a top view and oblique view, respectively, of an optical sensor module comprising a plurality of analogue front end and a microcontroller in accordance with an embodiment of the present disclosure.

FIG. 60A-60B are schematic diagrams of a top view and oblique view, respectively, of an optical sensor module comprising an operational amplifier, a light source driver and a microcontroller in accordance with an embodiment of the present disclosure.

FIG. 63A-63C are schematic diagrams of a top view, cross-sectional view, and oblique sectional view, respectively, of an optical sensing module in accordance with an embodiment of the present disclosure. FIG. 63D is the side view of an optical sensor module from the side of contact surface.

FIG. 65A-65C are schematic diagrams of a top view, cross-sectional view, and oblique sectional view, respectively, of an optical sensing module in accordance with an embodiment of the present disclosure. FIG. 65D is the side view of an optical sensor module from the side of contact surface.

FIG. 78A is a cross-sectional view of the optical sensor module comprising a double-sided thin film cover; FIG. 78B is a partial enlarged view of the double-sided thin film cover.

FIG. 79A is a cross-sectional view of the optical sensor module comprising a cover and the thin film coated encapsulants; FIG. 79B is a partial enlarged view of the first thin film coated encapsulant; FIG. 79C is a partial enlarged view of the second thin film coated encapsulant.

FIG. 80A is an example of the housing for a handheld device. FIGS. 80B and 80 C is an example of the annular shape housing for a wearable device. FIG. 80D is an example of the patch shape housing for a wearable device.

DETAILED DESCRIPTION

Figure 1A:
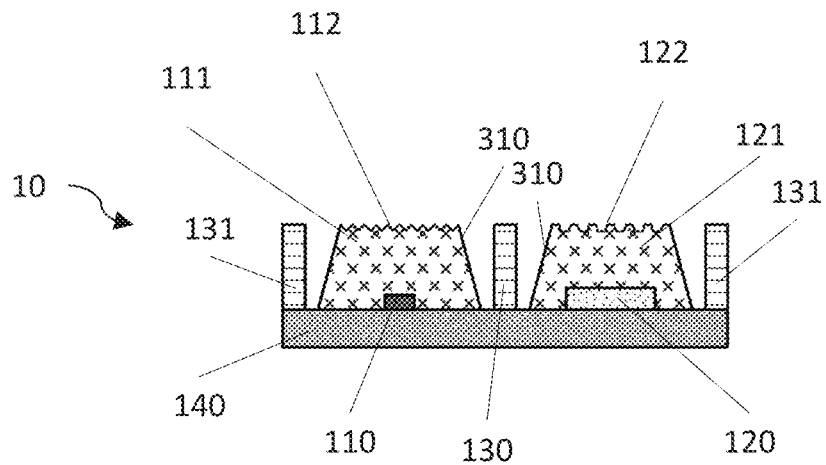
FIGS. 1A and 1B are schematic diagrams of a cross-sectional view of an optical sensor in accordance with a first and a second embodiments of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like.

Figure 1B:
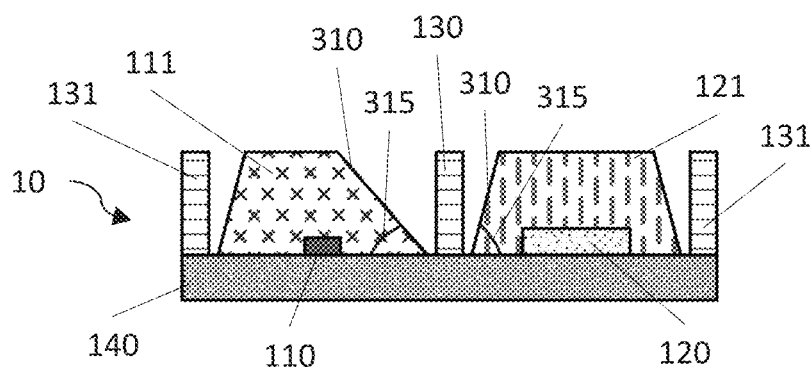

The reflective optical sensor module is manufactured to emit light and detect the reflected light from an object surface, and the received reflected light will be proportionally transduced into electrical signal, such as a voltage, a current or a combination thereof. As shown in FIGS. 1A and 1B, the optical sensor module 10 comprises a light source 110, a first encapsulant 111 over the light source 110, a photodetector 120, a second encapsulant 121 over the photodetector 120, and a partition 130. Each of the light source 110, the photodetector 120, the first encapsulant 111, the second encapsulant 121, and the partition 130 are mounted on a substrate 140. The optical sensor module 10 may be fabricated in a single compact package. It is also contemplated that the optical sensor module 10 may employ discrete light source 110 and photodetector 120 that are separately packaged and mounted to one or more printed circuit boards (also referred to as "PCB") depending on various design requirements. The exemplary embodiments of each component are described as below.

A substrate 140 is configured to have components installed thereon and provides mechanical or electrical connections between the components. Further, the substrate 140 provides mechanical support to the components of the optical sensor module 10 and interconnectivity between other external electronic components and the optical sensor module 10. In addition, the first encapsulant 111 and the second encapsulant 121 of the optical sensor module 10 are also formed on the substrate 140. In implementation, the substrate 140 may be printed circuit board (PCB), metal core PCB (MCPCB), ceramic PCB, or direct bonded copper substrate (DBC).

Optoelectronic transducers can convert the signals between optical signals and electrical signals. The light source 110, which converts electric power into radiant energy in a specific spectrum of wavelengths (for example, ultraviolet, visible, or infrared portions of the spectrum). The light source 110 may have electrical connections to a printed circuit embedded in the substrate to receive triggering signals and applied voltage from a microcontroller, a light source driver, or a gated power source. In implementation, the optical sensor module 10 may employ one or more light emitting diodes (LED), organic light emitting diodes (OLED), laser diodes (LD), or the like as light source 110. For example, the light source 110 of the optical sensor module 10 may comprise one or more LEDs, each configured to emit light in the specific spectrum of wavelengths. It is contemplated that the light sources 110 may further emit light in different spectrum of wavelengths synchronously or asynchronously depending on various applications.

The photodetector 120, which detects and converts radiant energy in the specific spectrum into electrical current or voltage, is mounted to the substrate 140. The photodetector should have a spectral response at least active in a part of corresponding wavelengths of the light source 110. The photodetector 120 may have electrical connections to a printed circuit embedded in the substrate to convey the photocurrent to a microcontroller, an operational amplifier, or an analogue front end. In implementation, the optical sensor module 10 may employ photodiode, phototransistor, photoresistor, photomultiplier, metal oxide semiconductor (MOS), or the like as photodetector 120. The photodetector 120 may detect the light in the specific spectrum of wavelengths emitted by the light source 110 or the light with a wavelength shift from the light emitted by the light source. Accordingly, the photodetector 120 converts the detected light into electrical signals. The photodetector 120 may also detect light in a spectrum of wavelengths different from the specific spectrum of wavelength of the light source 110. For example, the fluorescent light emitted from an object surface after receiving the light emitted from the light source 110 may be detected by a photodetector 120. Furthermore, the photodetector 120 may also detect the infrared light from an object surface, while the light source 110 does not emit infrared light in one example. The photodetector 120 may comprise a single or a plurality of photodiodes to extend the response spectrum or to separately measure different wavelengths of received light.

A partition 130 is mounted to the substrate 140 and is formed between the light source 110 and the photodetector 120 for blocking the stray light directly from the light source 110 to the photodetector 120. In addition, the partition 130 may be formed of opaque material, which reflects and/or absorbs light in a specific spectrum of wavelengths emitted by the light source 110. Furthermore, an optical sensor module may have packaging walls 131 to prevent the ambient noise. As shown in the FIGS. 1A and 1B, the packaging walls 131 of the optical sensor module 10 may be formed around the light source 110 and the photodetector 120. The packaging walls 131 may further provide mechanical support when a cover 150 is applied in an optical sensor module. In some examples, a part of the packaging wall 131 may be disposed between the light source and the photodetector, and replace the function of the partition. The packaging wall may define an area surrounding the light source, the partition, and the photodetector. The partition and the packaging wall may have similar or different material depending on the requirement of the capability of light blocking. Also, the partition and the packaging wall may be formed as a single entity or as multiple separate parts.

The encapsulants hermetically seal the optoelectronics for prolonging the durability of the optoelectronics, and improving light extraction efficiency by mediating the high refractive index difference between the optoelectronics and the environmental medium. The encapsulants should be, at least partially, transparent so that it can be an adequate medium of light propagation. In implementation, the material of the encapsulants may have lower refractive index than the optoelectronics have and higher than the environment, such as air, water, or gel. The material can be selected from silicone compound, or selected from clear polymers, which can include polydimethylsiloxane (PDMS), polycarbonate (PC), or poly(methyl methacrylate) (PMMA).

The present technology has the features on the construction and the configuration of an encapsulant 111 covering the light source 110 or an encapsulant 121 covering the photodetector 120. The encapsulants 111, 121 can be constructed using a single layer or more than one layer. When a single layer construction manufactured by one kind of material is implemented, the encapsulant may have one refractive index mediating the optoelectronics and the environment. The refractive index difference between an optoelectronic transducer with a great refractive index and the environment with low refractive index leads to poor light extraction or light receiving efficiency. An encapsulant generally has a refractive index between a great refractive index of an optoelectronic transducer and a low refractive index the environment, so that the light extraction or light receiving efficiency can be slightly improved.

The multilayer construction may be formed by multiple physical layers with different refractive indices or may be formed as a single entity with non-homogenous refractive index, such as a gradient refractive index. In one example, an encapsulant may be manufactured by stacking multiple layers with different refractive indices. In other example, an encapsulant with one material may be applied with an external electrical field during the manufacturing process, and resulting in the encapsulant with multiple refractive index layers while no physical interfaces presented in the encapsulant. In one example, refractive indices of each of the layers may decrease from proximal portion to distal portion when the encapsulant has a multilayer construction.

For ease of understanding, the illustrations of the encapsulants with multilayer construction, including physical layers or a single entity with non-homogenous refractive index, may be depicted with separate line and different hatchings. Without departing from the scope, the drawings are not limited to the encapsulants with multilayer construction in multiple physical layers. It has the advantage of reducing total internal reflection of emitting light by gradually mediating the high refractive index difference between light source 110 and the environmental medium the emitting surface, and, hence, improves the light extraction efficiency. As to the construction styles, presented as various kinds of stacks, are engineered for specific requirements.

The surface of an encapsulant may be formed as a specific configuration; especially in the case of multiple layer construction, the interface of any two layers may also be formed as a specific configuration. The specific configuration may be a microstructure or an optical directional component and the detail of the embodied configurations will be described below. An encapsulant may have modifications in configuration and/or construction. A configuration of an encapsulant is a modification of shape, contour, or inclination or any combination thereof. A configuration may be a microstructure or an optical directional component. A microstructure may be a Fresnel lense or a diffractive optical element, while an optical directional component may be an inclined plane or a curvature lens. The configuration can be disposed on any interfaces between two adjacent layers in an encapsulant or on the surface of an encapsulant. The surface of an encapsulant can be defined with medial surface, top surface and lateral surface. The medial surface of an encapsulant is the outline substantially facing to the partition. The top surface of an encapsulant is the surface about parallel to the plane of the substrate. For example, the top surface of the first encapsulant 111 is configured with a first microstructure 112, and the second encapsulant 121 may have a second microstructure 122. In addition, the second encapsulant 121, in order to improve the light receiving efficiency, may have different designs in the construction and configuration from the first encapsulant.

The surface of the encapsulants or the interface of any two layers may be formed as a microstructure. For example, the top surface of the uppermost layer of the first encapsulant 111 is configured as a microstructure 112 as illustrated in FIG. 1A. The encapsulant with microstructure(s) enhances the signal strength because the light is concentrated toward an intended direction while the light passes through the microstructure of the encapsulant. The microstructure may be a refractive microstructure or a diffractive microstructure. A refractive microstructure follows the law of refraction and is engineered to direct the light rays toward an object surface so that most reflected light may reach the photodetector 120. For example, a Fresnel lens microstructure effectively divides the continuous surface of a standard lens into a set of surfaces resulting in a substantial reduction in thickness. A diffractive microstructure re-distributes the propagating light wave energy on the projection plane. For example, a diffractive optical element (DOE) microstructure may be engineered to achieve a specific light distribution profile. A refractive microstructure or a diffractive microstructure is able to concentrate the emitting light from the light source 110 toward a desired direction so that the effective signals are improved.

The optical sensor module 10 is a compact packaged module comprising of a light source 110, a photodetector 120, an encapsulant, a partition 130, and a substrate 140. The present technology improves the performance of the optical sensor module 10 achieved by enhancing the light extraction efficiency, directing the light path, or reducing the stray light. An optical sensor module can be embodied as a simple composition with one light emitting diode (LED) and one silicon photodiode both mounted on a printed circuit board as a substrate 140. Each of the LED and the silicon photodiode are hermetically and separately sealed by epoxy encapsulants. In an example for measuring oxygenation of biological tissue, wavelengths in infrared and red regions are required. Therefore, one red LED and one infrared LED may be mounted on the same sensor module 10. In other examples, a single LED can be implemented that emits light in the infrared and red regions of the spectrum. In the embodiments described later in the text, one light source 110 and one photodetector 120 are used as examples. In other implementations that are within the scope of the present disclosure, the number and the arrangement of the light sources 110 and photodetectors 120 may be modified.

As shown in FIG. 1A, the general construction of the optical sensor module 10 is presented in a schematic cross sectional view. The optical sensor module 10 comprises a light source 110, a photodetector 120 and a partition 130 located between the light source and the photodetector 120. Each of the light source 110, the photodetector 120, the first encapsulant 111, the second encapsulant 121, and the partition 130 are mounted on a substrate 140. The first encapsulant 111 covers the light source 110, while the second encapsulant covers the photodetector 120. The optical sensor module has at least a part of the partition 130 being spaced apart from at least one of the first encapsulant 111 and the second encapsulant 121 by a predetermined distance. Furthermore, a microstructure 112 formed on an outer profile of at least one of the first encapsulant 111 and the second encapsulant 121. In FIG. 1B, the medial surface 310 of the first encapsulant 111 may have an inclined plane with an inclined angle 315 between the substrate 140 and the medial surface 310. In one example, the inclined angle 315 is forty degrees when the partition 130 is 0.6 millimeter height and the first encapsulant is about the same height with the partition 130.

In one embodiment of the present disclosure, as shown in FIGS. 2-5, the light source 110 is illustrated as two independent LEDs sealed in a first encapsulant 111, and the photodetector 120 may be a photodiode sealed in a second encapsulant 121. In addition, a partition 130 is located between the LEDs and the photodiode. An optical sensor module may have the packaging wall 131 extending around the encapsulants to reduce ambient stray light. The surface of both encapsulants have a predetermined surface configuration to enhance SNR. For ease of presentation, the medial surface 310 is the surface facing the partition 130 located between the light source 110 and the photodetector 120, the lateral surface is the surface facing toward the opposite side, and the top surface is about parallel to the substrate plane. The medial surface 310 of the first encapsulant 111 may have an inclined plane or a curvature lens or the combination thereof. An inclined plane may have an inclined angle 315 between the surface of the encapsulant and the plane of the substrate. The inclined angle may be around ninety degrees to twenty degrees. Therefore, light emitted from the light source is less shed onto the partition 130 to avoid light leakage direct from the light source 110 to the photodetector 120.

As illustrated in FIG. 2A, the light source 110 is sealed in the first encapsulant 111, and the top surface of the first encapsulant 111 is formed as a microstructure 112. Additionally, the photodetector 120 is sealed in the second encapsulant 121, and the top surface of the second encapsulant 121 is formed as a microstructure 122. In the cross sectional view (FIG. 2B) and oblique view (FIG. 2C), both the first encapsulant 111 and the second encapsulant 121 are separately constructed of a single layer in trapezoid shape. The medial and lateral surfaces of both the first encapsulant 111 and second encapsulant 121 have an angle. It is contemplated that the configuration and the material of the second encapsulant 121 may differ from the ones of the first encapsulant 111, in order to meet the requirements of the light receiving efficiency for specific applications.

As illustrated in FIG. 3A, the light source 110 is sealed in the first encapsulant 111, and the top surface of the first encapsulant 111 is formed as a microstructure 112. Additionally, the photodetector 120 is sealed in the second encapsulant 121, and the top surface of the second encapsulant 121 is formed as a microstructure 122. In the cross sectional view (FIG. 3B) and oblique view (FIG. 3C), both the first encapsulant 111 and the second encapsulant 121 are separately constructed of a single layer in trapezoid style. The medial and lateral surfaces of both the first 111 and second 121 encapsulants have a predetermined inclined angle 315. Additionally, the medial surface 310 of the first encapsulant 111 has a tilted at a larger angle, so that the light emitted from the medial surface 310 is mostly allowed to pass toward the upper part of the medial surface. In at least one example, the configuration and the material of the second encapsulant 121 may differ from the ones of the first encapsulant 111. The inclined angle of an inclined plane or a curvature lens may be larger or smaller than the medial surface 310 of the second encapsulant 121.

Figures 4A, 5A:
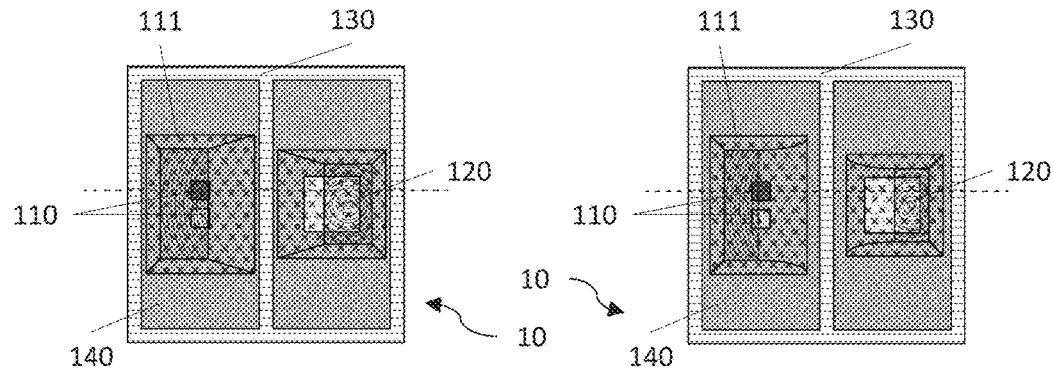
FIG. 4A-4C are schematic diagrams of a top view, cross-sectional view, and oblique sectional view, respectively, of an optical sensor in accordance with an embodiment of the present disclosure.
FIG. 5A-5C are schematic diagrams of a top view, cross-sectional view, and oblique sectional view, respectively, of an optical sensor in accordance with an embodiment of the present disclosure.
Figures 4B, 5B:
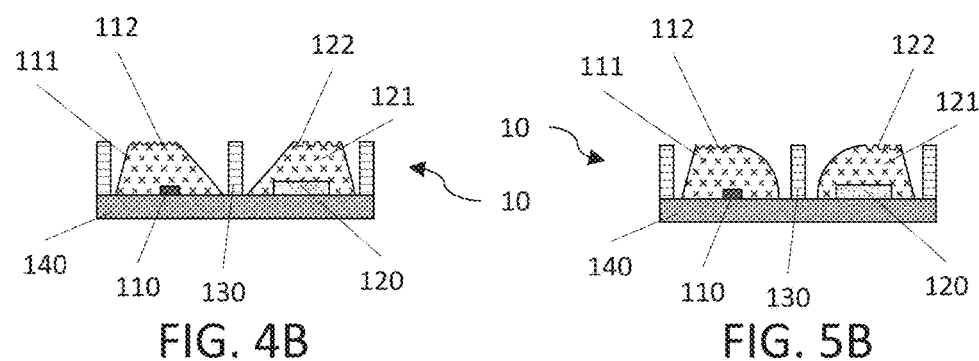
Figures 4C, 5C:
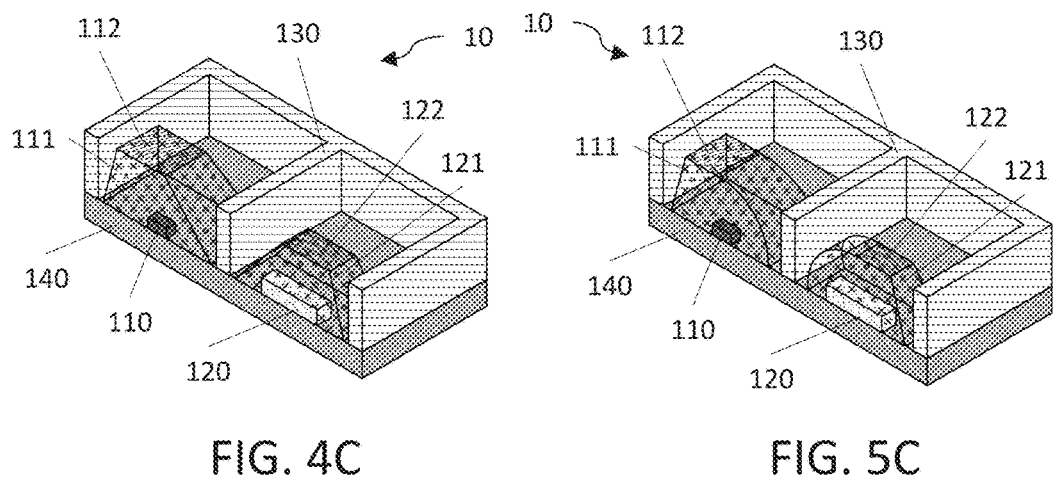

As illustrated in FIG. 4A, the light source 110 is sealed in the first encapsulant 111, and the top surface of the first encapsulant 111 is formed as a microstructure 112. Additionally, the photodetector 120 is sealed in the second encapsulant 121, and the top surface of the second encapsulant 121 is formed as a microstructure 122. In the cross sectional view (FIG. 4B) and oblique view (FIG. 4C), both the first encapsulant 111 and the second encapsulant 121 are separately constructed of a single layer in trapezoid style. The medial and lateral surfaces of both the first 111 and second 121 encapsulants have an inclined angle.

As illustrated in FIG. 5A, the light source 110 is sealed in the first encapsulant 111, and the top surface of the first encapsulant 111 is formed as a microstructure 112. Additionally, the photodetector 120 is sealed in the second encapsulant 121, and the top surface of the second encapsulant 121 is formed as a microstructure 122. In the cross sectional view (FIG. 5B) and oblique view (FIG. 5C), both the first encapsulant 111 and the second encapsulant 121 are separately constructed of a single layer in trapezoid style with a curved medial surface. The lateral surfaces of both the first 111 and second 121 encapsulants have a tilting angle. Specifically, the medial surfaces of both the first encapsulant 111 and the second encapsulant 121 have a curved medial surface, so that the extraction light from the medial surface is enhanced toward the upper part of the medial surface and more reflected light is received from the upper part of the medial surface of the second encapsulant 121. In at least one example, the configuration and the material of the second encapsulant 121 may differ from the ones of the first encapsulant 111. The inclined angle of the medial surface of the first encapsulant 111 may be different from the inclined angle of the medial surface of the second encapsulant 121. Furthermore, the optical sensor module may have an inclined plane on the medial surface of the first encapsulant 111, while a curvature lens on the medial surface of the second encapsulant 121.

In the embodiments shown in FIG. 6, the optical sensor modules 10 may be applied directly on the object surface 190 to have the top surfaces of the encapsulants contact the object surface 190. The object surface 190 may be the surface of a biological tissue, such as a skin or a mucosa. In FIGS. 6A and C, the object surface 190 contacts as much the top surface of the encapsulants as possible to achieve better SNR. In the cross sectional view FIG. 6B, the object surface 190 directly contacts the top surface of the encapsulants.

In one embodiment of the present disclosure, as shown in FIGS. 7-11, the light source 110 may include two LEDs sealed in a first encapsulant 111, and the photodetector 120 may be a photodiode sealed in a second encapsulant 121. Each top surface of the encapsulants is configured as a microstructure. The optical sensor module 10 may further comprise a cover 150 above the first encapsulant 111 and the second encapsulant 121. The cover 150 may be located, during application, between the encapsulants and the object surface 190. The cover 150 serves as a contact interface between the object surface 190 (for example, a biological tissue surface or a skin surface) to increase the durability of the optical sensor module 10 and the consistency of measurement. The cover 150 provide a contact surface with the object surface 190 and keep the optical path clear from the water or dust. The cover 150 may be integrated as a part of the optical sensor module 10 or may be a part of the housing of the optical sensor device. As shown in FIGS. 7A and C, the optical sensor module 10 may further comprise a cover 150 above the first encapsulant 111 and the second encapsulant 121. In addition, there may be a slight gap between the cover 150 and the top surface of the encapsulants to reduce light leakage via the cover 150 (FIG. 7B).

In one embodiment as shown in FIG. 8A, the optical sensor module 10 comprises a cover 150. In addition, the internal surface or the external surface of the cover 150 may be coated with a thin film 151. The thin film 151 may be an anti-reflective thin film (such as index-matching thin film or interference thin film), or an anti-scratch thin film (such as polyethylene terephthalate, or silicon hard coating). As shown in FIG. 8B, the external surface of cover 150 is covered with an anti-scratch thin film 151 and the internal surface of the cover 150 is covered with an anti-reflective thin film 151. In at least one example, the two surfaces may be covered with same kind of thin film 151 or one of the surfaces of the cover 150 may have no thin film. It is contemplated that the cover 150 may be coated with a filter thin film to clear out undesired range of lights.

In one embodiment, the optical sensor module 10 may comprise a thin film 160 covering an encapsulant. With thin film technology, the SNR of the optical signals may be further improved. The thin film 160 may be an anti-reflective thin film or a filter thin film. The anti-reflective thin film may be an index-matching film (for example, Rayleigh film) or an interference film to improve light extraction efficiency by reducing Fresnel reflection at the interface between the encapsulants and the environmental medium. The filter thin film may be a long-pass filter, a short-pass filter, or a band-pass filter to clear down the full width at half maximum (FWHM) of the emitting light or filter out the noise from undesired wavelengths. The optical sensor module 10 may further comprise a thin film 160 covering the surface of the first encapsulant 111 and/or the second encapsulant 121.

As shown in FIG. 9, both the surfaces of the first encapsulant 111 and the second encapsulant 121 are coated with a thin film 160. The thin film 160 of the first encapsulant 111 is embodied as an anti-reflective thin film (FIG. 9B) and the thin film 160 of the second encapsulant 121 is embodied as a band-pass filter thin film (FIG. 9C). The anti-reflective thin film improves the light extraction efficiency and the band-pass filter thin film reduces noise. In at least one example, the thin film 160 of the first encapsulant 111 is embodied as a band-pass filter thin film and the thin film 160 of the second encapsulant 121 is embodied as an anti-reflective thin film, so that the FWHM of the emitting light has a clear cut-off wavelength and the photodiode detects the filtered signals within a specific range of wavelengths. In the application of fluorescence detection long-pass filter thin film maybe applied to the second encapsulant 121 to acquire a clear fluorescent signal avoiding the excitation light. Also, the optical sensor module 10 may have a cover 150 as shown in FIG. 10A and thin films 160 over the first encapsulant 111 and the second encapsulant 121 (FIGS. 10 B and C). Furthermore, the optical sensor module 10 may further comprise both a cover 150 coated with thin films 151 and the thin films 160 covering the encapsulants (FIG. 11A). The thin film 151 of external surface of the cover 150 may be an anti-scratch thin film and the one 151 of the internal surface may be as an anti-reflective thin film (FIG. 11B). The thin film 160 of the first encapsulant 111 may be as an anti-reflective thin film (FIG. 11 C) and the thin film 160 of the second encapsulant 121 may be as a band-pass filter thin film (FIG. 11D).

The light source 110 and the photodetector 120 in an optical sensor module 10 may be arranged in a two dimensional pattern in order to increase SNR as shown in FIGS. 12-15. In general, the light source 110 may be a set of multiple light emitters with different wavelengths encapsulated in the central region; the photodetector 120 may be a single entity surrounding the light source 110, or may be multiple photodetectors 120 located around the central light source 110. The central light source 110 is covered with a first encapsulant 111 and each photodetector 120 is covered with a second encapsulant 121 (FIG. 12A). In cross sectional view (FIG. 12B) and oblique view (FIG. 12C), the photodetector 120 sits beside the light source 110, and the optical insulating partition 130 separates the light source 110 and photodetector 120. Furthermore, the top surface of the first encapsulant 111 is configured as a microstructure 112. The first microstructure 112 is capable of guiding the emitting light outward so that more reflected light reaches the surrounding photodetector 120. Also, the top surface of the second encapsulant 121 is configured as a microstructure 122 to improve the light receiving efficiency. The microstructure 122 of the second encapsulant 121 may have different designs from the one of the first encapsulant 111 to improve SNR. In at least one example, the configuration of the encapsulants (for example, microstructure), the surface thin film 160 covering the encapsulants, and the cover 150 mentioned in FIG. 7-11 may be applied to the two dimensional pattern sensor module 10 described in FIG. 12-15.

In one embodiment of the present disclosure, as shown in FIG. 13, the light source 110 is illustrated as two independent LEDs sealed in a first encapsulant 111, and the photodetector 120 may be a single annular photodiode sealed in a second encapsulant 121. In addition, an annular partition 130 is located between the LEDs and the photodiode to reduce direct light leakage from the light source 110 to the photodetector 120; a second annular partition 130 may reside around the second encapsulant 121 to reduce ambient stray light.

As illustrated in FIG. 13A, the optical sensor module 10 can be embodied as a single annular photodiode surrounding the central light source 110. The central light source 110 may comprise two LEDs having different emitting wavelength (s), and the both of the two LEDs are covered with the first encapsulant 111. The photodetector 120 may be a single piece of annular silicon photodiode surrounding the central light source 110, and the annular photodiode is covered with the annular second encapsulant 121. The top surface of the first encapsulant 111 is configured as a microstructure 112, and the first microstructure 112 may be in a concentric circular pattern. Additionally, the top surface of the second encapsulant 121 is configured as a second microstructure 122, which can be a concentric circular pattern. In the cross sectional view (FIG. 13B) and oblique view (FIG. 13C), both the first encapsulant 111 and the second encapsulant 121 are separately constructed of in trapezoid shape, which features the narrower upper part of the encapsulant. The arrangement of the first encapsulant and the second encapsulants may be a reflectional symmetric patterns, such as linear, elliptic, hexagonal, or polygonal. The patterns may have some extent of SNR improvement due to the photodetector 120 locating beside the light source 110. In at least one example, the construction, the microstructure, the material of the second encapsulant 121 may differ from the ones of the first encapsulant 111, in order to meet the requirements of the light receiving efficiency for specific applications. For example, the second encapsulants have multilayer construction with microstructures on the top surfaces.

In one embodiment of the present disclosure, as shown in FIG. 14, the light source 110 is illustrated as two independent LEDs sealed in the first encapsulant 111, and the photodetector 120 may be a group of separate photodiodes, each sealed in a second encapsulant 121. In addition, a partition 130 is located around the LEDs to reduce direct crosstalk; the photodiodes may have a packaging wall 131 around the second encapsulants 121 to reduce both direct crosstalk and ambient stray light.

Figure 14A:
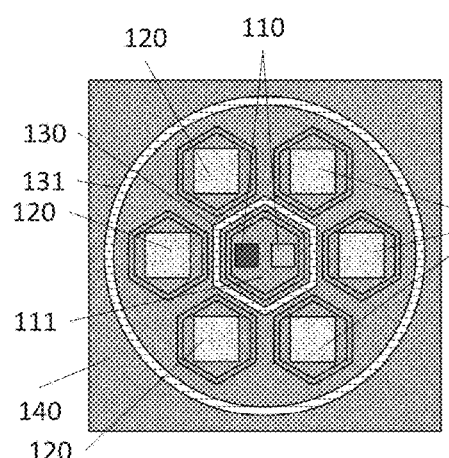
FIG. 14A-14C are schematic diagrams of a top view, cross-sectional view, and oblique sectional view, respectively, of an optical sensor module in accordance with an embodiment of the present disclosure.

As illustrated in FIG. 14A, the optical sensor module 10 may be embodied as multiple photodiodes surrounding the central light source 110. The central light source 110 may comprise two LEDs of different emitting wavelength, and the LEDs are covered with a first encapsulant 111. The photodetectors 120 may be a group of square photodiodes annularly arranged around the central light source 110, and each photodiode is covered with a second encapsulant 121. Also, a hexagonal partition 130 is located around the LEDs to reduce direct light leakage; photodiodes may have a lateral packaging wall 131 around the second encapsulants 121 to reduce and ambient stray light. In the cross sectional view (FIG. 14B) and oblique view (FIG. 14C), both the first encapsulant 111 and the second encapsulant 121 are separately constructed of in trapezoid shape, which features the narrower upper part of the encapsulant. The top surface of the first encapsulant 111 is configured as a microstructure 112, and the first microstructure 112 may be embodied as a concentric circular pattern. Additionally the top surface of the second encapsulant 121 is configured as a microstructure 122, and the second microstructure 122 may be embodied as a concentric circular pattern. While the illustrated pattern is a hexagonal pattern, the present disclosure includes other types of polygonal patterns, such as triangular, pentagonal, or octagonal. All other patterns may have some extent of SNR improvement due to the photodetectors 120 locating beside the light source 110. In at least one example, the construction, the microstructure, the material of the second encapsulants 121 may differ from the ones of the first encapsulant 111, in order to meet the requirements of the light receiving efficiency for specific applications.

Figure 15A:
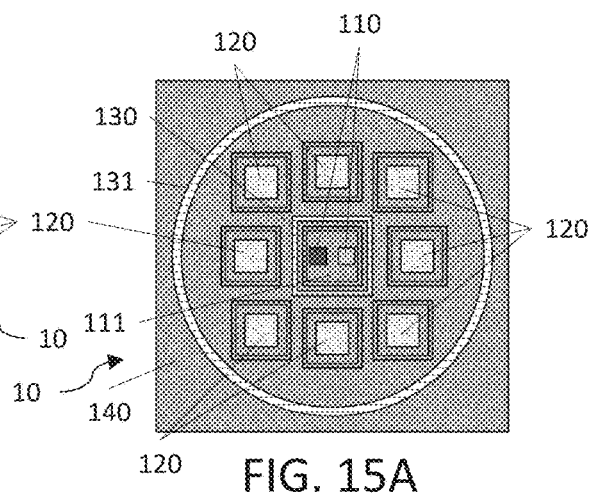
FIG. 15A-15C are schematic diagrams of a top view, cross-sectional view, and oblique sectional view, respectively, of an optical sensor module in accordance with an embodiment of the present disclosure.
Figure 14B:
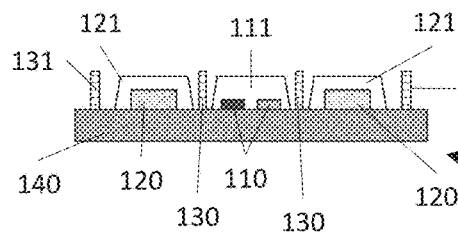
Figure 15B:
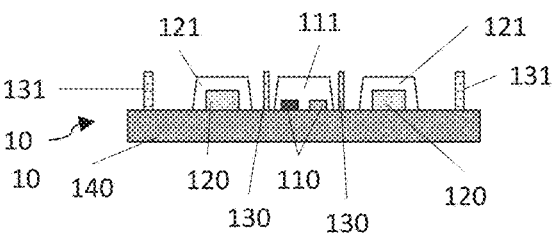
Figure 14C:
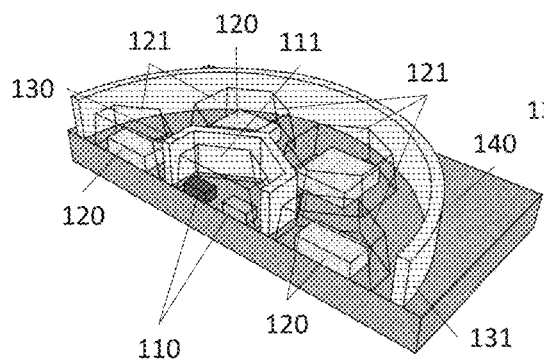
Figure 15C:
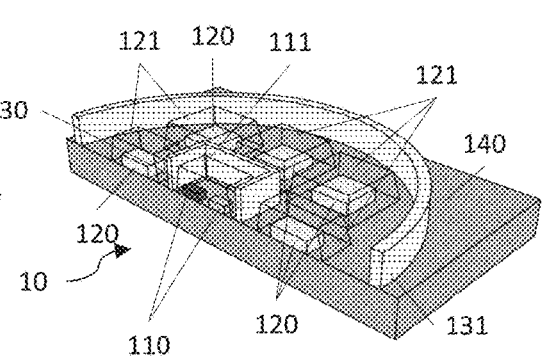

As illustrated in FIG. 15A, the optical sensor module 10 may be embodied as multiple photodiodes surrounding the central light source 110. The central light source 110 may comprise two LEDs of different emitting wavelength, and the LEDs is covered with a first encapsulant 111. The photodetectors 120 may be a group of square photodiodes annularly arranged around the central light source 110, and each photodiode is covered with a second encapsulant 121. Additionally, a square partition 130 is located around the light source 110 and the photodetectors 120 may have a lateral packaging wall 131 around the second encapsulants 121 to reduce ambient stray light. In the cross sectional view (FIG. 15B) and oblique view (FIG. 15C), both the first encapsulant 111 and the second encapsulant 121 are separately constructed with the feature of the narrower upper part of the encapsulant. The top surface of the first encapsulant 111 is configured as a microstructure 112, and the first microstructure 112 may be embodied as a concentric circular pattern. Additionally, the top surface of the second encapsulant 121 is configured as a microstructure 122, and the second microstructure 122 may be embodied as a concentric circular pattern. Without departing from the scope of the disclosure the arrangement pattern of an optical sensor module may be other polygonal patterns, such as triangular, pentagonal, or octagonal. All other patterns may have some extent of SNR improvement due to the photodetectors 120 locating beside the light source 110. In at least one example, the construction, the microstructure, the material of the second encapsulants 121 may differ from each other or the ones of the first encapsulant 111.

In the present disclosure, the optical sensor module 10 may employ the encapsulant 111 with multiple refractive index layers over the light source 110 for improving the light extraction efficiency or may employ the encapsulant 111 with multiple refractive index layers over the photodetector 120 for improving reflected light receiving efficiency. The optical sensor module 10 enhances the signal strength because the total internal reflection of the emitted light is reduced while the light passes through the encapsulant 111 layer by layer outward from the light source 110.

For example, the first encapsulant 111, formed on the substrate 140 over the light source 110, includes multiple refractive index layers. Multiple refractive index layers may be constructed by stacking multiple physical layers with different refractive indices or may be constructed by a single entity of gradient refractive index. The refractive index of each layer of the first encapsulant 111 decreases layer by layer from lower layers to upper layers. As shown in the FIG. 16A, the first encapsulant 111 includes a plurality of layers (two layers are illustrated) in which each layer is formed of material that allows the emitted light by the light source 110 to pass through. For example, the refractive index ($n_1$) of the lower layer (bottom layer) of the first encapsulant 111, formed directly over the light source 110, is higher than the refractive index ($n_2$) of the upper layer (top layer), which abuts the top surface of the bottom layer, of the first encapsulant 111. With respect to conventional encapsulant with only a single refractive index layer over the light source 110, the decreasing refractive index of the adjacent layers of the first encapsulant 111, gradually mediates a drastic refractive index difference between the light source 110 and the environmental medium. Generally, the refractive index of an optoelectronic transducer is greater than three, while the refractive index of ambient air is about one. The critical angle ($\theta c = \arc \sin(n_2/n_1)$) occurs at the interface of adjacent layers of the first encapsulant 111 has a significant increase compared to a bare light source 110 alone or a light source 110 merely with a single layer of encapsulant. Also, the critical angle at the interface between the top layer of the first encapsulant 111 and the environmental medium surrounding the optical sensor module 10 is widened. The amount of the total internal reflection is reduced while the light emitted by the light source 110 sequentially passes through the decreasing refractive indices of the multiple layers in the first encapsulant 111. Consequently, the optical sensor module 10 enhances the signal strength by improving the light extraction efficiency according to the first encapsulant 111 with a plurality of refractive index layers. Similarly, a second encapsulant with multiple refractive index layers may be formed over a photodetector 120 to improve light receiving efficiency for the signal light coming from the light source 110 and reflected by an object surface.

Figure 16A:
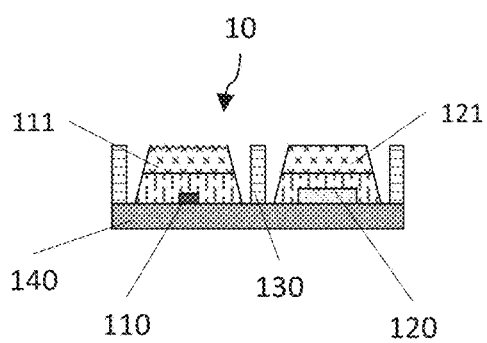
FIG. 16A is a schematic diagram of a cross-sectional view of an optical sensor in accordance with one embodiment of the present disclosure.

As shown in FIG. 16A, the general construction of the optical sensor module 10 is presented in a schematic cross sectional view. The optical sensor module 10 comprises a LED, a silicon photodiode, and a partition 130 located between the LED and the photodetector 120, wherein all the above are mounted on a substrate 140. The first encapsulant 111 covers the light source 110, while the second encapsulant 121 covers the photodetector 120. In the embodiments, an encapsulant may have modifications in configuration and construction. For example, the top surface of the first encapsulant 111 is configured as a first microstructure 112, and the second encapsulant 121 may have a second microstructure 122. The first encapsulant 111 is constructed with multiple refractive index layers, and a double layer construction is illustrated in FIG. 16A, while three or more layers may be realized. The interface between any two layers may also have a configuration, such as a microstructure 112 or an optical directional component 113. Similarly, the second encapsulant 121 may also be constructed with multiple layers and may have a surface microstructure 122 or a configuration (for example, a curvature lens) at the interface between any two layers. In addition, the second encapsulant 121, in order to improve the light receiving efficiency, may have different designs in the construction and configuration from the first encapsulant 111.

Figure 16B:
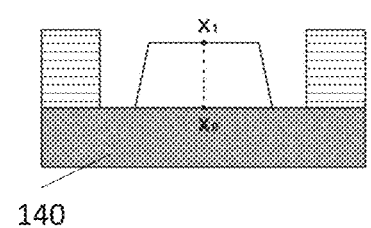
FIG. 16B is the schematic diagram of a cross-sectional view of one of the encapsulants.
Figure 16C:
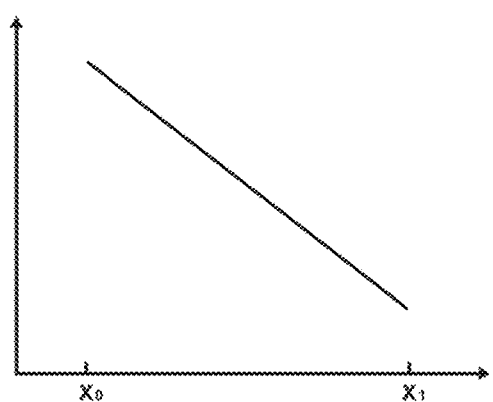
FIG. 16C-16E are the graphs of the refractive index as a function of the distance from the substrate, wherein the horizontal axis represents the distance and the vertical axis represents the refractive index.
Figure 16D:
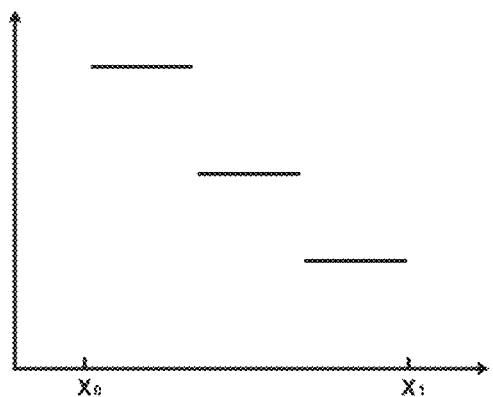
Figure 16E:
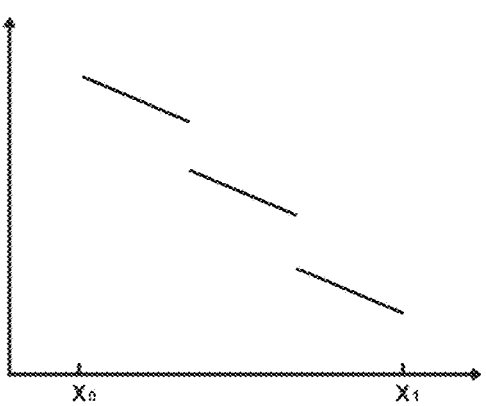

FIG. 16B-E shows the relation between refractive index within an encapsulant with multiple refractive index layers and distance from the substrate. In FIG. 16B, a dot line connecting between x0 and x1 indicates the corresponding measurements of refractive index, where x0 represents one of the most proximal portions in an encapsulant and x1 represents one of the most distal portions in an encapsulant. FIG. 16C-E shows the refractive index function of distance from the substrate. In one example as illustrated in FIG. 16C, the encapsulant with multiple refractive index layers has gradient refractive index. In one example as illustrated in FIG. 16D, the encapsulant with multiple refractive index layers has discrete refractive indices. In one example as illustrated in FIG. 16E, the encapsulant with multiple refractive index layers has multiple physical layers with gradient refractive index. In addition, the gradient refractive index may be linear or non-linear to the distance. The refractive index function of distance may be monotonically decreasing. In addition, non-monotonicity of the refractive index function of distance may be tolerable.

In one embodiment of the present disclosure, as shown in FIGS. 17-19, the light source 110 is illustrated as two independent LEDs sealed in a first encapsulant 111, and the photodetector 120 may be a photodiode sealed in a second encapsulant 121. The first encapsulant 111 and/or the second encapsulant 121 is constructed with multiple refractive index layers, and the top surface of the first encapsulant 111 or the second encapsulant 121 is configured as a microstructure 112.

Figure 17A:
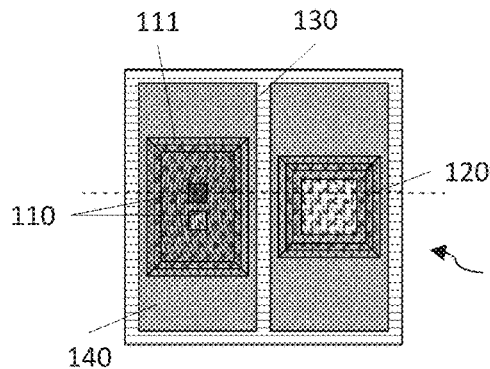
FIG. 17A-17C are schematic diagrams of a top view, cross-sectional view, and oblique sectional view, respectively, of an optical sensor module in accordance with an embodiment of the present disclosure.
Figure 17B:
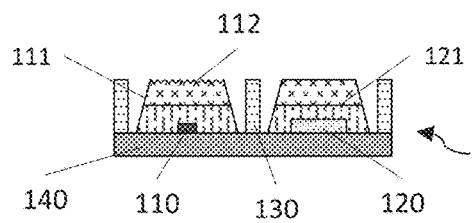
Figure 17C:
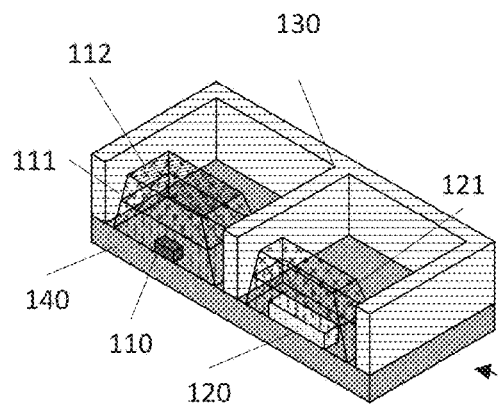

As illustrated in FIG. 17A, the top surface of the upper layer of the first encapsulant 111 is configured as a microstructure 112, and the microstructure 112 is embodied as a set of concentric arcs concave toward the photodiode, while a photodiode is sealed in the second encapsulant 121 without a microstructure. In the cross sectional view (FIG. 17B) and oblique view (FIG. 17C), both the first encapsulant 111 and the second encapsulant 121 are separately constructed of a stack of multiple layers in Babel Tower style, which features the distal portion of the encapsulant is narrower than the proximal portion. Also, the multiple refractive index layers has different refractive indices arranged in a decreasing fashion from proximal layers to distal layers.

Figure 18A:
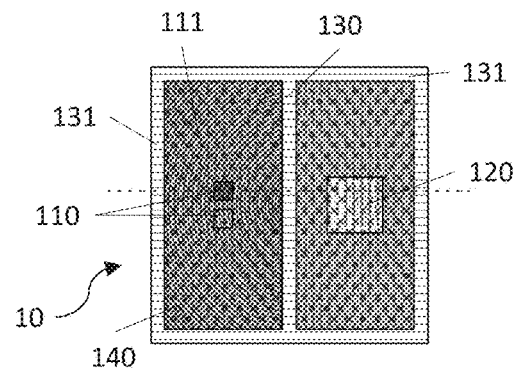
FIG. 18A-18C are schematic diagrams of a top view, cross-sectional view, and oblique sectional view, respectively, of an optical sensor module in accordance with an embodiment of the present disclosure.
Figure 18B:
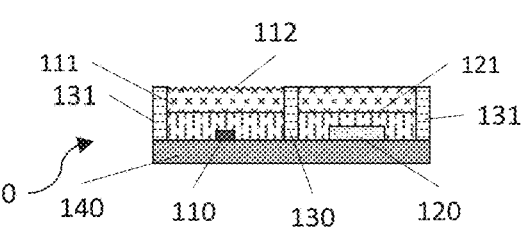
Figure 18C:
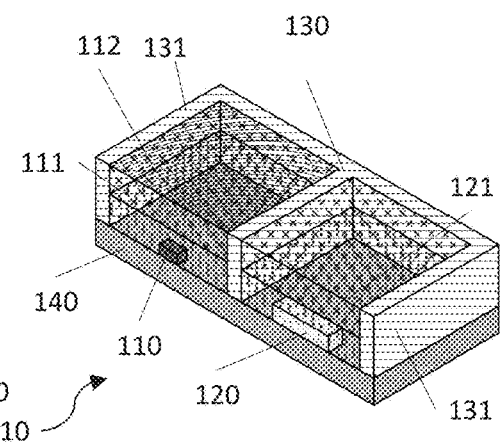

As illustrated in FIG. 18A, the top surface of the distal layer of the first encapsulant 111 is configured as a microstructure 112, and the microstructure 112 is embodied as a set of concentric arcs concave toward the photodiode, while a photodiode is sealed in the second encapsulant 121 without a microstructure. In the cross sectional view (FIG. 18B) and oblique view (FIG. 18C), both the first encapsulant 111 and the second encapsulant 121 are separately constructed in multiple refractive index layers in a pancake stack style, which features the circumferential flank sides of the multi-layer encapsulant abutting the partition 130 and the packaging wall 131. The multiple refractive index layers has different refractive indices arranged in a decreasing fashion from lower layers to upper layers.

Figure 19A:
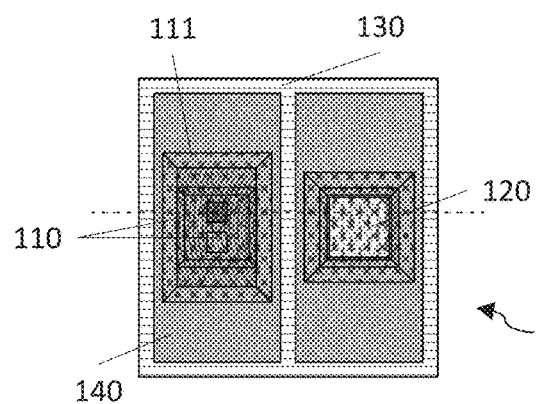
FIG. 19A-19C are schematic diagrams of a top view, cross-sectional view, and oblique sectional view, respectively, of an optical sensor module in accordance with an embodiment of the present disclosure.
Figure 19B:
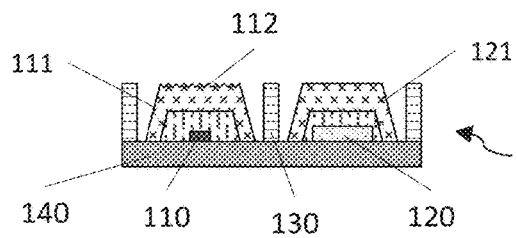
Figure 19C:
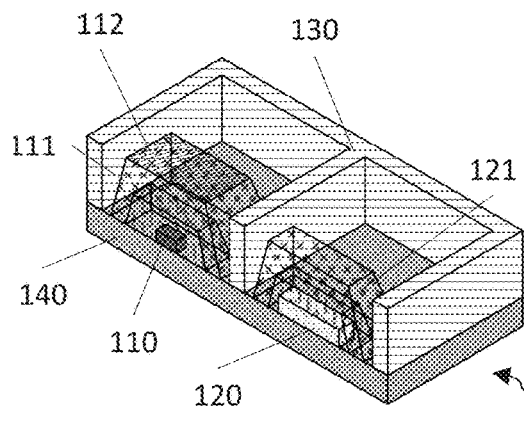

As illustrated in FIG. 19A, the top surface of the distal layer of the first encapsulant 111 is configured as a microstructure 112, and the microstructure 112 is embodied as a set of concentric arcs concave toward the photodiode, while a photodiode is sealed in the second encapsulant 121 without a microstructure. In the cross sectional view (FIG. 19B) and oblique view (FIG. 19C), both the first encapsulant 111 and the second encapsulant 121 are separately constructed in multiple refractive index layers in a cup-stacking style, which features the upper layer embracing the adjacent lower layer. The multiple refractive index layers has different refractive indices arranged in a decreasing fashion from lower layers to upper layers.

It is contemplated that the second encapsulant 121 may be constructed as a single entity (single layer) or a multi-layer stack, and constructed in various stacking styles. The construction and the material of the second encapsulant 121 may differ from the ones of the first encapsulant 111, in order to meet the requirements of the light receiving efficiency for specific applications.

In one embodiment of the present disclosure, as shown in FIGS. 20-22, the light source 110 is illustrated as two independent LEDs sealed in a first encapsulant 111, and the photodetector 120 may be a photodiode sealed in a second encapsulant 121. The first encapsulant 111 is constructed with a multiple refractive index layers, and the top surface of the first encapsulant 111 is configured as a microstructure 112. Also, the second encapsulant 121 is constructed with multiple refractive index layers, and the top surface of the second encapsulant 121 is configured as a microstructure 122.

Figure 20A:
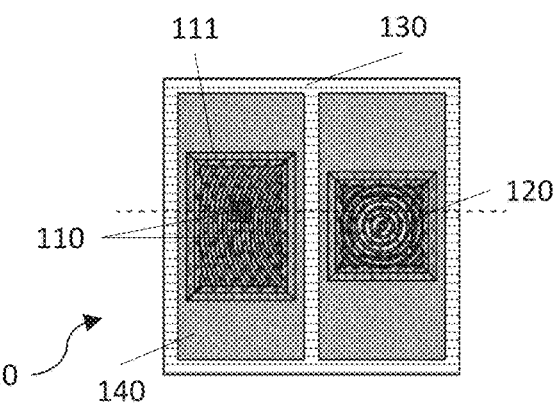
FIG. 20A-20C are schematic diagrams of a top view, cross-sectional view, and oblique sectional view, respectively, of an optical sensor module in accordance with an embodiment of the present disclosure.
Figure 20B:
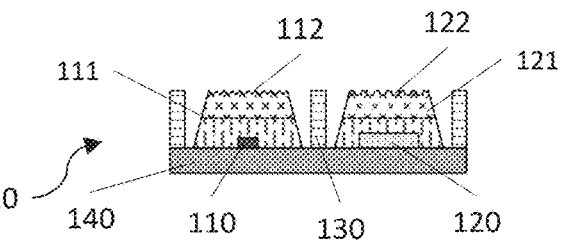
Figure 20C:
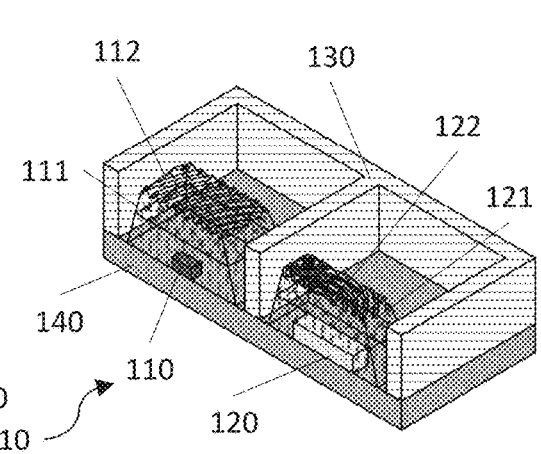

As illustrated in FIG. 20A, the top surface of the first encapsulant 111 is configured as a microstructure 112, and the microstructure 112 is embodied as a set of concentric arcs concave toward the photodiode. Additionally, the top surface of the second encapsulant 121 is configured as a microstructure 122, which is embodied as a set of concentric circles. In the cross sectional view (FIG. 20B) and oblique view (FIG. 20C), both the first encapsulant 111 and the second encapsulant 121 are separately constructed of multiple refractive index layers in Babel Tower style. Also, the multiple refractive index layers has different refractive indices arranged in a decreasing fashion from lower layers to upper layers. It is contemplated that the second encapsulant 121 may be constructed as a single entity (single layer) or a multi-layer stack, and constructed in various stacking styles. The construction and the material of the second encapsulant 121 may differ from the ones of the first encapsulant 111, in order to meet the requirements of the light receiving efficiency for specific applications.

Figure 21A:
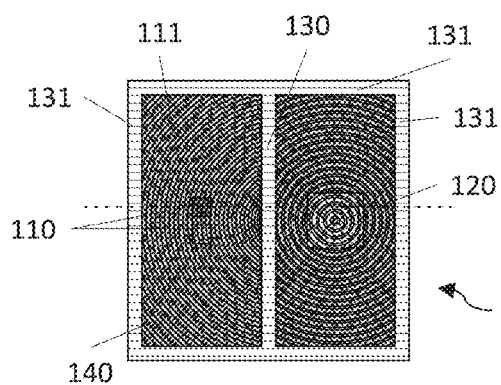
FIG. 21A-21C are schematic diagrams of a top view, cross-sectional view, and oblique sectional view, respectively, of an optical sensor module in accordance with an embodiment of the present disclosure.
Figure 21B:
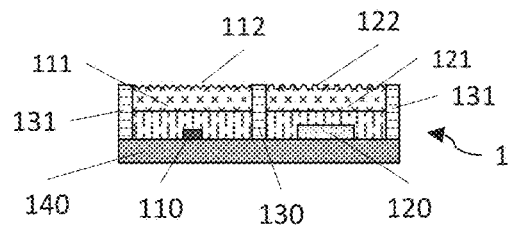
Figure 21C:
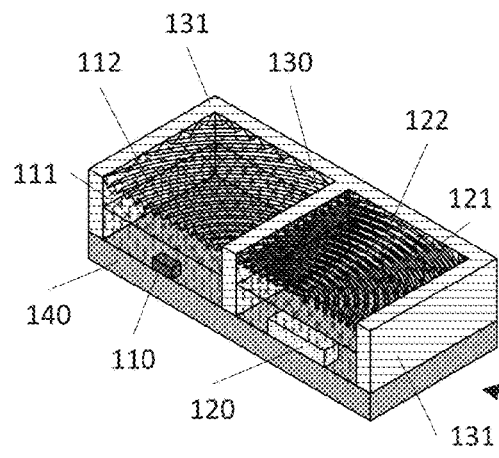

As illustrated in FIG. 21A, the top surface of the upper layer of the first encapsulant 111 is configured as a microstructure 112, and the microstructure 112 is embodied as a set of concentric arcs concave toward the photodiode. Additionally, the top surface of the second encapsulant 121 is configured as a microstructure 122, and the microstructure 122 is embodied as a set of concentric circles. In the cross sectional view (FIG. 21B) and oblique view (FIG. 21C), both the first encapsulant 111 and the second encapsulant 121 are separately constructed in multiple refractive index layers in a pancake stack style, which features the flank sides of the multi-layer encapsulant abutting the packaging wall 131. Also, the multiple refractive index layers has different refractive indices arranged in a decreasing fashion from lower layers to upper layers.

Figure 22A:
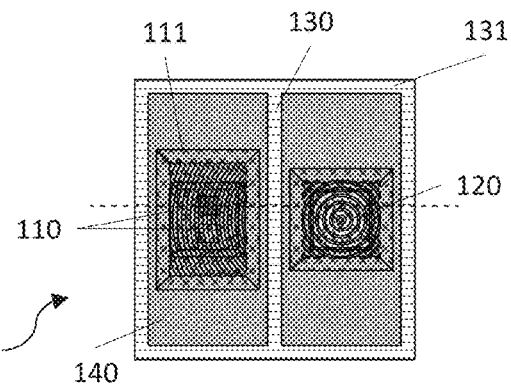
FIG. 22A-22C are schematic diagrams of a top view, cross-sectional view, and oblique sectional view, respectively, of an optical sensor module in accordance with an embodiment of the present disclosure.
Figure 22B:
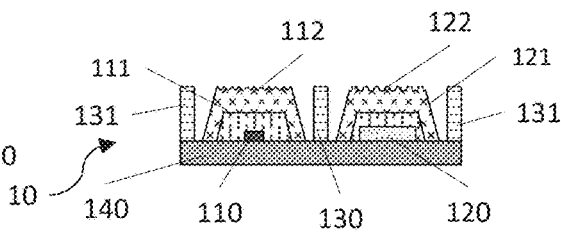
Figure 22C:
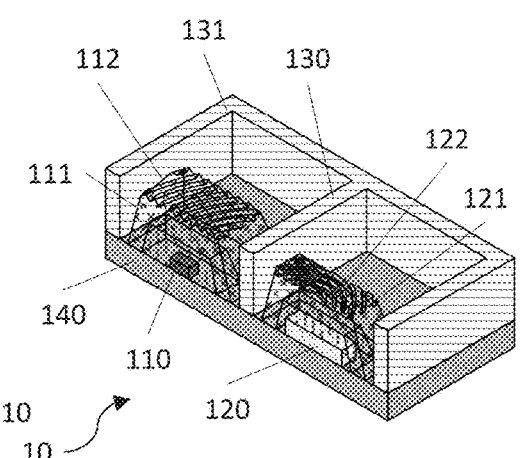

As illustrated in FIG. 22A, the top surface of the upper layer of the first encapsulant 111 is configured as a microstructure 112, and the microstructure 112 is embodied as a set of concentric arcs concave toward the photodiode. Additionally, the top surface of the second encapsulant 121 is configured as a microstructure 122, and the microstructure 122 is embodied as a set of concentric circles. In the cross sectional view (FIG. 22B) and oblique view (FIG. 22C), both the first encapsulant 111 and the second encapsulant 121 are separately constructed in multiple refractive index layers in a cup-stacking style. Also, the multiple refractive index layers construction has different refractive indices arranged in a decreasing fashion from lower layers to upper layers.

In one embodiment of the present disclosure, as shown in FIGS. 23-25, the light source 110 is illustrated as two independent LEDs sealed in a first encapsulant 111, and the photodetector 120 may be a photodiode sealed in a second encapsulant 121. The first encapsulant 111 is constructed with multiple refractive index layers, and one interface of any two adjacent layers of the first encapsulant 111 is configured as a microstructure 112. Also, one interface of any two adjacent layers of the second encapsulant 121 may be configured as a microstructure 122.

Figure 23A:
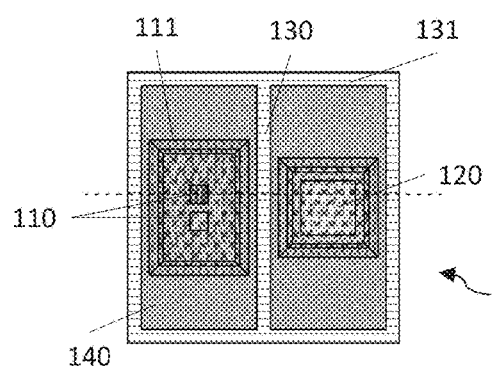
FIG. 23A-23C are schematic diagrams of a top view, cross-sectional view, and oblique sectional view, respectively, of an optical sensor module in accordance with an embodiment of the present disclosure.
Figure 23B:
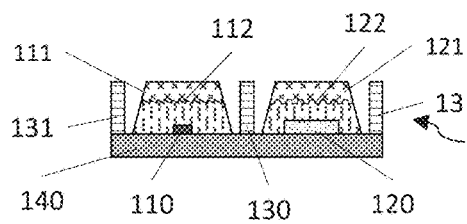
Figure 23C:
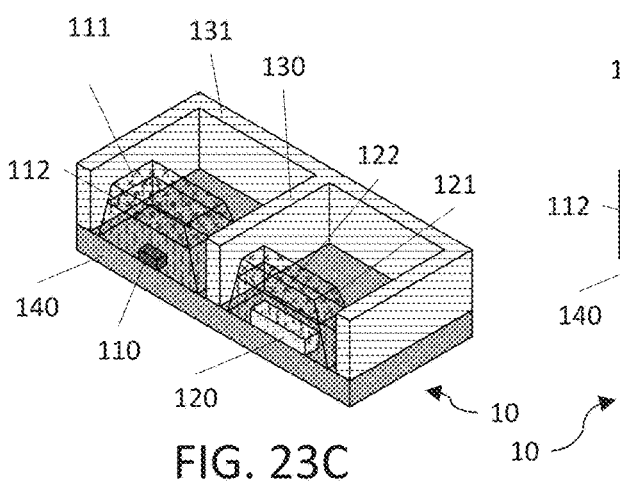

As illustrated in FIG. 23A, one interface of any two adjacent layers of the first encapsulant 111 is configured as a microstructure 112, and the microstructure 112 is embodied as a set of concentric arcs concave toward the photodiode. Additionally, one of the interface of any two adjacent layers of the second encapsulant 121 is configured as a microstructure 122, and the microstructure 122 is embodied as a set of concentric circles. In the cross sectional view (FIG. 23B) and oblique view (FIG. 23C), both the first encapsulant 111 and the second encapsulant 121 are separately constructed with multiple refractive index layers in Babel Tower style. Also, the multiple refractive index layers construction has different refractive indices arranged in a decreasing fashion from lower layers to upper layers.

Figure 24A:
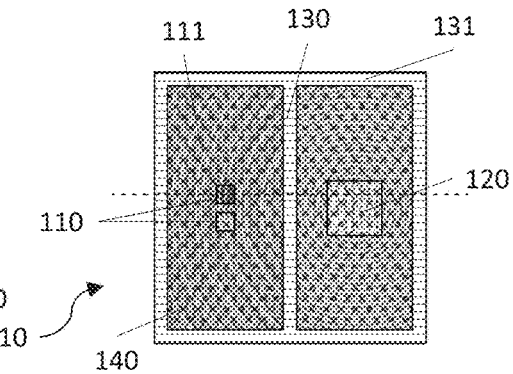
FIG. 24A-24C are schematic diagrams of a top view, cross-sectional view, and oblique sectional view, respectively, of an optical sensor module in accordance with an embodiment of the present disclosure.
Figure 24B:
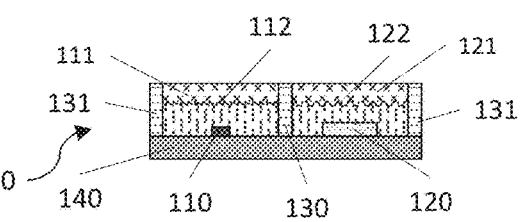
Figure 24C:
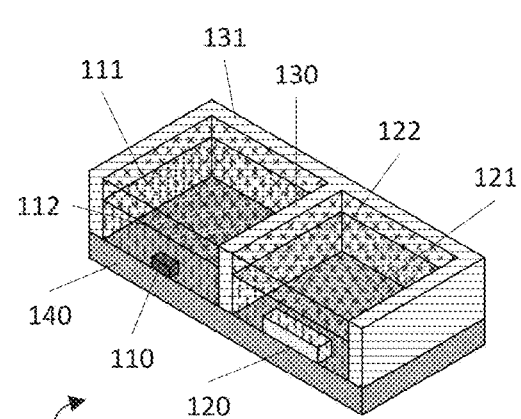

As illustrated in FIG. 24A, one interface of any two adjacent layers of the first encapsulant 111 is configured as a microstructure 112, and the microstructure 112 is embodied as a set of concentric arcs concave toward the photodiode. Additionally one interface of any two adjacent layers of the second encapsulant 121 is configured as a microstructure 122, and the microstructure 122 is embodied as a set of concentric circles. In the cross sectional view (FIG. 24B) and oblique view (FIG. 24C), both the first encapsulant 111 and the second encapsulant 121 are separately constructed multiple refractive index layers in a pancake stack style.

Figure 25A:
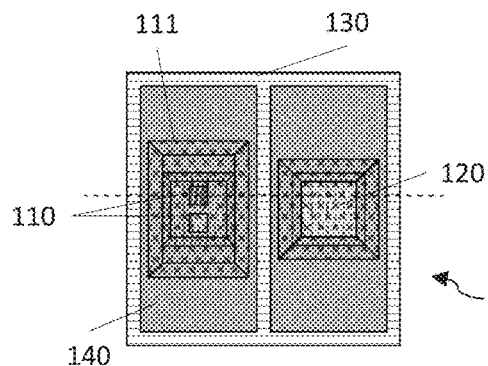
FIG. 25A-25C are schematic diagrams of a top view, cross-sectional view, and oblique sectional view, respectively, of an optical sensor module in accordance with an embodiment of the present disclosure.
Figure 25B:
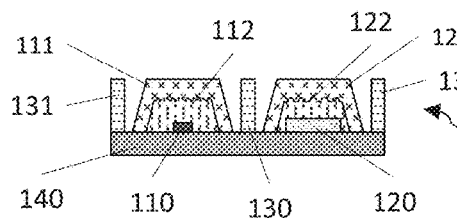
Figure 25C:
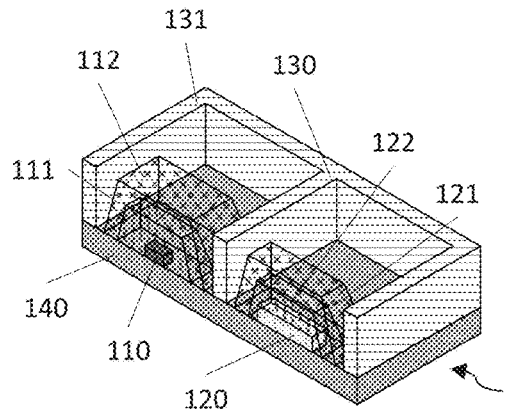

As illustrated in FIG. 25A, one interface of any two adjacent layers of the first encapsulant 111 is configured as a microstructure 112, and the microstructure 112 is embodied as a set of concentric arcs concaved toward the photodiode. Additionally, one interface of any two adjacent layers of the second encapsulant 121 is configured as a microstructure 122, which is embodied as a set of concentric circles. In the cross sectional view (FIG. 25B) and oblique view (FIG. 25C), both the first encapsulant 111 and the second encapsulant 121 are separately constructed with multiple refractive index layers in a cup-stacking style. Also, the multiple refractive index layers construction has different refractive indices arranged in a decreasing fashion from lower layers to upper layers.

In one embodiment of the present disclosure, as shown in FIGS. 26-28, the light source 110 is illustrated as two independent LEDs sealed in a first encapsulant 111, and the photodetector 120 may be a photodiode sealed in a second encapsulant 121. The first encapsulant 111 is constructed with multiple refractive index layers, and multiple interfaces of any two adjacent layers of the first encapsulant 111 is configured as a microstructure 112.

Figure 26A:
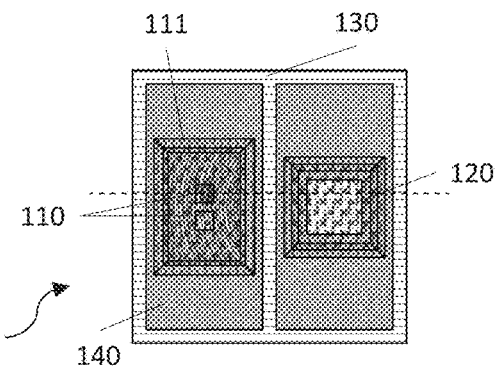
FIG. 26A-26C are schematic diagrams of a top view, cross-sectional view, and oblique sectional view, respectively, of an optical sensor module in accordance with an embodiment of the present disclosure.
Figure 26B:
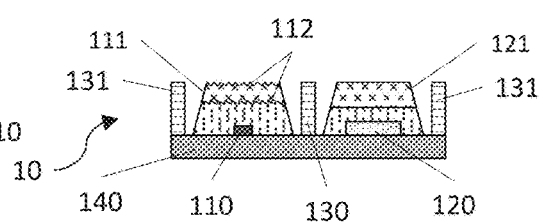
Figure 26C:
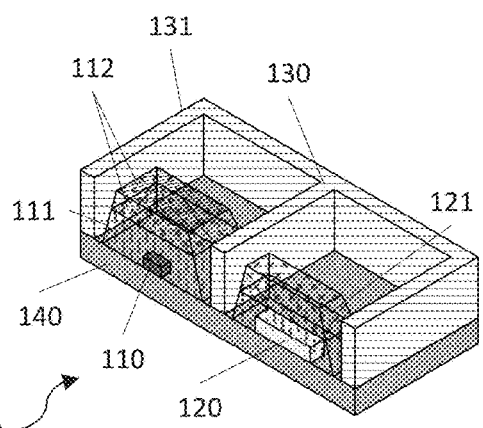

As illustrated in FIG. 26A, the first encapsulant 111 has multiple microstructures 112 formed as the top surface of the uppermost layer and formed as one interface of the adjacent layers inside, and the microstructure 112 is embodied as a set of concentric arcs concave toward the photodetector 120, while the second encapsulant 121 may be constructed with multiple refractive index layers without a microstructure. In the cross sectional view (FIG. 26B) and oblique view (FIG. 26C), both the first encapsulant 111 and the second encapsulant 121 are separately constructed with multiple refractive index layers in Babel Tower style. Also, the multiple refractive index layers construction has different refractive indices arranged in a decreasing fashion from lower layers to upper layers. It is contemplated that the second encapsulant 121 may also have microstructures on the top surface and/or at one interface between any layers.

Figure 27A:
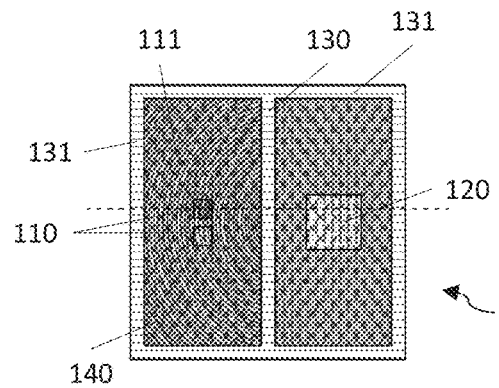
FIG. 27A-27C are schematic diagrams of a top view, cross-sectional view, and oblique sectional view, respectively, of an optical sensor module in accordance with an embodiment of the present disclosure.
Figure 27B:
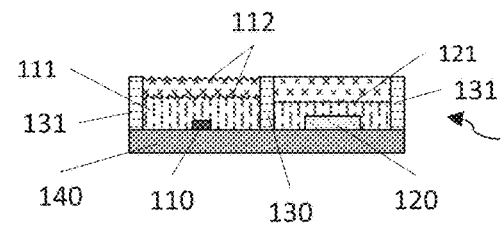
Figure 27C:
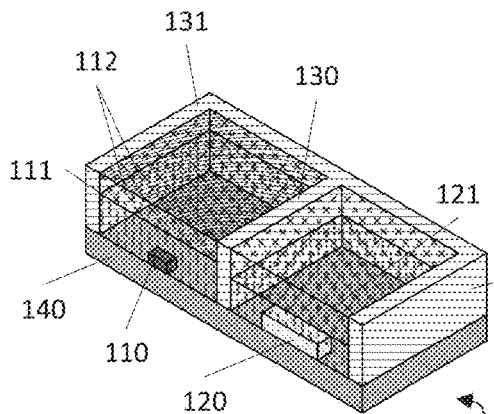

As illustrated in FIG. 27A, the first encapsulant 111 has multiple microstructures 112 formed as the top surface of the uppermost layer and formed as one interface of the adjacent layers inside, and the microstructure 112 is embodied as a set of concentric arcs concave toward the photodetector 120, while the second encapsulant 121 may be constructed with multiple refractive index layers without a microstructure. In the cross sectional view (FIG. 27B) and oblique view (FIG. 27C), both the first encapsulant 111 and the second encapsulant 121 are separately constructed of a stack of multiple layers in a pancake stack style, which features the flank sides of the multi-layer encapsulant abutting the packaging wall 131. Also, the multi-layer construction has different refractive indices arranged in a decreasing fashion from lower layers to upper layers.

Figure 28A:
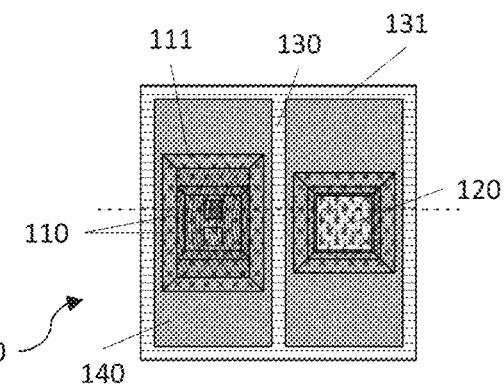
FIG. 28A-28C are schematic diagrams of a top view, cross-sectional view, and oblique sectional view, respectively, of an optical sensor module in accordance with an embodiment of the present disclosure.
Figure 28B:
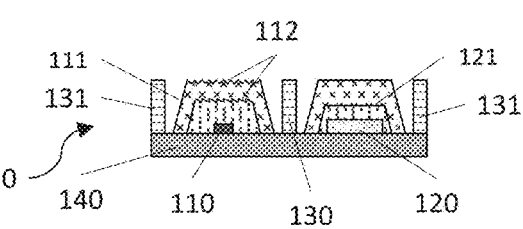
Figure 28C:
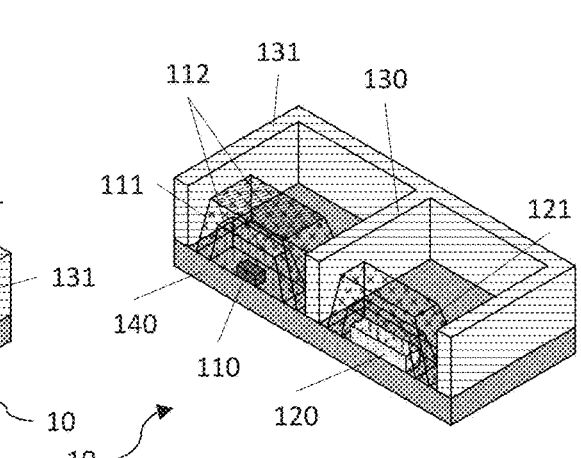

As illustrated in FIG. 28A, the first encapsulant 111 has multiple microstructures 112 formed as the top surface of the uppermost layer and formed as one interface of the adjacent layers inside, and the microstructure 112 is embodied as a set of concentric arcs concave toward the photodetector 120, while the second encapsulant 121 may be constructed with multiple refractive index layers without a microstructure. In the cross sectional view (FIG. 28B) and oblique view (FIG. 28C), both the first encapsulant 111 and the second encapsulant 121 are separately constructed of a stack of multiple layers in a cup-stacking style, which features the upper layer embracing the adjacent lower layer. Also, the multi-layer construction has different refractive indices arranged in a decreasing fashion from lower layers to upper layers.

In the examples of the present disclosure, the light source 110 is illustrated as two independent LEDs sealed in a first encapsulant 111, and the photodetector 120 may be a photodiode sealed in a second encapsulant 121. The first encapsulant 111 is constructed with multiple refractive index layers, and at least one interface of any two adjacent layers of the first encapsulant 111 is configured as a microstructure 112. Also, the second encapsulant 121 is constructed with multiple refractive index layers, and at least one interface of any two adjacent layers of the second encapsulant 121 is configured as a microstructure 122.

Figure 29A:
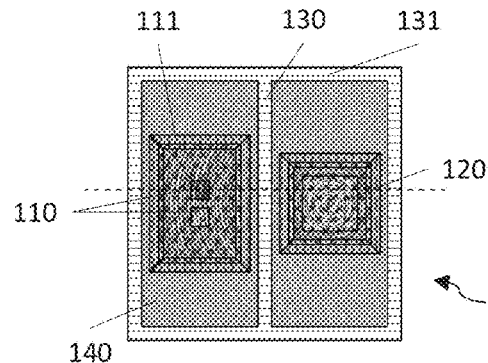
FIG. 29A-29C are schematic diagrams of a top view, cross-sectional view, and oblique sectional view, respectively, of an optical sensor module in accordance with an embodiment of the present disclosure.
Figure 29B:
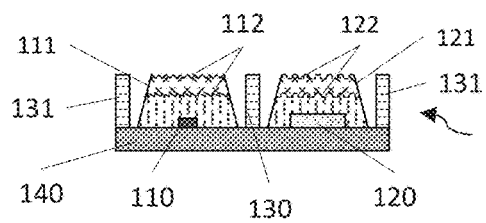
Figure 29C:
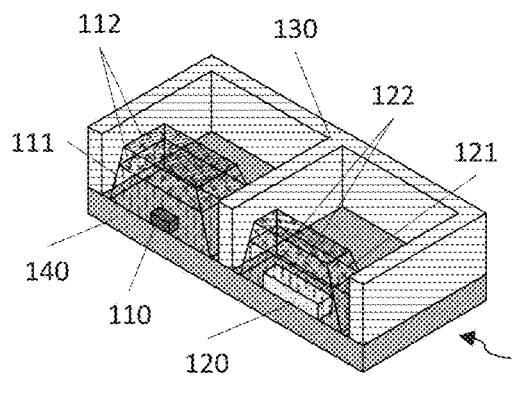

As illustrated in FIG. 29A, the first encapsulant 111 has multiple microstructures 112 formed as the top surface of the first encapsulant 111 and formed as one interface of the adjacent layers and the microstructure 112 is embodied as a set of concentric arcs concave toward the photodetector 120. Additionally, a photodiode is sealed in the second encapsulant 121 with multiple microstructures 122 formed as the top surface of the second encapsulant 121 and formed as one interface of the adjacent layers, and each microstructure 122 is embodied as a set of concentric circles. In the cross sectional view (FIG. 29B) and oblique view (FIG. 29C), both the first encapsulant 111 and the second encapsulant 121 are separately constructed of multiple refractive index layers in Babel Tower style. Also, the multi-layer construction has different refractive indices arranged in a decreasing fashion from lower layers to upper layers.

Figure 30A:
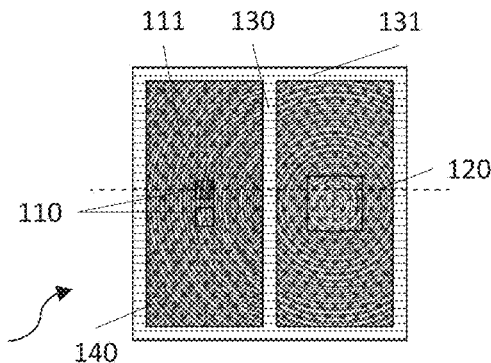
FIG. 30A-30C are schematic diagrams of a top view, cross-sectional view, and oblique sectional view, respectively, of an optical sensor module in accordance with an embodiment of the present disclosure.
Figure 30B:
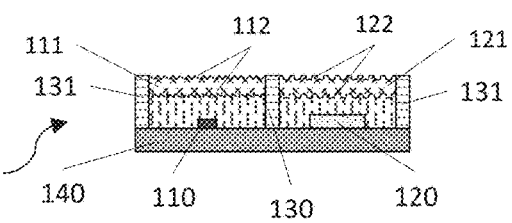
Figure 30C:
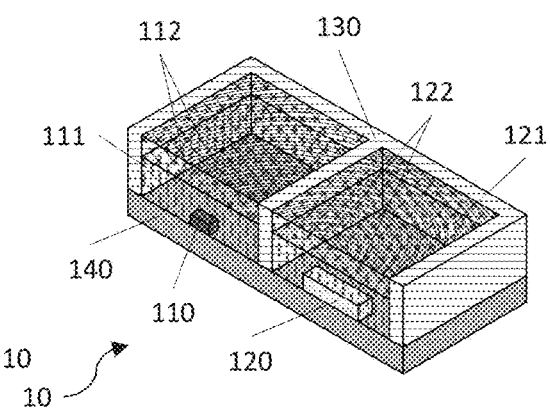

As illustrated in FIG. 30A, the first encapsulant 111 has multiple microstructures 112 formed as the top surface of the first encapsulant 111 and formed as one interface of the adjacent layers and the microstructure 112 is embodied as a set of concentric arcs concave toward the photodetector 120. Additionally, a photodiode is sealed in the second encapsulant 121 with multiple microstructures 122 formed as the top surface of the second encapsulant 121 and formed as one interface of the adjacent layers, and each microstructure 122 is embodied as a set of concentric circles. In the cross sectional view (FIG. 30B) and oblique view (FIG. 30C), both the first encapsulant 111 and the second encapsulant 121 are separately constructed with multiple refractive index layers in a pancake stack style.

Figure 31A:
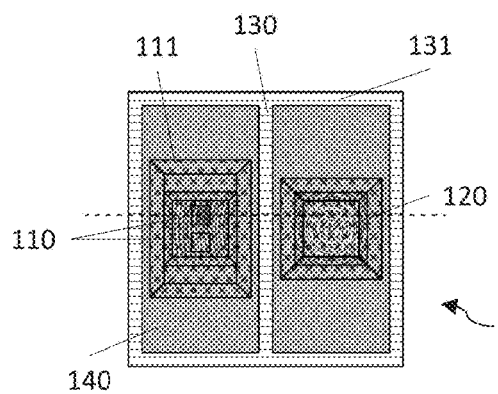
FIG. 31A-31C are schematic diagrams of a top view, cross-sectional view, and oblique sectional view, respectively, of an optical sensor module in accordance with an embodiment of the present disclosure.
Figure 31B:
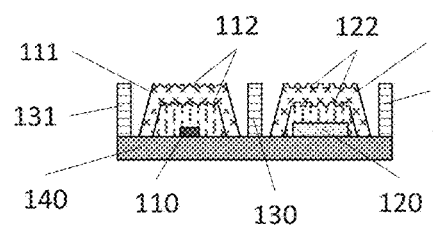
Figure 31C:
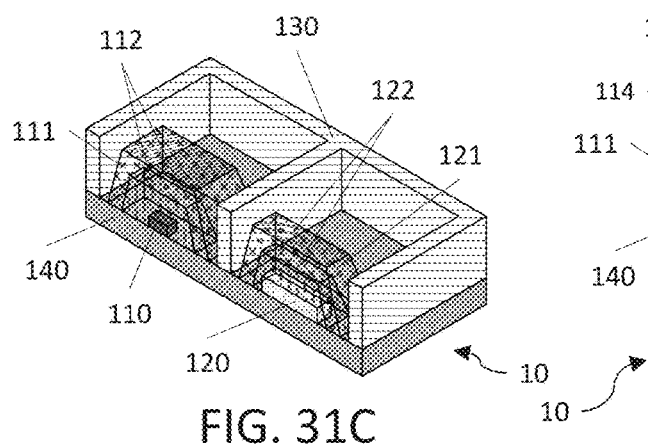

As illustrated in FIG. 31A, the first encapsulant 111 has multiple microstructures 112 formed as the top surface of the first encapsulant 111 and formed as one interface of the adjacent layers and the microstructure 112 is embodied as a set of concentric arcs concave toward the photodetector 120. Additionally, a photodiode is sealed in the second encapsulant 121 with multiple microstructures 122 formed as the top surface of the second encapsulant 121 and formed as one interface of the adjacent layers, and each microstructure 122 is embodied as a set of concentric circles. In the cross sectional view (FIG. 31B) and oblique view (FIG. 31C), both the first encapsulant 111 and the second encapsulant 121 are separately constructed with multiple refractive index layers in a cup-stacking style.

An optical directional component is a geometric optical component having a distinct refractive index from adjacent substances. Light refraction occurs when incident light travels through the refraction interface at an incident angle other than normal incidence. The refraction interface is a flat or curved plane and the inclined angle and the curvature of the plane is designed to meet the requirements. In one example, the optical directional component may be a curvature lens configured to direct the light path so that the SNR is further improved. The curvature lens may be configured at one interface of any adjacent layers in the encapsulant with multiple refractive index layer or may be configured on the top surface of an encapsulant. The shape of a curvature lens may be a parabolic plane, a spherical plane, or a polygonal plane.

Figure 32A:
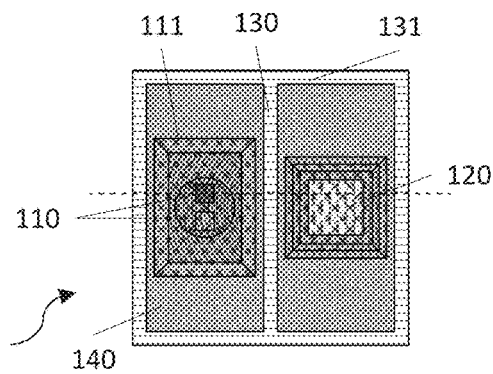
FIG. 32A-32C are schematic diagrams of a top view, cross-sectional view, and oblique sectional view, respectively, of an optical sensor module in accordance with an embodiment of the present disclosure.
Figure 32B:
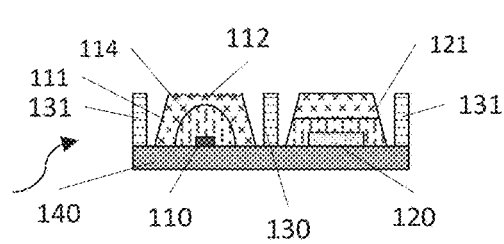
Figure 32C:
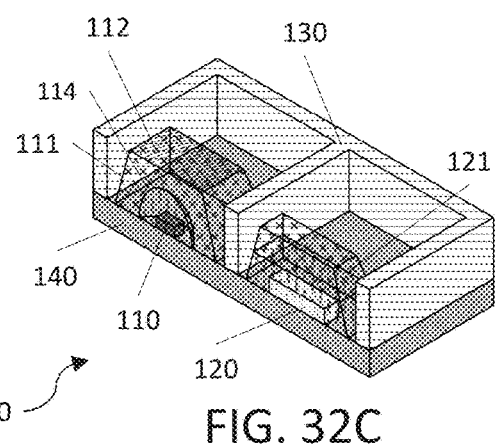

As illustrated in FIG. 32A, the first encapsulant 111 has the configurations as a microstructure 112 formed as the top surface of the uppermost layer. In addition, one interface of the first encapsulant 111 with multiple refractive index layers may be configured as a curvature lens 114. The microstructure 112 is embodied as a set of concentric arcs concave toward the photodiode and the curvature lens 114 is embodied as a parabolic surface concave to the light source 110, while a photodiode is sealed in the second encapsulant 121 without a microstructure. In the cross sectional view (FIG. 32B) and oblique view (FIG. 32C), the first encapsulant 111 is constructed with multiple refractive index layers in cup-stacking style and the second encapsulant 121 is constructed with multiple refractive index layers in Babel Tower style. Also, the multi-layer construction has different refractive indices arranged in a decreasing fashion from proximal layers to distal layers.

Figure 33A:
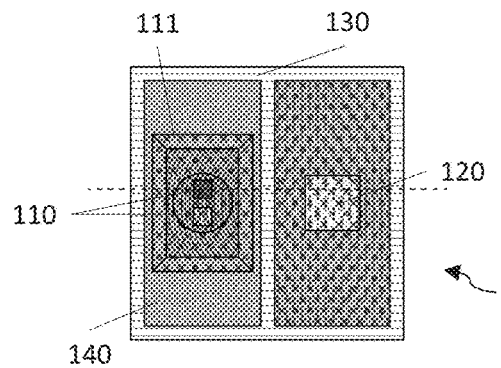
FIG. 33A-33C are schematic diagrams of a top view, cross-sectional view, and oblique sectional view, respectively, of an optical sensor module in accordance with an embodiment of the present disclosure.
Figure 33B:
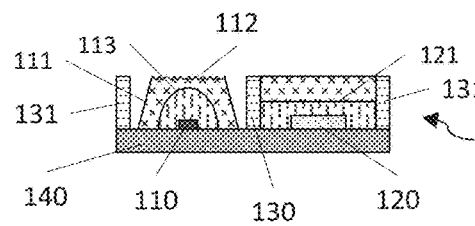
Figure 33C:
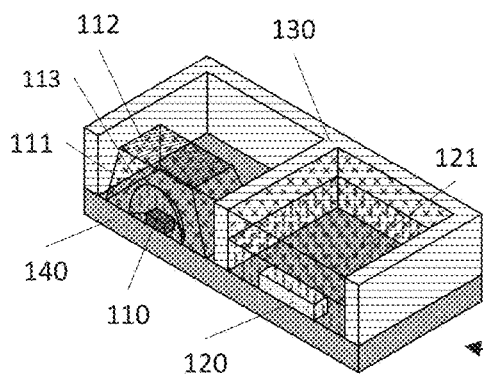

As illustrated in FIG. 33A, the first encapsulant 111 has the configurations as microstructure 112 formed as the top surface of the uppermost layer. In addition, one interface of the first encapsulant 111 with multiple refractive index layers may be configured as a curvature lens 114. The microstructure 112 is embodied as a set of concentric arcs concave toward the photodiode and the curvature lens 114 is embodied as a parabolic surface concave to the light source 110, while a photodiode is sealed in the second encapsulant 121 without a microstructure. In the cross sectional view (FIG. 33B) and oblique view (FIG. 33C), the first encapsulant 111 is constructed with multiple refractive index layers in cup-stacking style and the second encapsulant 121 is constructed with multiple refractive index layers in pancake stack style. Also, the multi-layer construction has different refractive indices arranged in a decreasing fashion from proximal layers to distal layers.

Figure 34A:
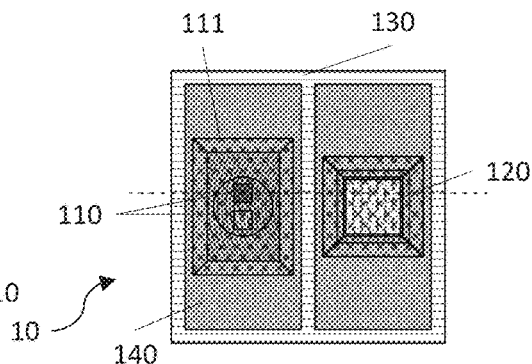
FIG. 34A-34C are schematic diagrams of a top view, cross-sectional view, and oblique sectional view, respectively, of an optical sensor module in accordance with an embodiment of the present disclosure.
Figure 34B:
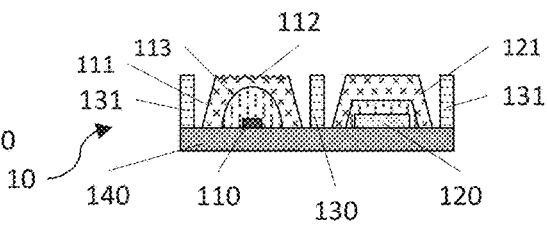
Figure 34C:
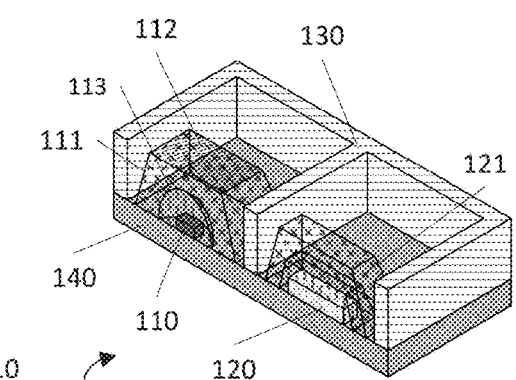

As illustrated in FIG. 34A, the first encapsulant 111 has the configurations as microstructure 112 formed as the top surface of the uppermost layer. In addition, one interface of the first encapsulant 111 with multiple refractive index layers may be configured as a curvature lens 114. The microstructure 112 is embodied as a set of concentric arcs concave toward the photodiode and the curvature lens 114 is embodied as a parabolic surface concave to the light source 110, while a photodiode is sealed in the second encapsulant 121 without a microstructure. In the cross sectional view (FIG. 34B) and oblique view (FIG. 34C), both the first encapsulant 111 and the second encapsulant 121 are separately constructed with multiple refractive index layers in a cup-stacking style. Also, the multi-layer construction has different refractive indices arranged in a decreasing fashion from proximal layers to distal layers.

Figure 35A:
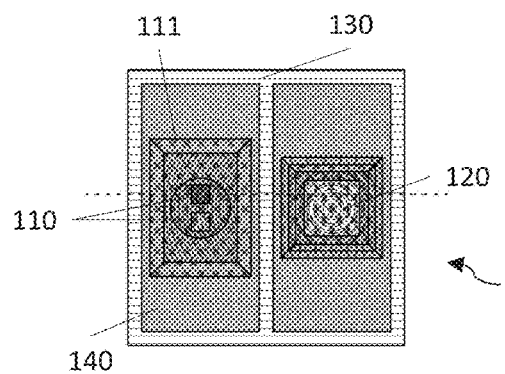
FIG. 35A-35C are schematic diagrams of a top view, cross-sectional view, and oblique sectional view, respectively, of an optical sensor module in accordance with an embodiment of the present disclosure.
Figure 35B:
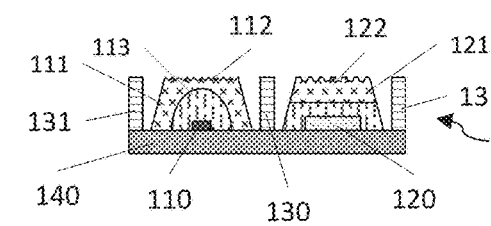
Figure 35C:
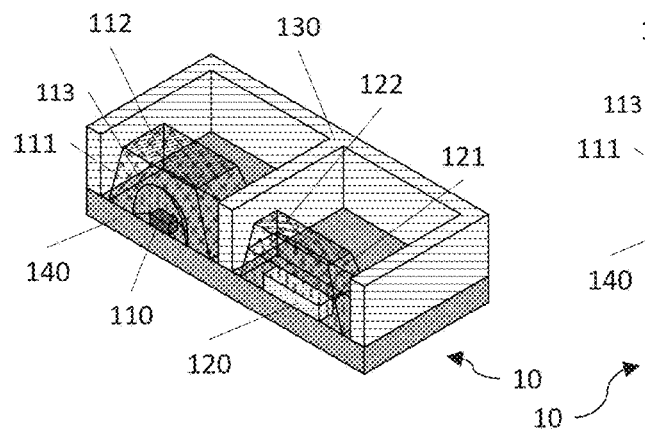

As illustrated in FIG. 35A, a photodiode is sealed in the second encapsulant 121 with a microstructure 122 formed as the top surface of the uppermost layer and the microstructure 122 is embodied as a set of concentric circles. In the cross sectional view (FIG. 35B) and oblique view (FIG. 35C), the second encapsulant 121 is constructed with multiple refractive index layers in Babel Tower style.

Figure 36A:
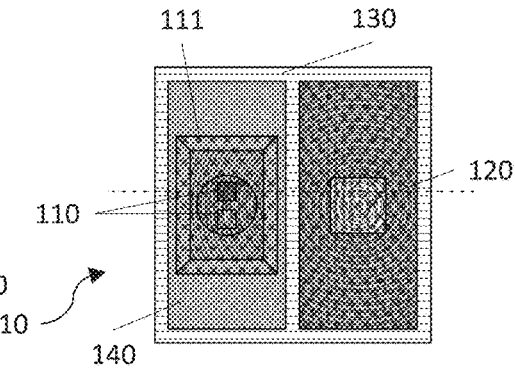
FIG. 36A-36C are schematic diagrams of a top view, cross-sectional view, and oblique sectional view, respectively, of an optical sensor module in accordance with an embodiment of the present disclosure.
Figure 36B:
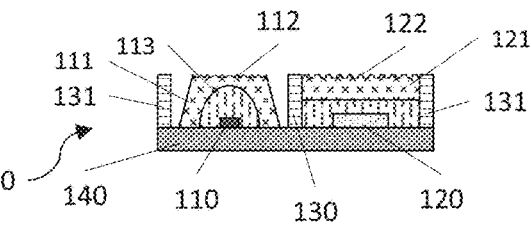
Figure 36C:
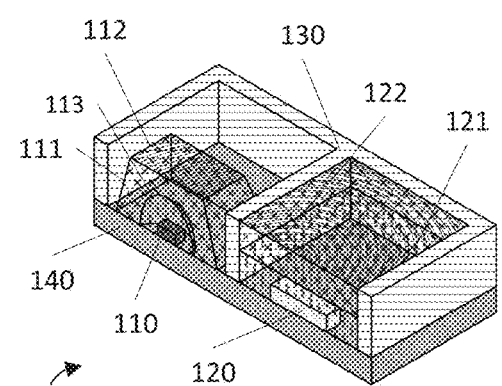

As illustrated in FIG. 36A, a photodiode is sealed in the second encapsulant 121 with a microstructure 122 formed as the top surface of the uppermost layer and the microstructure 122 is embodied as a set of concentric circles. In the cross sectional view (FIG. 36B) and oblique view (FIG. 36C), the second encapsulant 121 is constructed with multiple refractive index layers in pancake stack style.

Figures 37A, 38A:
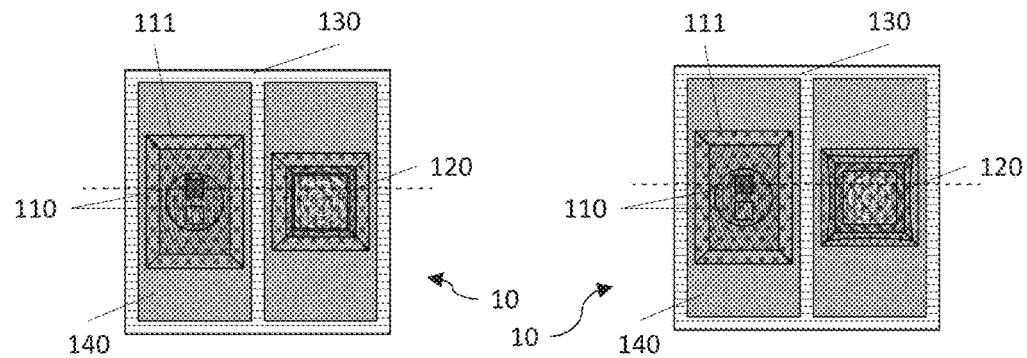
FIG. 37A-37C are schematic diagrams of a top view, cross-sectional view, and oblique sectional view, respectively, of an optical sensor module in accordance with an embodiment of the present disclosure.
FIG. 38A-38C are schematic diagrams of a top view, cross-sectional view, and oblique sectional view, respectively, of an optical sensor module in accordance with an embodiment of the present disclosure.
Figures 37B, 38B:
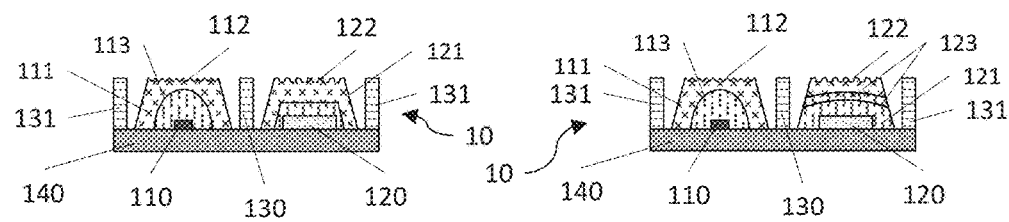
Figures 37C, 38C:
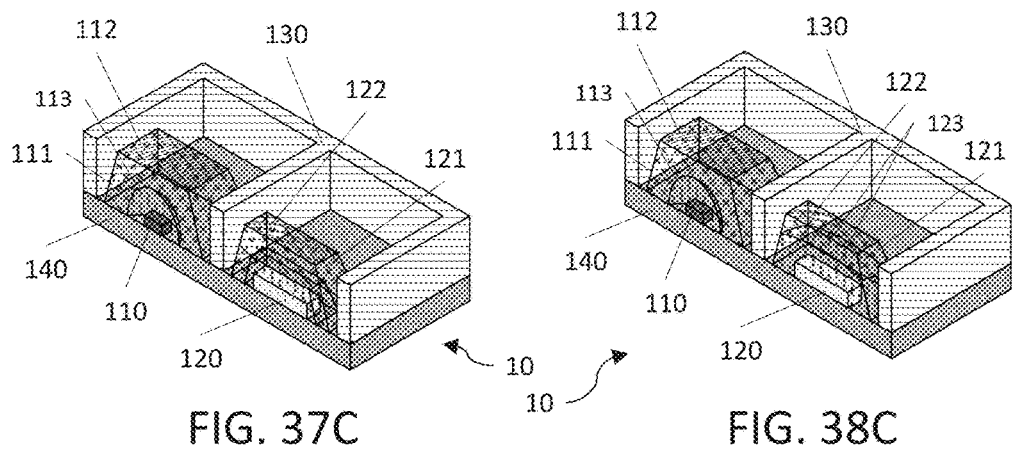

As illustrated in FIG. 37A, a photodiode is sealed in the second encapsulant 121 with a microstructure 122 formed as the top surface of the uppermost layer and the microstructure 122 is embodied as a set of concentric circles. In the cross sectional view (FIG. 37B) and oblique view (FIG. 37C), the second encapsulant 121 is constructed with multiple refractive index layers in a cup-stacking style.

In one example as shown in FIG. 38A, a photodiode is sealed in the second encapsulant 121 with a microstructure 122 formed as the top surface of the uppermost layer. In the example, the optical sensor module comprises optical directional components 123 disposed between the two adjacent refractive index layers, wherein the optical directional components are curvature lenses. Further, two curvature lenses 123 are configured in the second encapsulant 121. In the cross sectional view (FIG. 38B) and oblique view (FIG. 38C), the first encapsulant 111 is constructed with multiple refractive index layers in cup-stacking style and the second encapsulant 121 is constructed of a stack of multiple layers in Babel Tower style, where the curvature lenses 123 are embodied as parabolic plane concave to the photodiode.

In one embodiment of the present disclosure, the optical sensor modules 10 may further comprise a cover 150 distal to the first encapsulant 111 and/or the second encapsulant 121. The cover 150 serves as a contact interface between the object surface 190, such as a biological tissue surface or a skin surface, to increase the durability of the optical sensor module 10 and the consistency of measurement. As shown in FIG. 39A, the optical sensor modules 10 may also comprise a cover 150 in front of the first encapsulant 111 and the second encapsulant 121, and the cover 150 is located between the encapsulants and the object surface 190. With a slight press, the cover 150 provide an increased contact area with the object surface 190 to allow better optical reflection and diffusion. The cover 150 may be integrated as a part of the optical sensor module 10 or may be a part of the housing of the optical sensor device.

In addition, the internal surface or the external surface of the cover 150 may be coated with a thin film 151. The thin film 151 may be an anti-reflective or an anti-scratch thin film. As shown in FIG. 39B, the thin film 151 of external surface of the cover 150 is embodied as an anti-scratch thin film (such as polyethylene terephthalate, or silicon hard coating) and the one of the internal surface is embodied as an anti-reflective thin film.

The optical sensor modules 10 may also comprise a thin film 151 covering an encapsulant. With thin film technology, the SNR of the optical sensor module 10 may be further improved. The thin film 151 may be an anti-reflective thin film or a filter thin film. The anti-reflective thin film may be an index-matching film (for example, Rayleigh film) or an interference film to improve light extraction efficiency by reducing Fresnel reflection at the interface between different refractive indices. The filter thin film may be a long-pass filter, a short-pass filter, or a band-pass filter to clear down the full width at half maximum (FWHM) of the emitting light or filter out the noise from undesired wavelengths. Additionally, the anti-scratch thin film may be applied to prevent the signal loss caused by scratches.

As shown in FIG. 40A, both the surfaces of the first encapsulant 111 and the second encapsulant 121 are coated with a thin film 160. The thin film 160 of the first encapsulant 111 is embodied as an anti-reflective thin film (FIG. 40B) and the thin film 160 of the first encapsulant 111 is embodied as a band-pass filter thin film (FIG. 40C). The anti-reflective thin film improves the light extraction efficiency and the band-pass filter thin film reduces noise. It is contemplated that the thin film 160 of the first encapsulant 111 is embodied as a band-pass filter thin film and the thin film 160 of the first encapsulant 111 is embodied as an anti-reflective thin film, so that the FWHM of the emitting light has a clear cut-off wavelength and the photodiode detects the filtered signals within a specific window. In the application of the fluorescence detection long-pass filter thin film maybe applied to the second encapsulant 121 to acquire a clear fluorescent signal avoiding the excitation light. Also, the optical sensor module 10 may further comprise a cover 150 in front of the first encapsulant 111 and the second encapsulant 121. As shown in FIG. 41A, the optical sensor module 10 further comprises a cover 150 and the thin films 160 covering the encapsulants (FIGS. 41B and C).

Furthermore, the optical sensor module 10 may further comprise both a cover 150 coated with thin film 151 and the thin films 160 covering the encapsulants (FIG. 42A). As shown in FIG. 42B, the thin film 151 of external surface of the cover 150 is embodied as an anti-scratch thin film (such as polyethylene terephthalate, or silicon hard coating) and the one of the internal surface is embodied as an anti-reflective thin film. The thin film 160 of the first encapsulant 111 is embodied as an anti-reflective thin film (FIG. 42C) and the thin film 160 of the first encapsulant 111 is embodied as a band-pass filter thin film (FIG. 42D).

The optical sensor module 10 may have an optical directional component on the medial surface of the first encapsulant 111 or on the medical surface of the second encapsulant 121. The optical directional component may have an inclined plane or a curvature lens or the combination thereof. An inclined plane may have an inclined angle 315 between the surface of the encapsulant and the plane of the substrate. The inclined angle may be around ninety degrees to twenty degrees. In addition, a curvature lens may be configured in combination of an inclined plane. In one example, the curvature lens may have a radius of curvature with 0.6 millimeter and the inclined angle is about forty degrees when the partition has a height of 0.4 millimeter. Therefore, light emitted from the light source is more concentrated above the partition located between the light source and the photodetector, and less shed onto the partition 130.

Figure 43A:
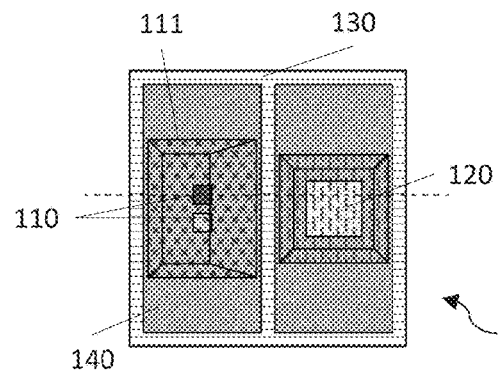
FIG. 43A-43C are schematic diagrams of a top view, cross-sectional view, and oblique sectional view, respectively, of an optical sensor module in accordance with an embodiment of the present disclosure.
Figure 43B:
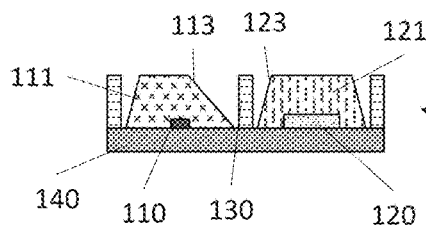
Figure 43C:
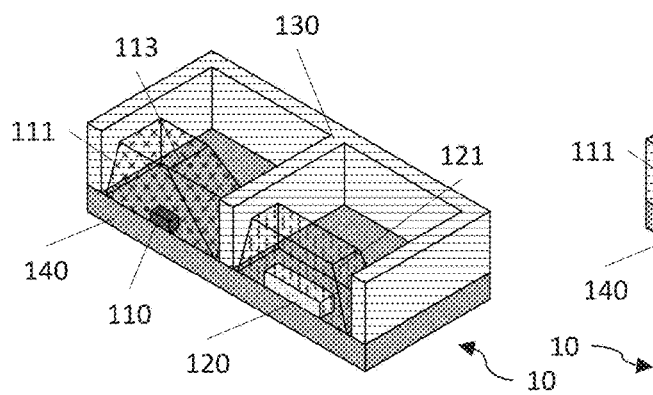

As illustrated in FIG. 43A, the medial surface of the first encapsulant 111 is configured as an optical directional component 113, and the optical directional component 113 is embodied as an inclined plane, while the photodetector 120 is sealed in the second encapsulant 121 with an inclined plane with a larger inclined angle. In the cross sectional view (FIG. 43B) and oblique view (FIG. 43C), both the first encapsulant 111 and the second encapsulant 121 are separately constructed in trapezoid shape. The optical directional component 113 of the medial surface of the first encapsulant 111 has an inclined angle smaller than the inclined angle of the second optical directional component 123.

Figure 44A:
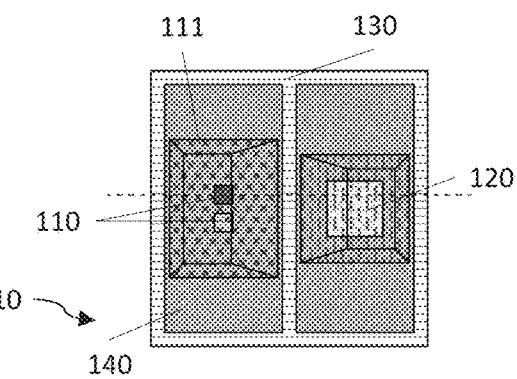
FIG. 44A-44C are schematic diagrams of a top view, cross-sectional view, and oblique sectional view, respectively, of an optical sensor module in accordance with an embodiment of the present disclosure.
Figure 44B:
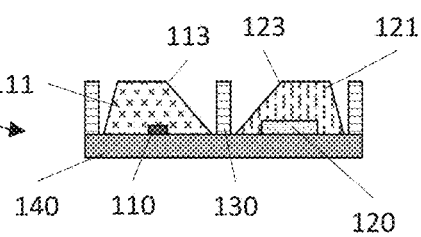
Figure 44C:
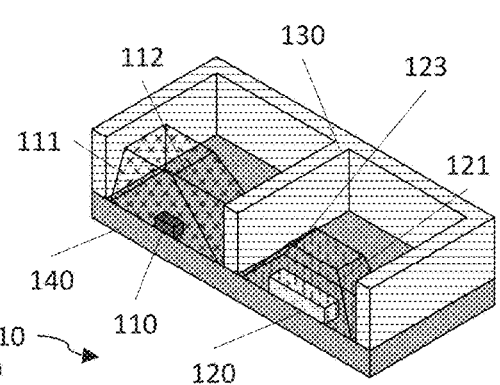

As illustrated in FIG. 44A, the medial surface of the first encapsulant 111 is configured as an optical directional component 113, and the optical directional component is embodied as an inclined plane. Additionally, the photodetector 120 is sealed in the second encapsulant 121 with an optical directional component 123 as an inclined plane. In the cross sectional view (FIG. 44B) and oblique view (FIG. 44C), both the first encapsulant 111 and the second encapsulant 121 are separately constructed in trapezoid shape. The first encapsulant 111 and the second encapsulant 121 has an inclined plane with an inclined angle to facilitate light extraction efficiency and light receiving efficiency, respectively. The inclined angle of the first optical directional component 113 may be different from the inclined angle of the second optical directional component 123.

Figure 45A:
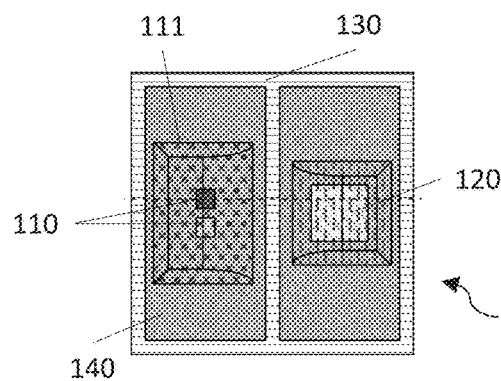
FIG. 45A-45C are schematic diagrams of a top view, cross-sectional view, and oblique sectional view, respectively, of an optical sensor module in accordance with an embodiment of the present disclosure.
Figure 45B:
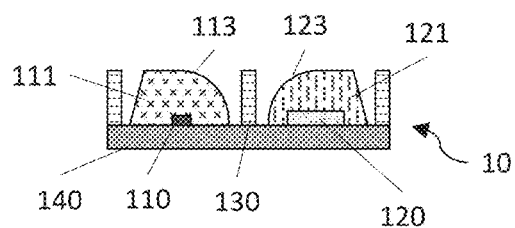
Figure 45C:
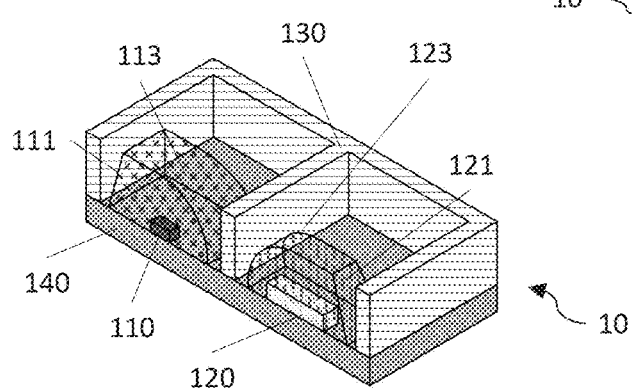

As illustrated in FIG. 45A-C, the medial surface of the first encapsulant 111 is configured as an optical directional component 113, and the optical directional component 113 is embodied as a curvature plane. Additionally, the photodetector 120 is sealed in the second encapsulant 121 with an optical directional component 123, which is embodied as a curvature plane. In the cross sectional view (FIG. 45B) and oblique view (FIG. 45C), both the first encapsulant 111 and the second encapsulant 121 are separately configured with a curvature plane on the medial surface. It is contemplated that the optical directional component of the second encapsulant 121 may differ from the one of the first encapsulant 111. For example, the first encapsulant may have a curvature plane on the medial surface, while the second encapsulant has an inclined plane.

Figure 46A:
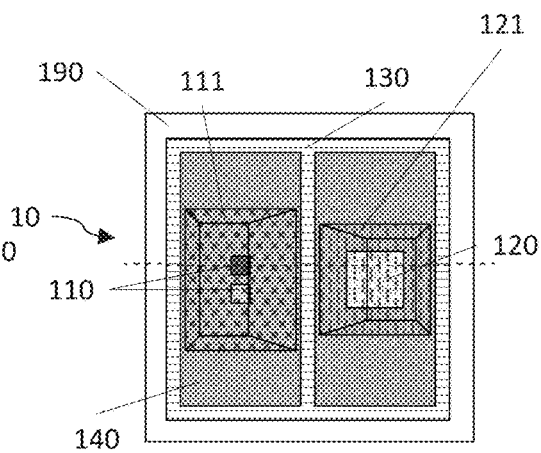
FIG. 46A-46B are schematic diagrams of a top view and cross-sectional view of an optical sensor module in accordance with an embodiment of the present disclosure.
Figure 46B:
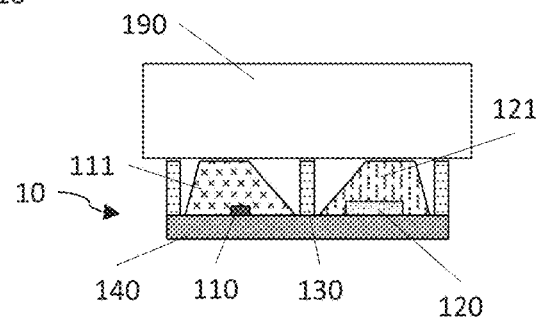

FIGS. 46-48 shows the situation of measuring the reflected light from an object surface 190 by the optical sensor module 10 with optical directional components, but other optical sensor modules within the present disclosure is also suitable for the application. The object surface 190 may be a surface of a biological tissue, such as skin or mucosa. The optical sensor module 10 is tolerable to various working conditions, such as rough object surface and relative motion between the sensor module and object surface. In FIGS. 46A and 46B, the top surface of the optical sensor module 10 may directly contact with the object surface 190. In FIGS. 47A and 47B, the upper side of the optical sensor module 10 may have a limited distance from the object surface 190 but the optical sensor module 10 is still capable of acquiring sufficient effective signals. In FIGS. 48A and 48B, a cover 150 may directly attach the object surface 190, and the optical sensor module 10 have a limited distance from the cover 150. The cover 150 may be a part of optical sensor module 10 or be integrated with a housing of an optical sensing accessory or an optical sensing device. The material of the cover may be selected from organic glass, such as PMMA or PC, or inorganic glass such as silicate glass or silicone compound. In addition, the internal surface or the external surface of the cover 150 may be coated with a thin film. The thin film may be an anti-reflective (such as index-matching thin film or interference thin film) or an anti-scratch thin film (such as polyethylene terephthalate, or silicon hard coating). Furthermore, the optical sensor module 10 may further comprise a thin film covering an encapsulant. With thin film technology, the SNR of the optical signals may be further improved. The thin film may be an anti-reflective thin film or a filter thin film. The anti-reflective thin film may be an index-matching film (for example, Rayleigh film) or an interference film to improve light extraction efficiency by reducing Fresnel reflection at the interface between the encapsulants and the environmental medium. The filter thin film may be a long-pass filter, a short-pass filter, or a band-pass filter to clear down the full width at half maximum (FWHM) of the emitting light or filter out the noise from undesired wavelengths.

Furthermore, a cover 150 may be coupled to the partition 130 and the packaging wall 131 enclosing the first encapsulant 111 and the second encapsulant 121. The cover may have surface configurations, such as a microstructure, a curvature lens, or the combination thereof. The cover may have tight connection to the packaging wall 131 to have good protection from ambient moisture, water, or dusts.

Figures 49A, 50A:
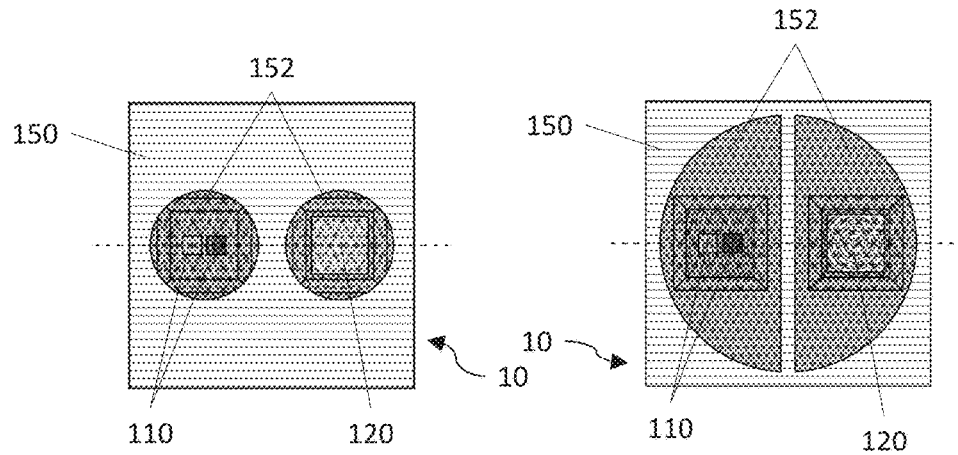
FIG. 49A-49C are schematic diagrams of a top view, cross-sectional view, and oblique sectional view, respectively, of an optical sensor module comprising a cover in accordance with an embodiment of the present disclosure.
FIG. 50A-50C are schematic diagrams of a top view, cross-sectional view, and oblique sectional view, respectively, of an optical sensor module comprising a cover in accordance with an embodiment of the present disclosure.
Figures 49B, 50B:
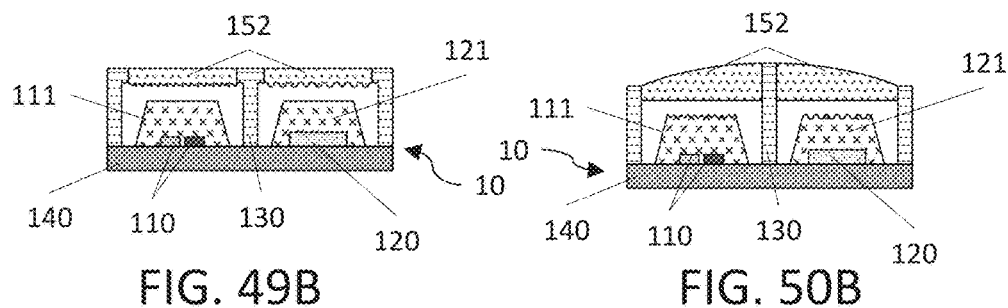
Figures 49C, 50C:
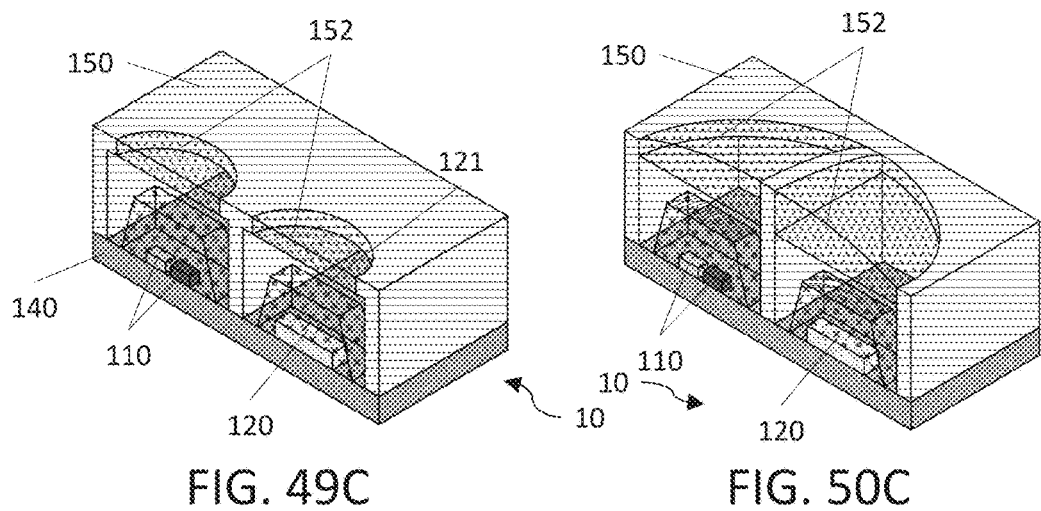

In FIG. 49A-C, the cover 150 is configured with a planar surface with a microstructure on the inner surface of the cover 150. In FIG. 49A, the cover comprises two optical transparent windows 152 and each window is located beyond the first encapsulant 111 or the second encapsulant 121. In FIGS. 49B and 49C, the cover comprises two microstructures on the inner surface of the optical transparent windows 152.

In FIG. 50A-C, the cover 150 is configured with a curvature lens on the surface of the cover 150. In FIG. 50A, the cover comprises two semicircular optical transparent windows 152 and each window is located beyond the first encapsulant 111 or the second encapsulant 121. In FIGS. 50B and 50C, the cover 150 comprises two plano-convex lens on the surface of the optical transparent windows.

In FIG. 51A-C, the cover 150 is configured with a curvature lens on the outer surface of the cover 150 and a microstructure on the inner surface of the cover 150. In FIG. 51A, the cover comprises two semicircular optical transparent windows 152 and each window is located beyond the first encapsulant 111 or the second encapsulant 121. In FIGS. 51B and 51C, each optical transparent window has a plano-convex lens on the outer surface and a microstructure on the inner surface.

In FIG. 52A-C, the cover 150 is configured with a curvature lens on the surface of the cover 150. In FIG. 52A, the cover comprises two optical transparent windows 152 and each window is located beyond the first encapsulant 111 or the second encapsulant 121. In FIGS. 52B and 52C, the optical transparent window on the light source side has a plano-convex lense and the optical transparent window on the light source side has a plano-concave lense.

In FIG. 53A-C, the cover 150 is configured with a curvature lens on the outer surface of the cover 150 and a microstructure on the inner surface of the cover 150. In FIG. 53A, the cover comprises two optical transparent windows 152 and each window is located beyond the first encapsulant 111 or the second encapsulant 121. In FIGS. 53B and 53C, the optical transparent window on the light source side has a plano-convex lense and the optical transparent window on the light source side has a plano-concave lense. Both the plano-convex lense and the plano-concave lense further comprise microstructures on the inner surface of the cover 150.

In FIG. 54A-C, the cover 150 is configured with a curvature lens on the surface of the cover 150. In FIG. 54A, the cover 150 comprises two optical transparent windows 152 and each window is located beyond the first encapsulant 111 or the second encapsulant 121. In FIGS. 54B and 54C, each of the optical transparent windows has a meniscus lense.

An optical sensor module may further comprise a microcontroller, an analogue front end, an operational amplifier, a light source driver or the combination thereof. A microcontroller is an integrated circuit chip configured to trigger the emittance of the light sources or to process the signals received from the photodetectors. An analogue front end is configured to receive and process the analogue signals from the photodetectors. The microcontroller and analogue front end may have a function of analogue to digital signal conversion. An operational amplifier is configured to receive and process the analogue signals from the photodetectors. An operational amplifier can amplify at least a part of the signals to achieve signal augmentation, filtering, or noise reduction. A light source driver is configured to control the electrical current flow through the light source, such as LED or laser diode. The electrical connections between an analogue front end, a microcontroller, an operational amplifier, a light source driver, the light source and the photodetectors may be coupled through the circuit printed within the substrate.

Figure 55A:
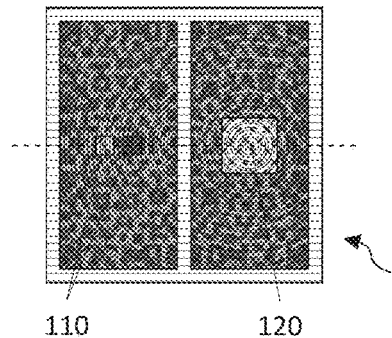
FIG. 55A-55C are schematic diagrams of a top view, cross-sectional view, and oblique sectional view, respectively, of an optical sensor module comprising an analogue front end in accordance with an embodiment of the present disclosure.
Figure 56A:
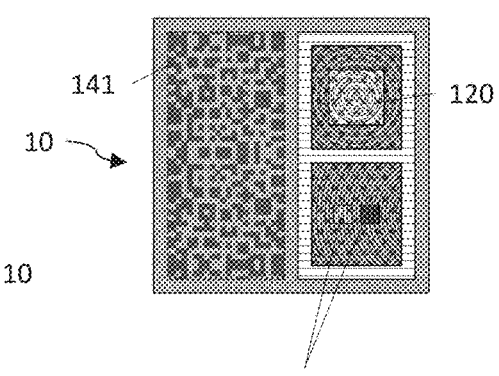
FIG. 56A-56B are schematic diagrams of a top view and oblique view, respectively, of an optical sensor module comprising an analogue front end in accordance with an embodiment of the present disclosure.
Figure 55B:
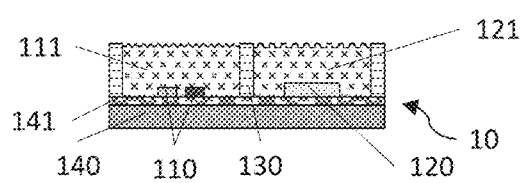
Figure 56B:
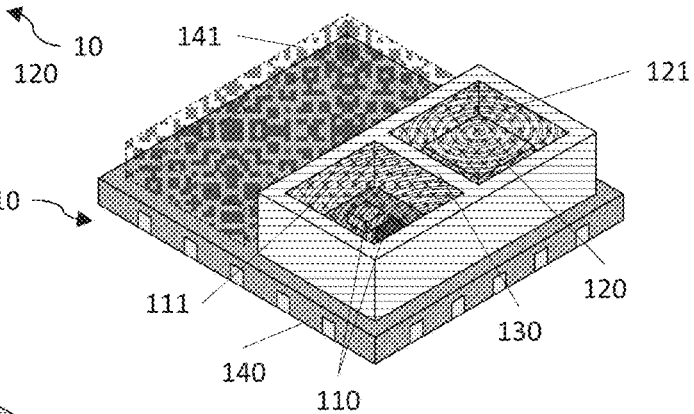
Figure 55C:
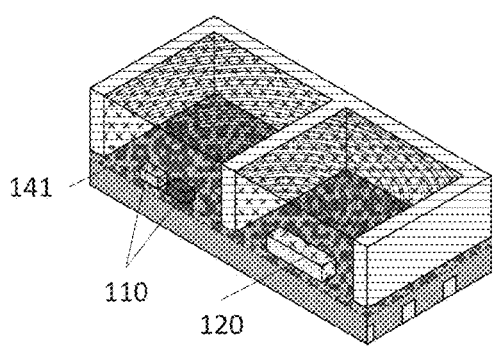

In FIG. 55A-C, an optical sensor module has an analogue front end 141 between the encapsulants and the substrate to receive the signals from a photodetector 120. The analogue front end can be integrated as a part of the substrate 140 and have electrical connection to the photodetector 120. In FIGS. 56A and 56B, an optical sensor module has an analogue front end 141 beside the encapsulants separated by the packaging walls.

In FIGS. 57A and 57B, an optical sensor have two light sources 110, a photodetector 120, a partition 130, the packaging walls 131, a microcontroller 142 and an analogue front end 141 beside the encapsulants separated by the packaging walls 131. The microcontroller 142 and the analogue front end 141 may have electrical connections to each other and to the photodetectors 120.

In FIGS. 58A and 58B an optical sensor module have a light source 110, four photodetectors 120, a partition 130, a microcontroller 142 and an analogue front end 141. A microcontroller 142 and an analogue front end 141 are separately located between the two second encapsulants 121 and beside the partition 130. The analogue front end may have electrical connections to the photodetectors 120 and the microcontroller 142 has electrical connections of the analogue front end 141 to receive the signals processed by the analogue front end 141 from the photodetectors 120. In FIGS. 59A and 59B sensor have a light source 110, four photodetectors 120, a partition 130, a microcontroller 142 and three analogue front ends 141. The microcontroller 142 and the three analogue front ends 141 are separately located between the two second encapsulants 121 and beside the partition 130.

In FIGS. 60A and 60B an optical sensor module has a light source 110, four photodetectors 120, a partition 130, a microcontroller 142, an operational amplifier 143 and a light source driver 144. The microcontroller 142, the operational amplifier 143 and the light source driver are separately located between the two second encapsulants 121 and beside the partition 130. The light source driver 144 is connected to the light source 110 to control the emitting frequency, duration, or intensity. The operational amplifier may have electrical connections to the photodetectors to augment the photocurrent and the microcontroller connects to the operational amplifier to receive the signals processed by the operational amplifier.

An optical sensor module 10 may be a multi-directional optical sensor module 5. In some examples, the multi-directional optical sensor module 5 is a bi-directional sensor module 5. The bi-directional optical sensor module 5 is manufactured to emit light and detect the reflected light from two directions, and the received reflected light will be proportionally transduced into electrical current. Bi-directional sensor module 5 comprises a light source 110, a first encapsulant 111 over the light source 110, two photodetectors 120, wherein all mentioned above are mounted on a substrate 140. Each photodetector 120 is covered by a second encapsulant 121 and both second encapsulants 121 are covered by the first encapsulant 111. The bi-directional optical sensor module 5 may be fabricated in a single compact package. Using the two photodetectors 120, the bi-directional optical sensor module 5 may detect light from different parts of body for various applications. It is also contemplated that the bi-directional optical sensor module 5 may employ a discrete light source 110 and a photodetector 120 that are separately packaged and mounted to one or more printed circuit boards (also referred to as "PCB") depending on various design requirements. In addition, the light source may comprise an array of LEDs or a plurality of LEDs, while each photodetector may comprise an array of photodiodes or a plurality of photodiodes.

The construction of the encapsulants features a light splitting and light extraction design for the first encapsulant 111 and a light collection design for the second encapsulants 121. The first encapsulant 111 and the second encapsulants 121 may have the refractive index mediating the optoelectronics and the environment. There are two second encapsulants 121 located on the two sides of the light source 110. More specifically, the first encapsulant 111 has a predetermined shape for splitting the light from the light source 110 into two beams of light in different directions and for guiding them to the object surface under test; the first encapsulant 111 seals the light source 110 and also covers the two second encapsulants 121 sealing the photodetectors 120. The first encapsulant 111 may take advantage of total internal reflection of the emitted light by a difference in the refractive index or a predetermined curvature, or the first encapsulant 111 may be covered with the reflective coating 180 confining the emitted light. Each of the second encapsulants 121 may have a predetermined shape for collecting the light reflected from the objects. For example, the second encapsulants are substantially prismatic or quadrispherical. Furthermore, the two second encapsulants 121 may be engineered as a symmetric or an asymmetric shape, and also the first encapsulant 111 may have various shapes for specific requirements. For example, the top surface of the first encapsulant 111 may be two inclined planes intersecting substantially above the light source 110 or may be two shallow curved plane intersecting substantially above the light source 110.

A coating may be disposed on different surfaces of the encapsulants for blocking the stray light directly from the light source 110 to the photodetector 120 or guiding/collecting the light to/from the objects. The coating may be a thin film of metal or a reflective material (for example Ag or TiO2 riched compound).

Figure 61A:
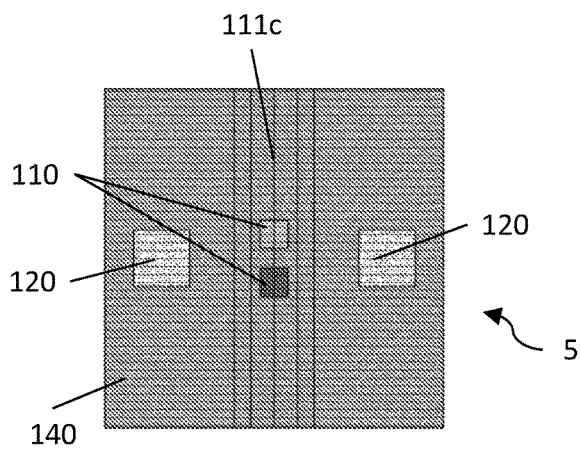
FIG. 61A-61C are schematic diagrams of a top view, cross-sectional view, and oblique sectional view, respectively, of an optical sensor module in accordance with an embodiment of the present disclosure.
Figure 61C:
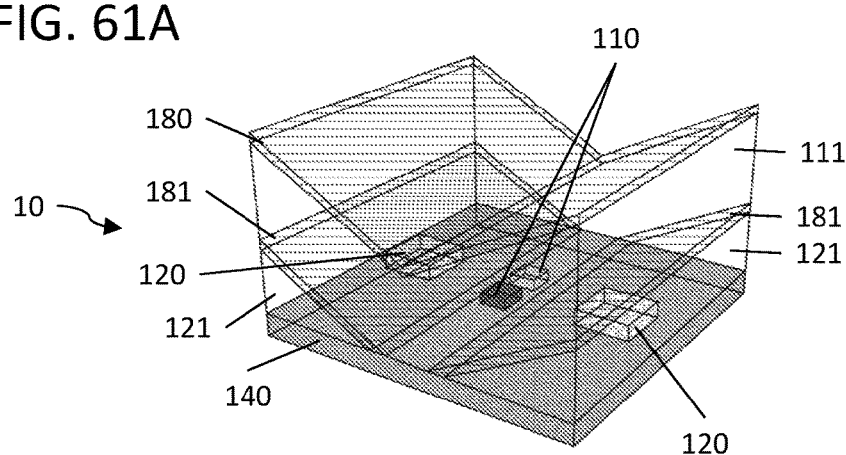
Figure 61B:
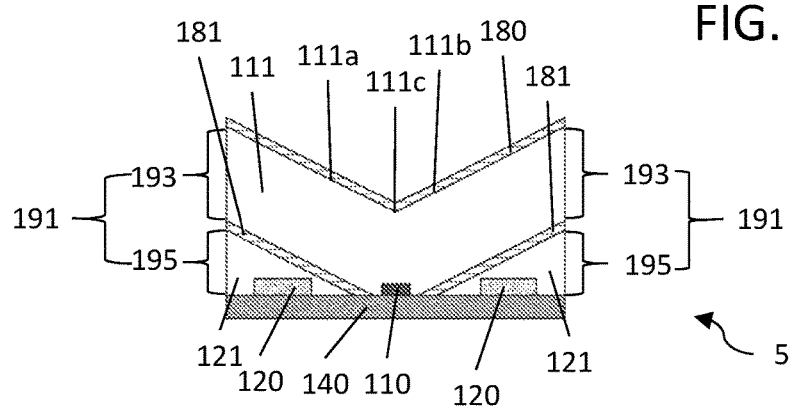

The contact surfaces 191 (one example as shown in FIG. 61B) are the openings for the emitted (the first encapsulant 111) and reflected (the second encapsulant 121) light and are used to attach the objects, while the side surfaces are the surface shown in the cross sectional view and the contralateral surface. As shown in FIG. 61B, the contact surfaces 191 includes first side surfaces 193 of the first encapsulant 111 and second contact surfaces 195 of the second encapsulant 121, wherein these side surfaces are substantially perpendicular to the substrate 140 and opposite to the light source 110. At least part of the contact surface of the encapsulants may be formed as a microstructure. For example, the first encapsulant 111 includes a microstructure 112 formed as the contact surface of the first encapsulant 111. The encapsulant 111 with microstructure(s) enhances the signal strength because the light is concentrated toward intended direction from the light source 110 toward the photodetector 120, while the light passes through the microstructure 122 of the encapsulant 121.

A wall may be also be disposed on the side surfaces, of the encapsulants for blocking the stray light formed of opaque material, which blocks via reflection and/or absorption in the specific spectrum of wavelengths emitted by the light source 110, for noise reduction.

The bi-directional optical sensor module 5 is a compact packaged module comprising of a light source 110, a photodetector 120, a first and two second encapsulants 121, and a substrate 140. The primary goal of the present technology is to be capable of measuring two directions of the reflected optical signals by specific shapes of the encapsulants. These shapes also improve the performance of the bi-directional optical sensor module 5 achieved by enhancing the light extraction efficiency, directing the light path, or reducing the stray light. Other modification and further application without departing the scope of disclosure are presented in the embodiments. It may be embodied as the simple composition with one light emitting diode (LED) and two silicon photodiodes all mounted on a printed circuit board as a substrate 140. Both LED and silicon photodiode are hermetically sealed, separately, with epoxy encapsulants. In the example for measuring oxygenation of biological tissue, both wavelengths in infrared and red regions are required. Therefore, one red LED and one infrared LED may be mounted on the same sensor module 5. In other implementations that are within the scope of the present disclosure, the number and the arrangement of the light sources 110 and photodetectors 120 may be modified.

As shown in FIG. 61-69, the general construction of the bi-directional optical sensor module 5 is presented. The bi-directional optical sensor module 5 comprises two LEDs and two silicon photodiodes, wherein both are mounted on a substrate 140 and the two silicon photodiodes are located on two opposite sides of the two LEDs. The first encapsulant 111 covers the light source 110, while the two second encapsulants 121 cover the two photodiodes 120, therefore the two second encapsulants 121 are located on two opposite sides of the two LEDs as well. In the embodiments, an encapsulant may have modifications in configuration and construction. For example, the configuration of the first encapsulant 111 may be trapezoid shape or cylindrical shape. In addition, the contact surfaces of the first encapsulant 111 are configured with a first microstructure 112, and the contact surfaces of the second encapsulants 121 may have a second microstructure 122.

In the examples of the present disclosure, as shown in FIGS. 61-68, a second coating 181 is disposed on the top surface of the second encapsulants 121 to reduce light leakage directly from the light source to the photodetector and reduce the effect of ambient stray light. In FIGS. 61-65, the first coating 180 is disposed on the surface of the first encapsulant 111 to limit light leakage and thus enhance the light emitting toward the contact surfaces. The surface of both encapsulants have a predetermined surface configuration to enhance SNR. For example in FIG. 61B, the top surface of the first encapsulant may be formed as two inclined plane 111a, 111b intersecting at around the above of the light source 110 and formed as an intersected line 111c as shown in FIG. 61A. In the examples, each of the inclined planes is about parallel to the surface plane of the second encapsulant on the same side. In some examples, the inclined planes 111a, 111b may have asymmetric shape or size, and may have cylindrical shape. For ease of presentation, the first coating 180 is disposed on the top surface of the first encapsulant 111, and the second coating 181 is the disposed on the top surface of the second encapsulant 121. Further, the first encapsulant 111 has refractive index, $n_1$ and the two second 121 encapsulants have refractive indices, $n_2$, wherein $n_1$ and $n_2$ may be different.

The top surfaces of the first encapsulant 111 and the two second encapsulants 121 have a predetermined tilting angle or curvature; therefore, more emitted light is extracted from the LEDs and more reflected light is collected to the photodiodes to enhance effective signal strength.

As illustrated in the top view (FIG. 61A), the substrate 140 area is divided into three regions by two straight lines; one rectangular area enclosing the LEDs and two rectangular areas, on the two sides of the LEDs, enclosing the two photodiodes. In the cross sectional view (FIG. 61B) and the oblique view (FIG. 61C), the two second encapsulants 121 are adjacent to the light source 110. The two second encapsulants 121 are embodied as a shape of a triangle prism, horizontally disposed on two rectangular areas respectively and sealing the two photodiodes. Additionally, the first encapsulant 111 is embodied as a shape of two side-by-side trapezoid prisms, and horizontally disposed on two second encapsulants 121 and sealing the LEDs. In addition, there is the first coating 180 on the first encapsulant 111 and the second coating 181 on the second encapsulants 121. The two second encapsulants 121 are constructed together or separately with their top surfaces are covered by the second coating 181; then the first encapsulant 111 are constructed on top of the two second encapsulants 121 with its top surface is covered by the first coating 180.

Figures 62A, 62C:
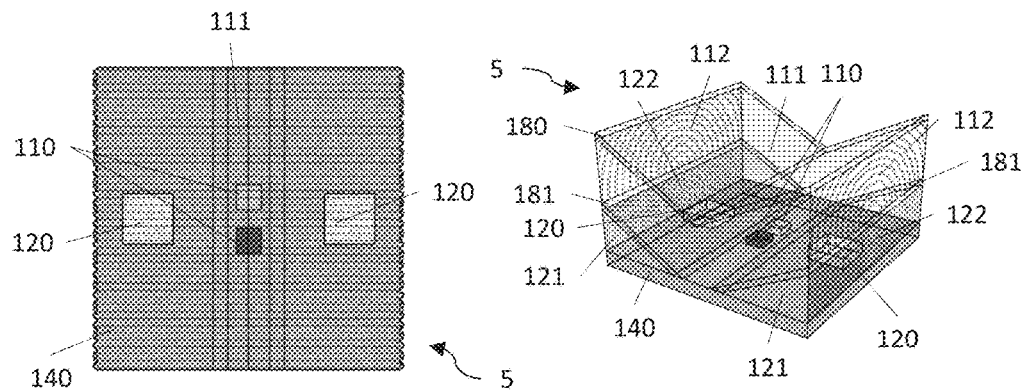
FIG. 62A-62C are schematic diagrams of a top view, cross-sectional view, and oblique sectional view, respectively, of an optical sensing module in accordance with an embodiment of the present disclosure.
Figures 62B, 62D:
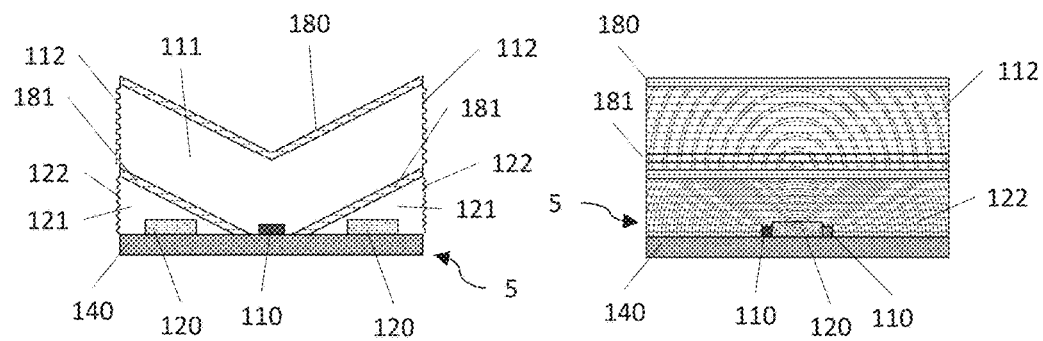
FIG. 62D is the side view of an optical sensor module from the side of contact surface.
Figure 64A:
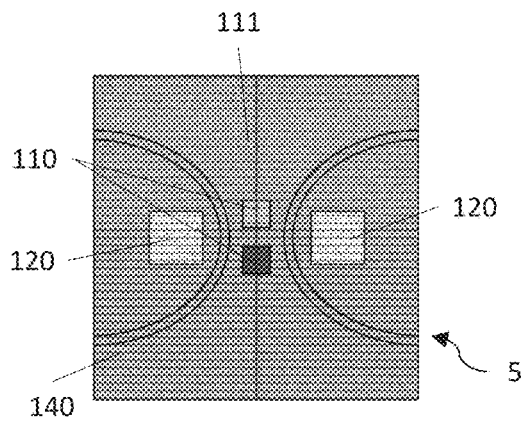
FIG. 64A-64C are schematic diagrams of a top view, cross-sectional view, and oblique sectional view, respectively, of an optical sensor module in accordance with an embodiment of the present disclosure.
Figure 64C:
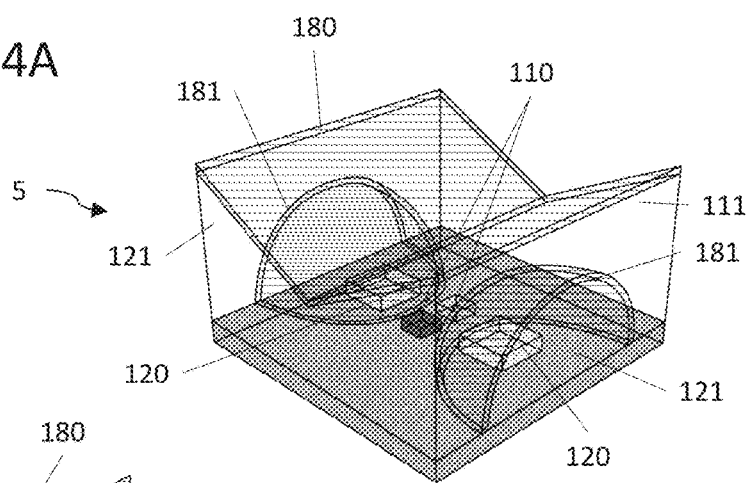
Figure 64B:
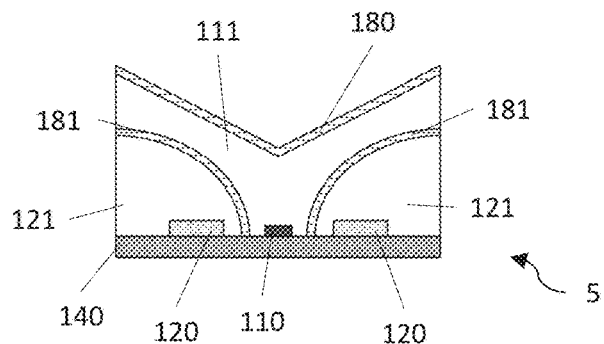
Figure 66A:
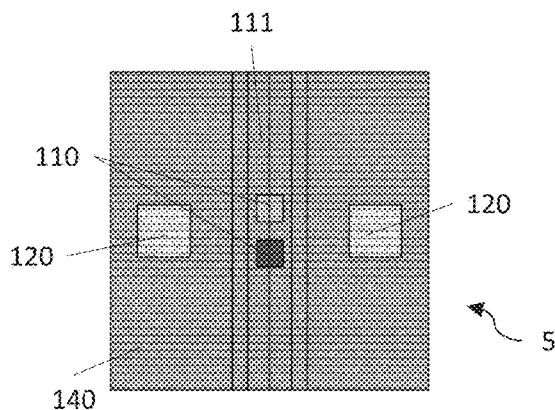
FIG. 66A-66C are schematic diagrams of a top view, cross-sectional view, and oblique sectional view, respectively, of an optical sensor module in accordance with an embodiment of the present disclosure.
Figure 66C:
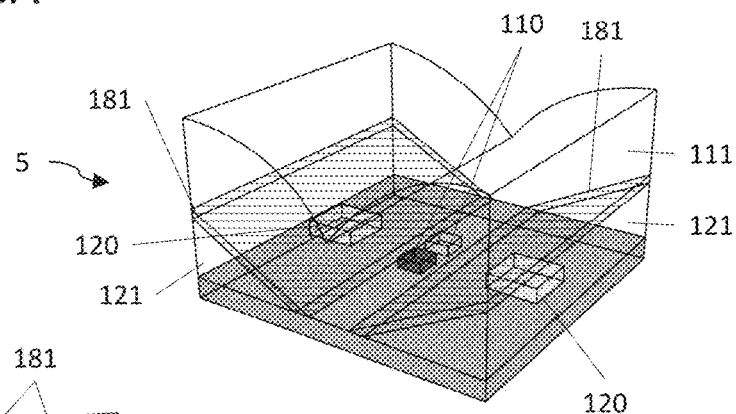
Figure 66B:
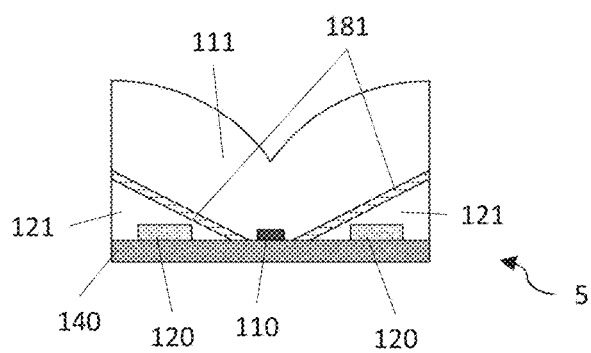
Figure 67A:
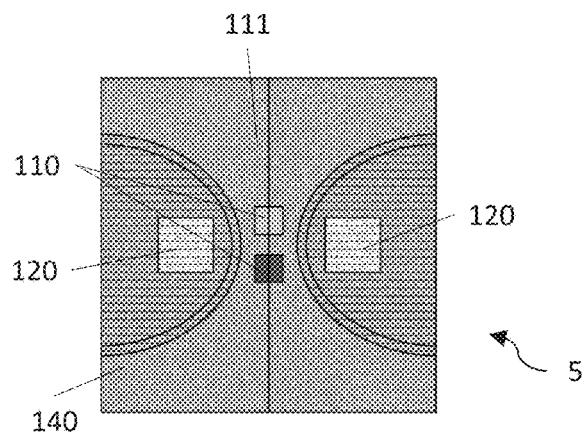
FIG. 67A-67C are schematic diagrams of a top view, cross-sectional view, and oblique sectional view, respectively, of an optical sensor module in accordance with an embodiment of the present disclosure.
Figure 67C:
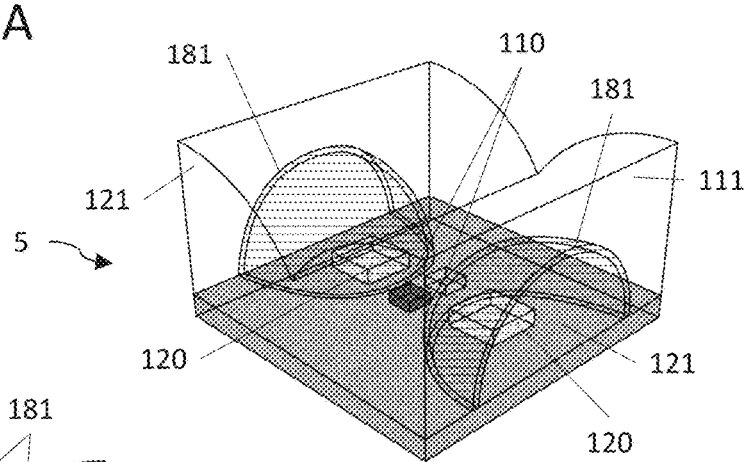
Figure 67B:
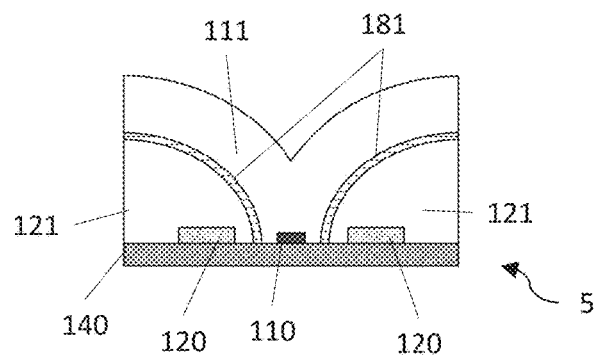

In the top view (FIG. 62A) and the cross sectional view (FIG. 62B), the two second encapsulants 121 are embodied as a shape of a triangle prism, horizontally disposed on two rectangular areas respectively and sealing the two photodiodes. Additionally, the first encapsulant 111 is embodied as a shape of two side-by-side trapezoid prisms, and horizontally disposed on two second encapsulants 121 and sealing the LEDs. It is contemplated that the contact surfaces of the first 111 and second 121 encapsulants may be formed as different microstructures (for example, DOEs or Fresnel patterns as shown in FIGS. 62C and 62D) to enhance the light extraction/receiving efficiency. For example, the first microstructures are configured in a set of concentric arcs with wider intervals than the second microstructures.

In the top view (FIG. 63A) and the cross sectional view (FIG. 63B), the two second encapsulants 121 are embodied as a shape of a triangle prism, horizontally disposed on two rectangular areas respectively and sealing the two photodiodes. Additionally, the first encapsulant 111 is embodied as a shape of two asymmetric side-by-side trapezoid prisms, and horizontally disposed on two second encapsulants 121 and sealing the LEDs. It is also contemplated that the configuration (for example the inclined angle of top surfaces) and the material (for example refractive index) of the two second encapsulants 121 and the coatings 181 may differ from each other. In FIG. 63B, the distance between the light source 110 to the contact surface, d1, is shorter than the distance between the light source 110 to the opposite contact surface, d2. The two tilting angles, θ1 and θ2, of the top surface of the first encapsulant may be different. For example, asymmetric second encapsulants 121 resulting in an asymmetric first encapsulant 111. In addition, the contact surfaces of the first 111 and second 121 encapsulants may be formed as different microstructures (for example, DOEs or Fresnel patterns as shown in FIGS. 63C and 63D) to enhance the light extraction/receiving efficiency.

As illustrated in the top view (FIG. 64A), the substrate 140 area may also be divided into three regions in a different way by two curves; the two rectangular areas may be replaced by two semi-circles enclosing the two photodiodes as shown in this embodiment, while the rest area of the substrate 140 enclosing the LEDs. In the cross sectional view (FIG. 64B) and the oblique view (FIG. 64C), the two second encapsulants 121 are adjacent to the light source 110. The two second encapsulants 121 are embodied as a shape of a quarter-sphere, disposed on two semi-circular areas respectively and sealing the two photodiodes. Additionally, the first encapsulant 111 is embodied as a shape of two side-by-side trapezoid prisms, horizontally disposed on two second encapsulants 121, and seals the LEDs. In addition, there is the first coating 180 on the first encapsulant 111 and the second coating 181 on the second encapsulants 121. The two second encapsulants 121 may also be constructed as a shape of a quarter-ellipsoid, a partial parabolic sphere or the like with their top surfaces covered by the second coating 181; the first encapsulant 111 are constructed on top of the two second encapsulants 121 with the top surface covered by the first coating 180.

As illustrated in the top view (FIG. 65A), the substrate 140 area may also be divided into three regions in a different way by two curves; the two rectangular areas may be replaced by two semi-circles enclosing the two photodiodes as shown in this embodiment, while the rest area of the substrate 140 enclosing the LEDs. In the cross sectional view (FIG. 65B), the two second encapsulants 121 are embodied as a shape of a quarter-sphere, disposed on two semi-circular areas respectively and sealing the two photodiodes. It is contemplated that the contact surfaces of the first 111 and second 121 encapsulants may be formed as different microstructures (for example, DOEs or Fresnel patterns as shown in FIGS. 65C- and 65D) to enhance the light extraction/receiving efficiency.

In the present disclosure, as shown in FIGS. 66-68, the first encapsulant is formed as a shape of side-by-side cylinders to enhance the light extraction efficiency. The top surface of the first encapsulant 111 may be configured as two curvature intersecting beyond the light source 110. The curvature design of the first encapsulant 111 may follow the rule of the total internal reflection at a critical angle ($\theta_c = \arcsin(n_1/n_0)$), where the refractive index of the first encapsulant, $n_1$, is larger than the environment surrounding (for example air) the optical sensor module, $n_0$. Further, the first 111 and the two second 121 encapsulants may have different refractive indices, $n_1$ and $n_2$. As a result, the interface between the first encapsulant and one of the second encapsulants follows the rule of the total internal reflection at a critical angle ($\theta_c = \arcsin(n_1/n_2)$) to reduce light leakage directly from the light source to the photodetector.

The outer surfaces of the first encapsulant 111 and the two second encapsulants 121 may have modifications of configuration. For example, each top surface of the two second encapsulants may be an inclined plane with a predetermined angle between the top surface and the substrate. In one example, each top surface of the two second encapsulants may be a curvature concaved toward the photodetector on the same side. As a result, more emitted light is extracted from the LEDs and more reflected light is collected to the photodiodes to enhance effective signal strength.

As illustrated in the top view (FIG. 66A), the substrate area is divided into three regions by two straight lines; one rectangular area enclosing the LEDs and two rectangular areas, on the two sides of the LEDs, enclosing the two photodiodes. In the cross sectional view (FIG. 66B) and the oblique view (FIG. 66C), the two second encapsulants 121 are embodied as a shape of a triangle prism, horizontally disposed on two rectangular areas respectively and sealing the two photodiodes. Additionally, the first encapsulant 111 is embodied as a shape of two side-by-side quarter-cylinder as shown in this embodiment and horizontally disposed on two second encapsulants 121 and sealing the LEDs. In addition, there is the first coating 180 on the first encapsulant 111 and the second coating 181 on the second encapsulants 121. The two second encapsulants 121 are constructed together or separately with their top surfaces are covered by the second coating 181; then the first encapsulant 111 may also be constructed as two curved surfaces on top of the two second encapsulants 121.

As illustrated in the top view (FIG. 67A), the substrate area may also be divided into three regions in a different way by two curves; the two rectangular areas may be replaced by two semi-circles enclosing the two photodiodes as shown in this embodiment, while the rest area of the substrate 140 enclosing the LEDs. In the cross sectional view (FIG. 67B) and the oblique view (FIG. 67C), the two second encapsulants 121 are embodied as a shape of a triangle prism, horizontally disposed on two rectangular areas respectively and sealing the two photodiodes. Additionally, the first encapsulant 111 is embodied as a shape of two side-by-side quarter-cylinder as shown in this embodiment and horizontally disposed on two second encapsulants 121 and sealing the LEDs. In addition, there is the first coating 180 on the first encapsulant 111 and the second coating 181 on the second encapsulants 121. The two second encapsulants 121 may also be constructed as a shape of a quarter-ellipsoid or a partial parabolic sphere or the like with their top surfaces are covered by the second coating 181; then, the first encapsulant 111 may also be constructed as two curved surfaces on top of the two second encapsulants 121.

Figure 68A:
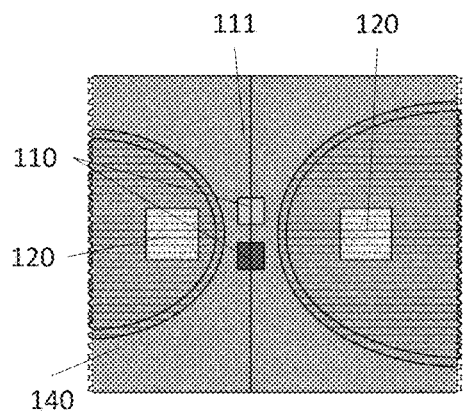
FIG. 68A-68C are schematic diagrams of a top view, cross-sectional view, and oblique sectional view, respectively, of an optical sensing module in accordance with an embodiment of the present disclosure.
Figure 68C:
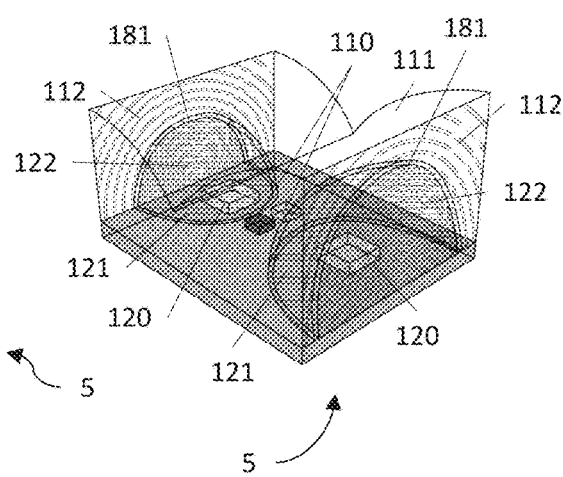
Figure 68B:
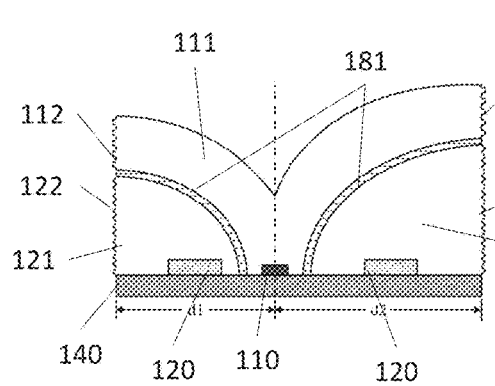
Figure 68D:
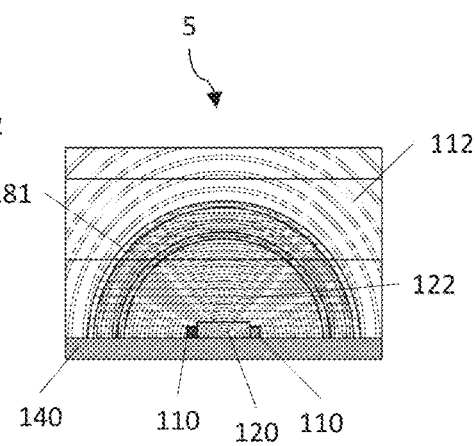
FIG. 68D is the side view of an optical sensor module from the side of contact surface.
Figure 69A:
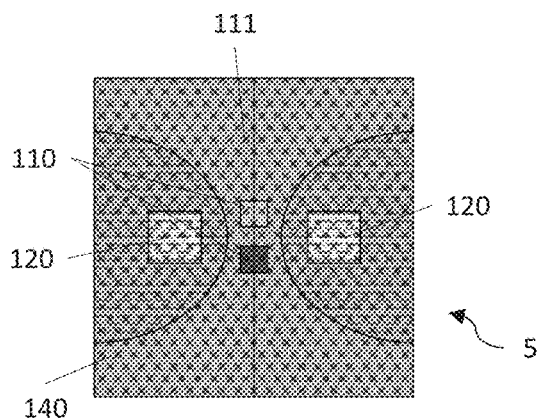
FIG. 69A-69C are schematic diagrams of a top view, cross-sectional view, and oblique sectional view, respectively, of an optical sensor module in accordance with an embodiment of the present disclosure.
Figure 69C:
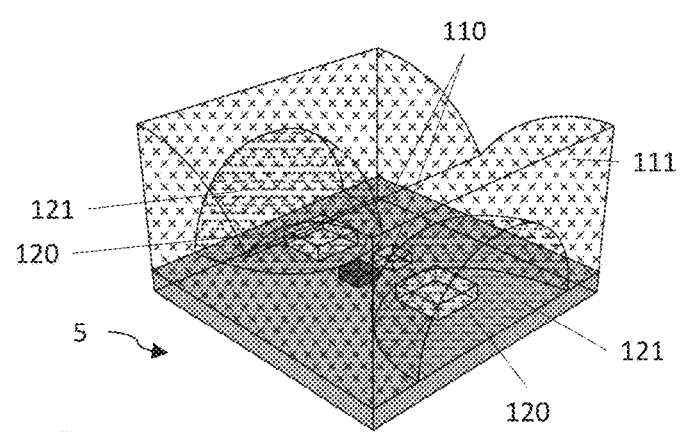
Figure 69B:
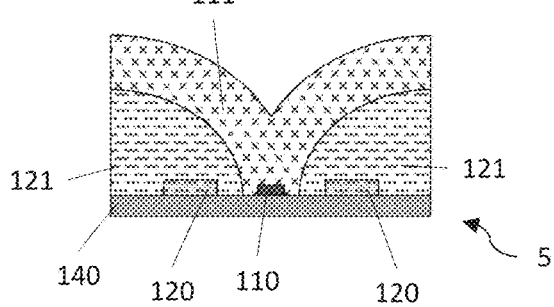

As illustrated in the top view (FIG. 68A), the substrate area may also be divided into three regions in a different way by two curves; the two rectangular areas may be replaced by two semi-circles enclosing the two photodiodes as shown in this embodiment, while the rest area of the substrate 140 enclosing the LEDs. In the cross sectional view (FIG. 68B), the two second encapsulants 121 are embodied as a shape of a triangle prism, horizontally disposed on two rectangular areas respectively and sealing the two photodiodes. It is contemplated that the contact surfaces of the first 111 and second 121 encapsulants may be formed as different microstructures (for example, DOEs or Fresnel patterns as shown in FIGS. 68C and 68D) to enhance the light extraction/receiving efficiency. In addition, a coating 180 or a wall (nontransparent sealing material) may be disposed on the top surfaces of the second encapsulants to enhance SNR.

In one example of the present disclosure, as shown in FIG. 69, the first encapsulant 111 and the two second 121 encapsulants may have different refractive indices, where the refractive index of the second encapsulants 121, $n_2$, is larger than the one of the first encapsulant 111, $n_1$, to reduce direct light leakage from the light source to the photodetectors and ambient stray light according to the Fresnel rule. The surface of both encapsulants have a predetermined surface configuration to enhance SNR; in this embodiment, the first encapsulant 111 is formed as a shape of side-by-side cylinders to enhance the light extraction efficiency. The curvature design of the first encapsulant 111 may follow the rule of the total internal reflection at a critical angle ($\theta_c = \arcsin(n_1/n_0)$), where the refractive index of the first encapsulant 111, $n_1$, is larger than the environment surrounding (e.g. air) the optical sensor module, $n_0$.

The surface planes of the first encapsulant 111 and the two second encapsulants 121 have a predetermined tilting angle or curvature, and hence the second coating 181; therefore, more emitted light is extracted from the LEDs and more reflected light is collected to the photodiodes to enhance effective signal strength.

As illustrated in the top view (FIG. 69A), the substrate 140 area may also be divided into three regions in a different way by two curves; the two rectangular areas may be replaced by two semi-circles enclosing the two photodiodes as shown in this embodiment, while the rest area of the substrate 140 enclosing the LEDs. In the cross sectional view (FIG. 69B) and the oblique view (FIG. 69C), the two second encapsulants 121 are each embodied as a shape of a triangle prism, horizontally disposed on two rectangular areas respectively and sealing the two photodiodes. Additionally, the first encapsulant 111 is embodied as a shape of two side-by-side quarter-cylinder as shown in this embodiment and horizontally disposed on two second encapsulants 121 and sealing the LEDs. In addition, there is the first coating 180 on the first encapsulant 111 and the second coating 181 on the second encapsulants 121. The two second encapsulants 121 may also be constructed as a shape of a quarter-ellipsoid or a partial parabolic sphere or the like; then the first encapsulant 111 may also be constructed as two curved surfaces on top of the two second encapsulants 121.

It is also contemplated that the configuration (for example, inclined angle of top surfaces) and the material (for example, refractive index) of the two second encapsulant 121/coating 180 may differ from each other. The second encapsulants 121 may be asymmetric resulting an asymmetric first encapsulant 111, for more specific applications. Further, the side surfaces of the first 111 and second 121 encapsulants may be formed as different microstructures to enhance the light extraction/receiving efficiency.

An optical sensor module 10 may be a dual sensor module 6. The dual sensor module 6 is manufactured to detect the reflected light and electric signals. The dual sensor module comprises a light source, a first encapsulant over the light source, a photodetector, a second encapsulant over the photodetector, a packaging wall, a detector circuit board, and at least one electrode.

An electrode is configured to be a transducer or to detect an external circuit formed by the contact with an object surface. An electrode is an electrically conductive material, which connects between the external circuit and the detector circuit board inside the dual sensor module. The material of electrodes are usually metal or alloy with good conductivity, for example, copper or gold. Moreover, a single electrode may serve as a thermocouple, made of two pieces of alloy with a different Seeback coefficient (for example, alumel and chromel). The electrodes are arranged to have an adequate contact interface with the object surface (for example, biological tissue or skin surface).

Figure 73B:
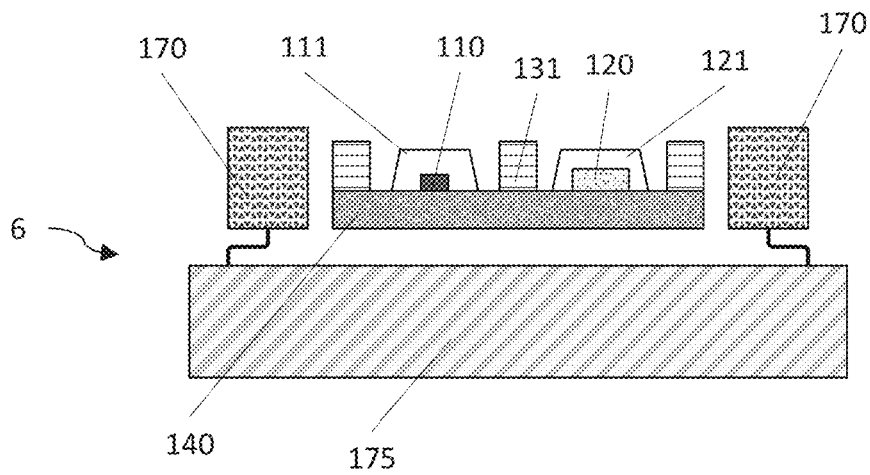
Figure 74A:
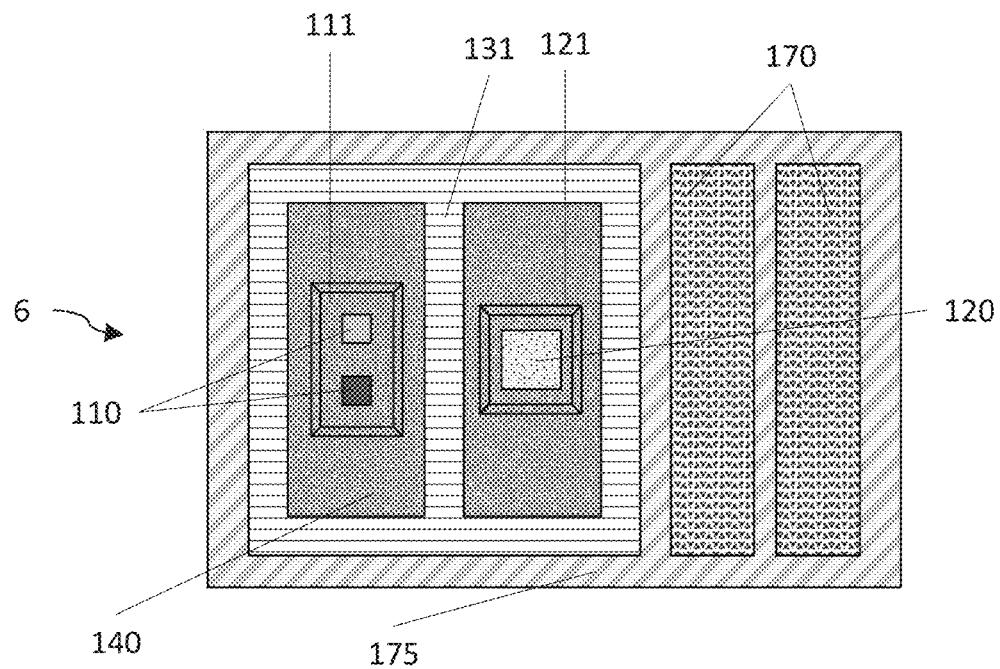
FIG. 74A-74B are schematic diagrams of a top view and cross-sectional view, respectively, of an optical sensor module in accordance with an embodiment of the present disclosure.
Figure 74B:
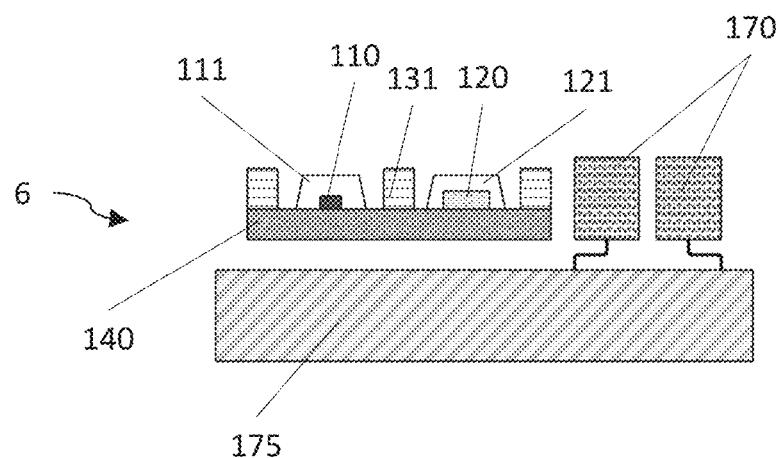

A part of a substrate 140 may be configured as a detector circuit board 175. A detector circuit board 175 is configured to have an electrical connection to at least an electrode 170 and to provide electrical pin(s) for further signal delivery. The detector circuit board 175 may comprise a logic circuit or an operational amplifier circuit to help the electrodes 170 to obtain the electrical properties, such as electrical current, conductance, impedance, or electrical potential difference. The detector circuit board 175 may be integrated with the substrate having the optoelectronics thereon or may be a separate printed circuit board connected to the substrate. In some examples as shown in FIG. 73B and FIG. 74B, the substrate has the first part 140 of the substrate configured to provide connection to the light source 110 and the photodetector 120 and the second part 175 of the substrate configured as a detector circuit board to provide electrical connection to the electrodes 170.

Figure 70A:
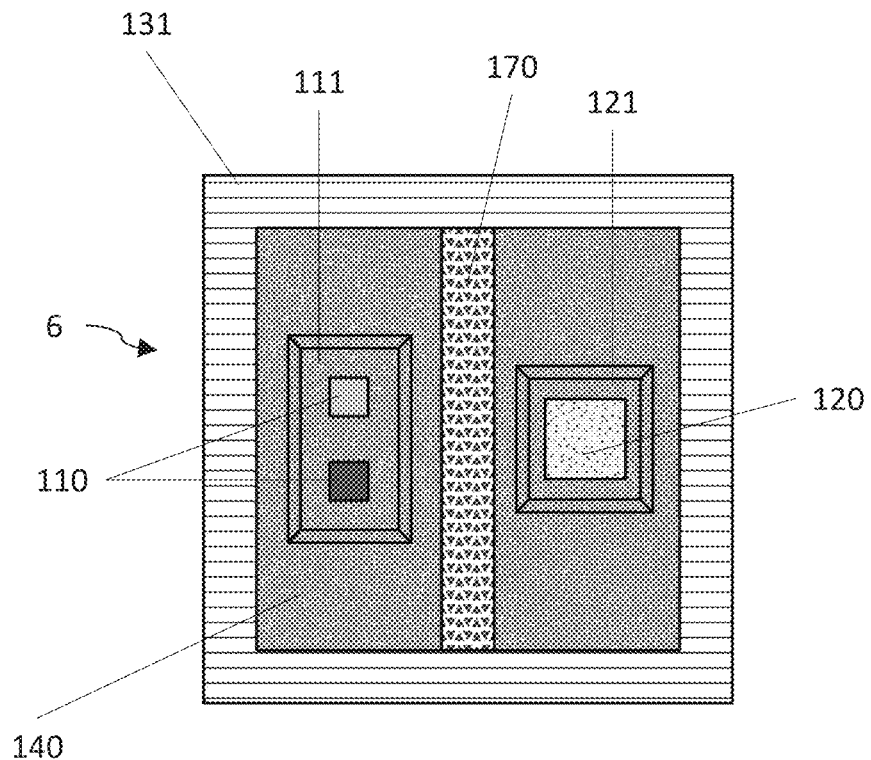
FIG. 70A-70B are schematic diagrams of a top view and cross-sectional view, respectively, of an optical sensor module in accordance with an embodiment of the present disclosure.
Figure 70B:
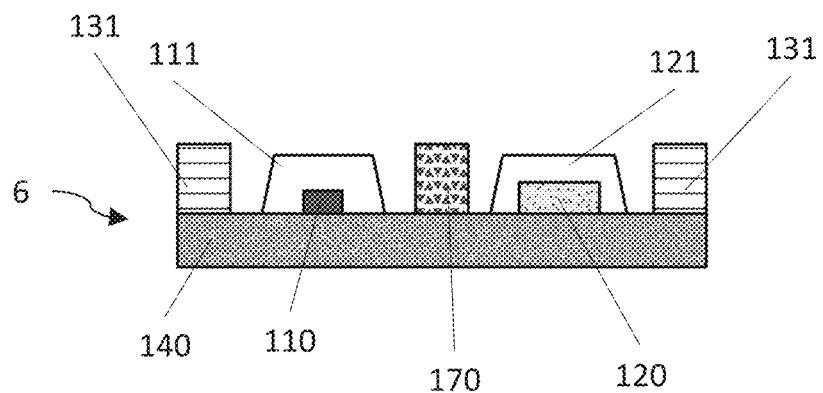

The dual sensor module 6 is an integrated sensor module comprising an optical sensor part and an electrical sensor part to have multiple function within a single piece of a dual sensor module 6. The dual sensor module 6 has many advantages, such as volume miniaturization and in situ dual signal acquisition. The single electrode 170 in a dual sensor module may be solely functional as a thermocouple. The single electrode 170 in a dual sensor module may be cooperated with another dual sensor module or an independent electrode to form as a functional pair of electrodes. In FIG. 70A, the dual sensor module has the light source 110, the first encapsulant 111 covering the light source 110, the photodetector 120, the second encapsulant 121 covering the photodetector 120, the packaging wall 131, the substrate 140 and the electrode 170 disposed between the light source 110 and the photodetector 120. In FIG. 70B, the light source 110, the photodetector 120 and the electrode 170 are disposed on the same substrate 140.

Figure 71A:
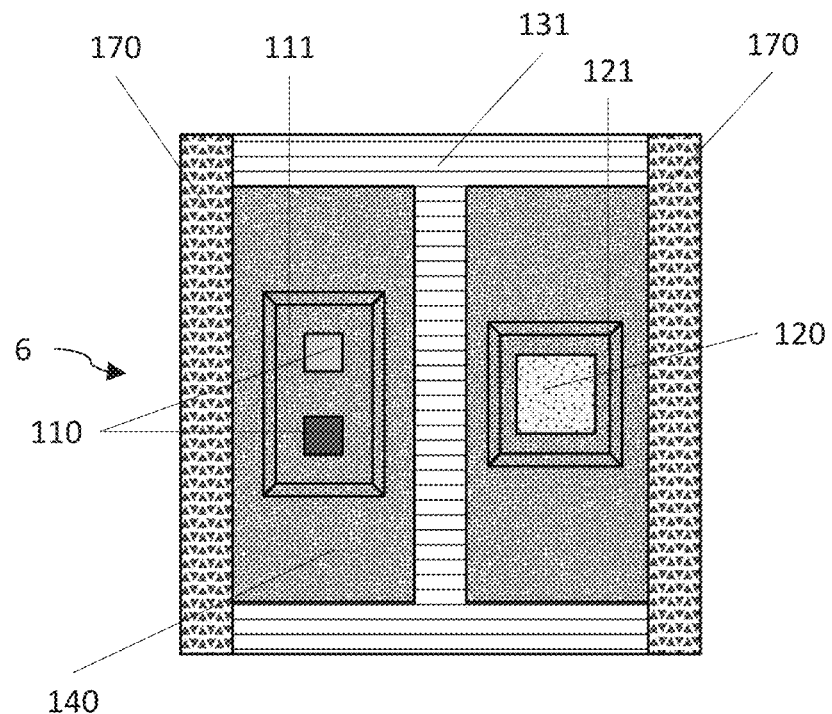
FIG. 71A-71B are schematic diagrams of a top view and cross-sectional view, respectively, of an optical sensor module in accordance with an embodiment of the present disclosure.
Figure 71B:
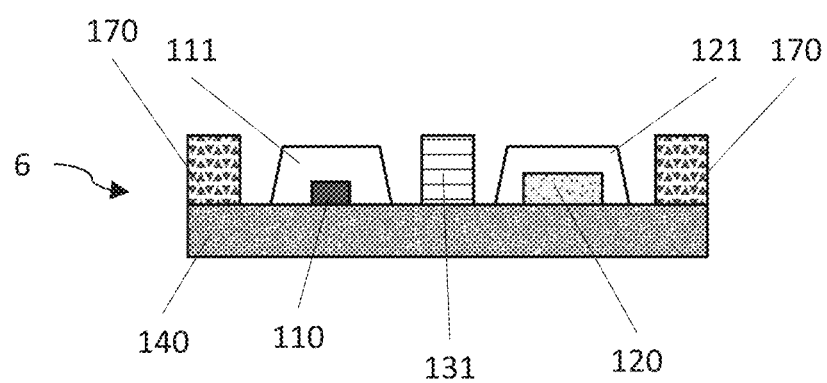

As shown in FIG. 71A, the dual sensor module has the light source 110, the first encapsulant 111 covering the light source 110, the photodetector 120, the second encapsulant 121 covering the photodetector 120, the packaging wall 131, the detector circuit board 175 and the electrodes 170. The packaging wall 131 is disposed between the light source 110 and the photodetector 120. The two electrodes 170 are disposed on the opposite border of the detector circuit board 175. One electrode 170 is disposed laterally to the light source 110 and the other electrode 170 is disposed laterally to the photodetector 120. The packaging wall 131 is configured to reduce the direct light leakage from the light source 110 and the photodetector 120 and may extend bilaterally to further block ambient light. In FIG. 71B, the light source 110, the photodetector 120 and the electrode 170 are disposed on the same detector circuit board 175.

Figure 72A:
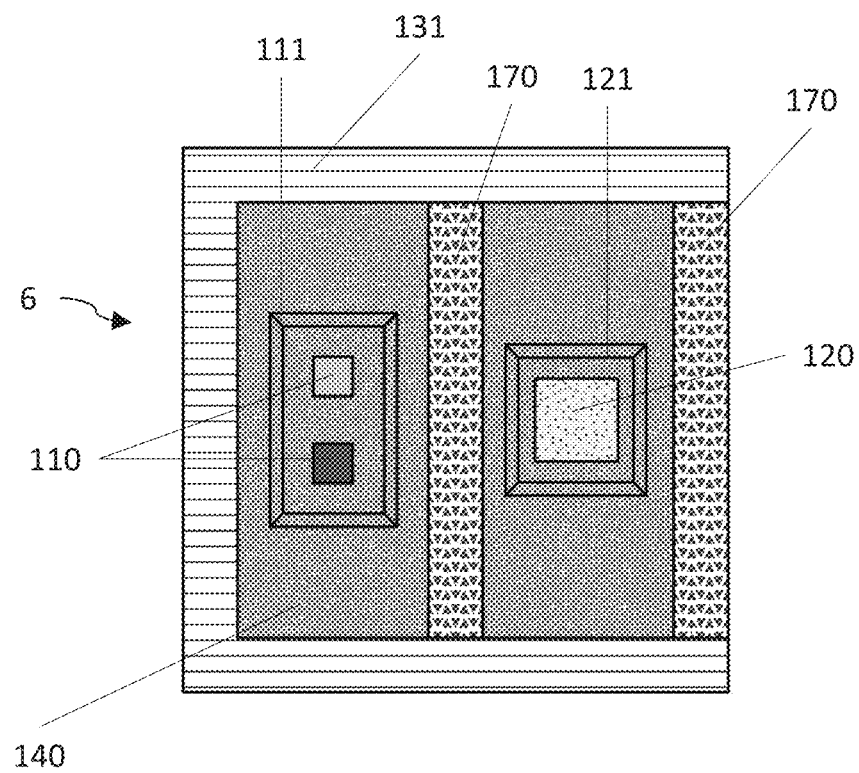
FIG. 72A-72B are schematic diagrams of a top view and cross-sectional view, respectively, of an optical sensor module in accordance with an embodiment of the present disclosure.
Figure 72B:
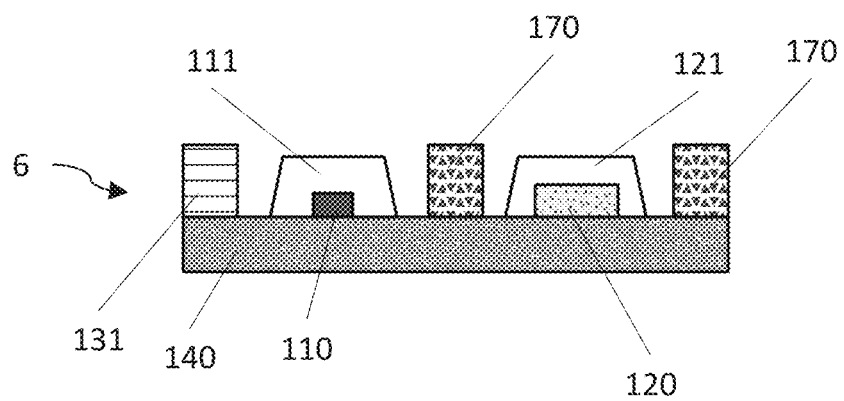

As shown in FIG. 72A, the dual sensor module has the light source 110, the first encapsulant 111 covering the light source 110, the photodetector 120, the second encapsulant 121 covering the photodetector 120, the packaging wall 131, the detector circuit board 175 and the electrodes 170. One electrode is disposed between the light source 110 and the photodetector 120 and the other electrode is disposed on the border of the detector circuit board. The packaging wall 131 is configured to block ambient light and to separate the two electrodes. The packaging wall 131 is electrically insulated, so that the two electrode are capable of detecting the electrical potential difference. In FIG. 72B, the light source 110, the photodetector 120 and the electrodes 170 are disposed on the same detector circuit board 175. It is contemplated that the electrodes 170 may be disposed on other sides of the detector circuit board 175. For example, one electrode 170 is disposed between the light source 110 and the photodetector 120, and the other electrode 170 is disposed on the border of the light source side of the detector circuit board 175. For example, the dual sensor module may have a packaging wall 131 disposed between the light source 110 and the photodetector 120 and the electrodes may be disposed perpendicular to the packaging wall 131.

As shown in FIGS. 73-74, the substrate 140 is composed by a first part and a second part. The first part of the substrate may have a light source 110 and the photodetector 120 thereon, while the second part of the substrate may be a detector circuit board 175 to provide connection to the electrode(s) 170. The light source 110 and the photodetector 120 are disposed on the substrate 140. The detector circuit board 175 may be mechanical connected to the substrate 140, or may be electrical connected to the circuit within the substrate 140 for better synchronization between the optical measurement and the electrical measurement.

Figure 73A:
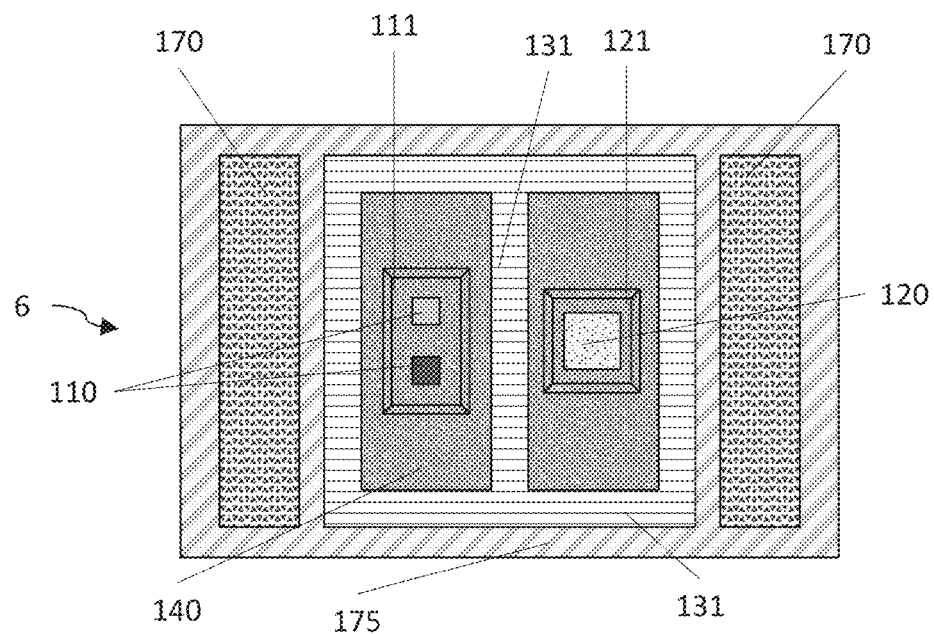
FIG. 73A-73B are schematic diagrams of a top view and cross-sectional view, respectively, of an optical sensor module in accordance with an embodiment of the present disclosure.

In FIG. 73A, the detector circuit board 175 is larger than the substrate 140 and the substrate 140 and the two electrodes 170 are disposed on the detector circuit board 175. The packaging wall 131 is disposed between the light source 110 and the photodetector 120 to reduce light leakage and may extend to enclose the border of the substrate 140 to further block ambient light. In FIG. 73B, each of the electrodes 170 has electrical connection to the detector circuit board 175. The electrodes are separated from each other by the substrate 140. In FIG. 74A, two electrodes 170 are disposed on the detector circuit board 175 with a limited distance and thus may have a smaller impedance of the external circuit when being applied to an object surface. In FIG. 74B, each of the electrodes 170 has electrical connection to the detector circuit board 175.

In FIGS. 75-79, the dual sensor module 6 may further comprise a cover 150, and the cover 150 may be located, during application, between the encapsulants and the object surface, while not blocking the contact between the electrodes 170 and the object surface. The cover 150 serves as a contact interface between the object surface (such as a biological tissue surface or a skin surface) to increase the durability of the dual sensor module 6 and the consistency of measurement.

Figure 75A:
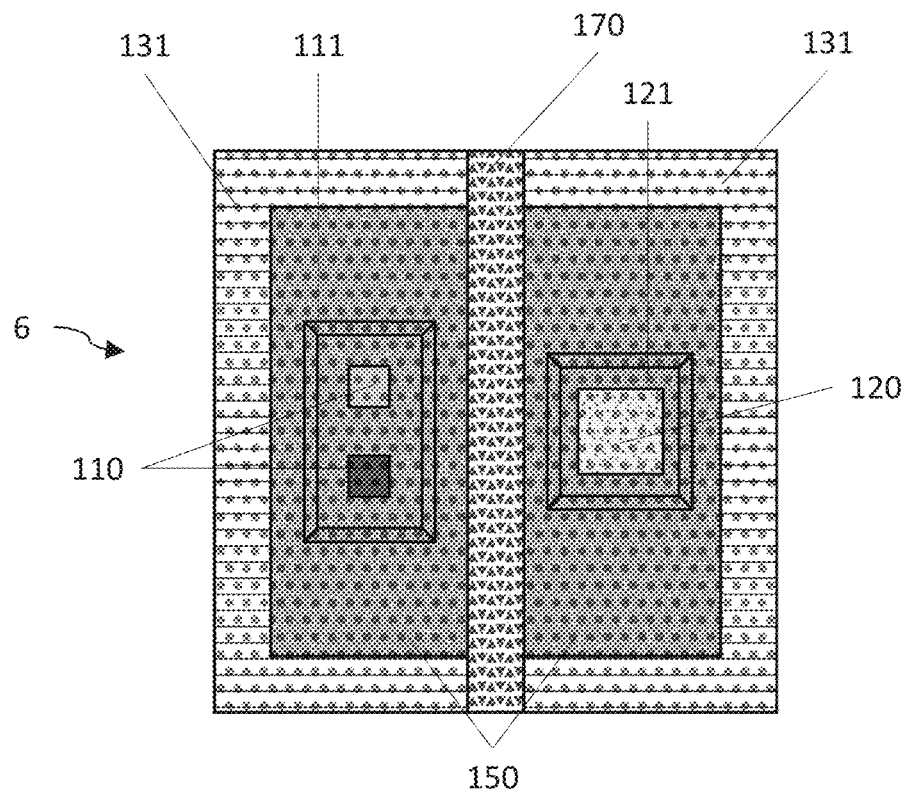
FIG. 75A-75B are schematic diagrams of a top view and cross-sectional view, respectively, of an optical sensor module comprising a cover in accordance with an embodiment of the present disclosure.
Figure 75B:
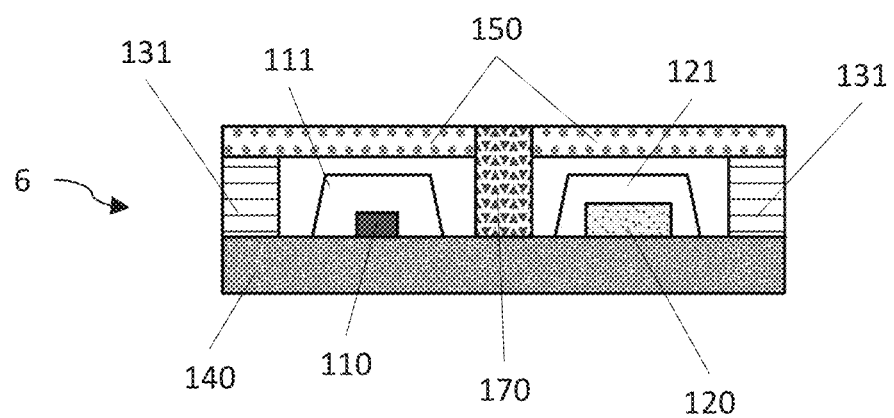

In one embodiment as shown in FIG. 75A, the dual sensor module 6 comprises a cover 150 disposed beyond the light source 110 and the photodetector 120, while at least a part of the electrode 170 is exposing outward. The cover 150 may be separated by the electrode 170 or may be a single piece with a slot for exposure of the electrode 170. In FIG. 75B, the cover 150 may be mechanically connected to the packaging wall 131 to provide mechanical support.

Figure 76A:
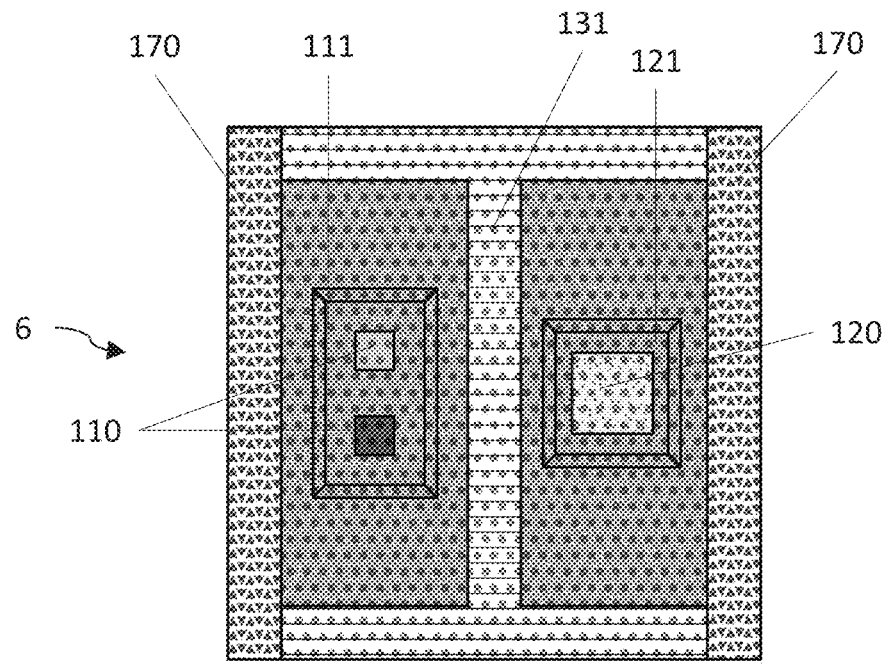
FIG. 76A-76B are schematic diagrams of a top view and cross-sectional view, respectively, of an optical sensor module comprising a cover in accordance with an embodiment of the present disclosure.
Figure 76B:
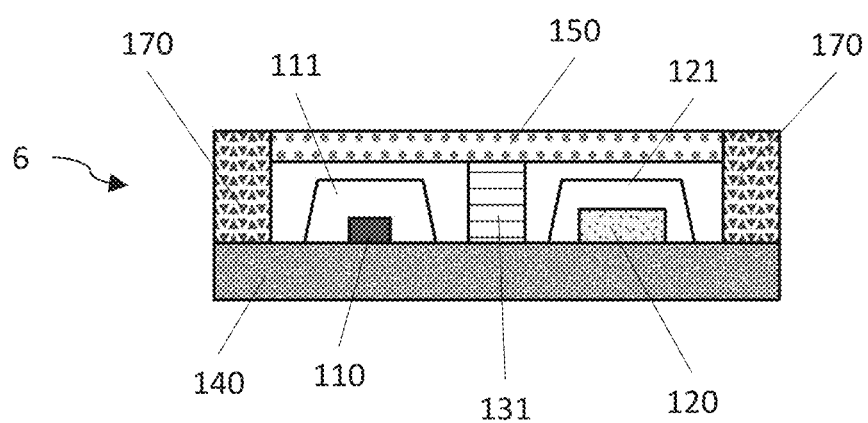

In FIG. 76A, the cover 150 may be disposed beyond the light source 110 and the photodetector 120, while at least a part of the two electrodes 170 are exposed outward from the cover 150. In FIG. 76B, a packaging wall 131 is disposed between the light source 110 and the photodetector 120 and provide mechanical support to the cover 150. The packaging wall 131 may extend to enclose the border of the detector circuit board 175 to block ambient light and provide better mechanical support for the cover 150.

Figure 77A:
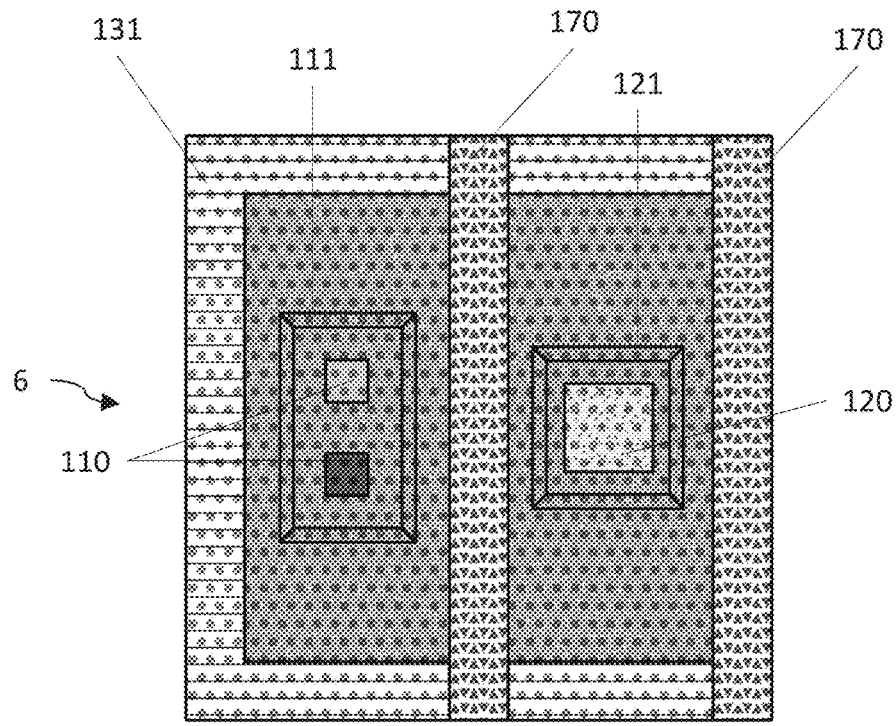
FIG. 77A-77B are schematic diagrams of a top view and cross-sectional view, respectively, of an optical sensor module comprising a cover in accordance with an embodiment of the present disclosure.
Figure 77B:
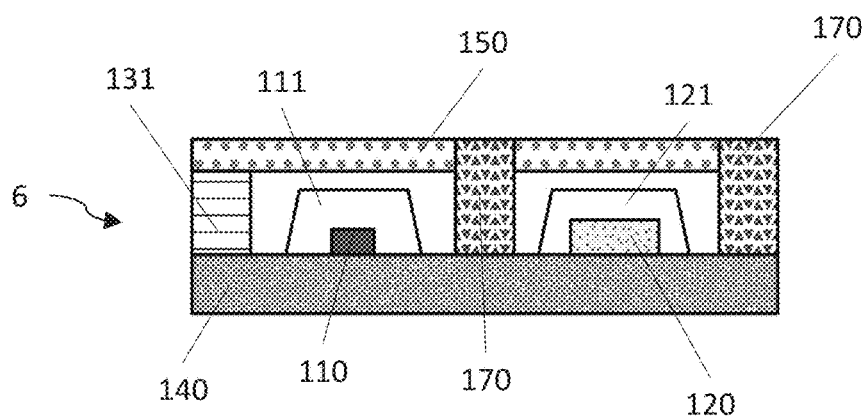

In FIG. 77A, the cover 150 may be disposed beyond the light source 110 and the photodetector 120, while at least a part of the two electrodes 170 are exposed outward from the cover 150. The cover 150 may be a single piece with one slot for exposure of the electrode 170 between the light source 110 and the photodetector 120. The cover 150 may be a single piece with two slots each for an electrode 170. The cover 150 may comprise two separate parts for exposure of the electrodes 170. In FIG. 77B, a packaging wall 131 is disposed to provide mechanical support to the cover 150. The packaging wall 131 may extend to enclose the border of the detector circuit board 175 to block ambient light and provide better mechanical support for the cover 150. The packaging wall may be separated by the electrodes 170 or may be fabricated as a continuous wall enclosing the border the detector circuit board 175.

In addition, the internal surface or the external surface of the cover 150 may be coated with a thin film 151. The thin film may be an anti-reflective (such as index-matching thin film or interference thin film) or an anti-scratch thin film (such as polyethylene terephthalate, or silicon hard coating).

As shown in FIG. 78A, both internal surface and the external surface of the cover 150 are coated with thin films. In an enlarged view (FIG. 78B), the external surface of cover 150 is covered with an anti-scratch thin film and the internal surface of the cover 150 is covered with an anti-reflective thin film. It is contemplated that the two surfaces may be covered with same kind of thin film or one of the surfaces of the cover 150 may have no thin film.

In one example as shown in FIGS. 79A-C, the dual sensor module 6 may further comprise a thin film 160 covering an encapsulant. With thin film technology, the SNR of the optical signals may be further improved. The thin film 160 may be an anti-reflective thin film or a filter thin film. The anti-reflective thin film may be an index-matching film (for example, Rayleigh film) or an interference film to improve light extraction efficiency by reducing Fresnel reflection at the interface between the encapsulants and the environmental medium. The filter thin film may be a long-pass filter, a short-pass filter, or a band-pass filter to clear down the full width at half maximum (FWHM) of the emitting light or filter out the noise from undesired wavelengths.

As shown in FIG. 79A, both the surfaces of the first encapsulant 111 and the second encapsulant 121 are coated with a thin film 160. The thin film 160 of the first encapsulant 111 is embodied as an anti-reflective thin film (FIG. 79B) and the thin film 160 of the second encapsulant 121 is embodied as a band-pass filter thin film (FIG. 79C). The anti-reflective thin film improves the light extraction efficiency and the band-pass filter thin film reduces noise. It is contemplated that the thin film 160 of the first encapsulant 111 may be a band-pass filter thin film and the thin film 160 of the second encapsulant 121 may be an anti-reflective thin film, so that the FWHM of the emitting light has a clear cut-off and the photodiode receive more signal light without unnecessary reflection. In the application of fluorescence detection long-pass filter thin film may be applied to the second encapsulant 121 to acquire a clear fluorescent signal avoiding the excitation light.

The integration facilitates acquisition of the optical and electrical signals and computation of acquired signals into meaningful information. The dual sensing device 18 is capable of acquiring optical and electrical signals in situ and computing useful physiological parameters. First, the electric potential difference between two electrodes may be measured by parallel connection to the object circuit. For example, electrocardiogram may be acquired in time series by measuring the potential difference between the electrodes on the body surface with an adequate alignment. Also, the electric impedance of the contact object may be measured by series connection to the object surface 190. For example, the fat content or hydration status of the biological tissue may be further calculated from the measured impedance. In addition, the electrodes may also serve as a thermocouple to measure the object temperature. For example, body surface temperature may be measured as a reference of core temperature. For example, the pulse wave velocity can be calculated from the pulse phase difference, and some disease status may be inferred from the phase angle of the bioelectrical impedance.

In general, an optical sensing device or an optical sensing accessory is an integration of one or more optical sensor modules 10 with other electronic modules in a housing. Other electronic modules are configured to assist the optical sensor module 10 in transmitting, digitizing, processing, or storing the optical signals and to combine the optical signals with other concomitant information; meanwhile, the housing keeps all the electronic modules from external damage and provides a human interface for mobile use. The integration facilitates acquisition of the optical signals and transformation of the acquired optical signals into meaningful information. Specifically, within the range of optical window, incident light can travel in a depth of a biological tissue, and therefore, the information underneath the surface of the biological tissue can be extracted by the reflected light. By studying the spectrum of specific wavelengths, people may further obtain the computed biochemical or physiological parameters. The analysis of optical properties of a biological sample, in vivo, ex vivo, or in vitro, may be accomplished through the operation of the optical sensing device. Accordingly, the acquired optical signals are more accessible and applicable with the present technology of the optical sensing device.

With certain purposes of application, the optical sensing device or the optical sensing accessory have, at least, an optical sensor module and a housing. An optical sensor module may be the optical sensor module, the multi-directional optical sensor module, or the dual sensor module defined in the present disclosure. The other electronic modules may be a microprocessor 20, a communication module 60, a battery 50, a memory 40, a GPS receiver module 70, or other types of sensors; a wearable housing is configured to carry an optical sensing device and attaching human body for mobile use.

A microprocessor 20 may be an ARM based or 8086x microprocessor, most available in mobile device, are capable of processing the large amount of data and have an advantage of energy saving. A microprocessor 20 may have analogue input pins allowing analogue signal processing.

The input interface module 31 include keyboard, mouse, or microphone in conventional computing devices, or touch screen, microphone, or camera in mobile devices. The output interface module can output information in visual or audible forms. The visual output module 36 may be a microprojector, LCD, LED, OLED, or E-Paper display, and the audible output module 37 may be a beeper, a speaker, or a piezoelectric buzzer.

A memory 40 stores the digital information assigned by the microprocessor 20 of the optical sensing device. The memory 40 may work as a system buffer to deal with abundant data input, and may work as a storage to preserve the structured information for later exporting to the other computing device or a cloud server. The memory 40 may be volatile or non-volatile. Volatile memory is embodied as random access memory (RAM) in most mobile device, and non-volatile memory is embodied as flash memory.

A power supply provides the power necessitated for the operation of the device. A power supply may be a battery 50, a transformer, or a power transmission line connected to a direct current source. Both primary and secondary batteries may be a source of power supply used in the optical sensing device. In at least one example, the primary and secondary batteries can rely upon lithium battery technology. In other examples, the primary and secondary batteries can be made using technology to allow the desired discharge rates, life cycle, and rechargeablity.

A communication module 60 transmits the electrical signals between an optical sensing device and an external device, where the electrical signals may be control signals or data signals. The communication module 60 may be wired 61 or wireless 66. Wired communication module 61 may be a serial port such as one wire, USB, I2C, or SPI. Wireless communication module 66 may be Wi-Fi, standard Bluetooth, Bluetooth Low Energy, or cellular mobile network (for example, GSM, 3G, or 4G). In one example, an analogue front end is integrated as a part of Bluetooth module, which enables the analogue signals to be transmitted.

A GPS receiver module 70 is configured to gather geographic information, and help to record the location where the optical information is collected. With time series recording, the GPS information provides a dynamic tracing of the user's displacement and velocity.

Other sensors transducing thermal, mechanical, or biopotential signals into electrical signals may be also incorporated into the optical sensing device to provide more environmental and physiological information. For example, electrical thermometer 82 is able to detect the ambient and body temperature; accelerometer 81 detects body motion; electrocardiograph leads detect cardiac electric activity. Besides, the electrical property of biological tissue (for example, electrical impedance, or conductivity) may indicate some physiological information (for example, body fat index, or moisture.)

Figure 80A:
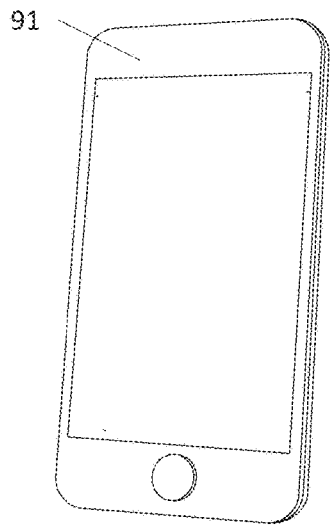
FIG. 80A-80D are schematic diagrams of the housing of an optical sensing accessory or an optical sensing device.
Figure 80B:
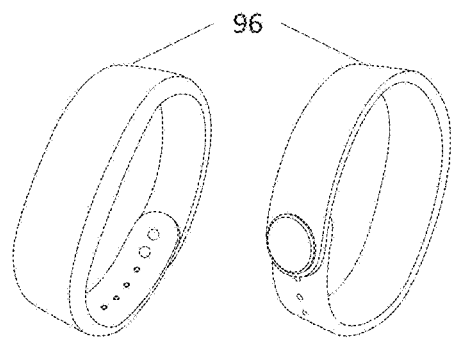
Figure 80C:
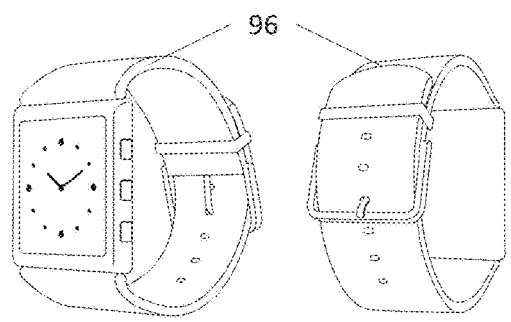
Figure 80D:
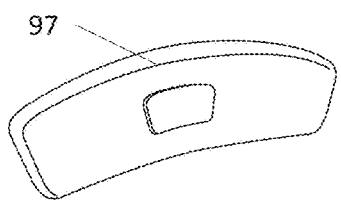
Figure 87A:
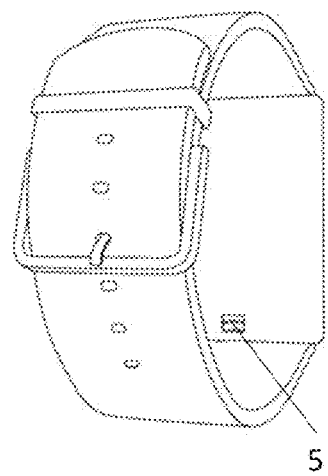
FIGS. 87A and 87B are the schematic diagrams of the optical sensing device having a bi-directional optical sensor module exposing the two contact surfaces to two different surfaces of an optical sensing device.
Figure 87B:
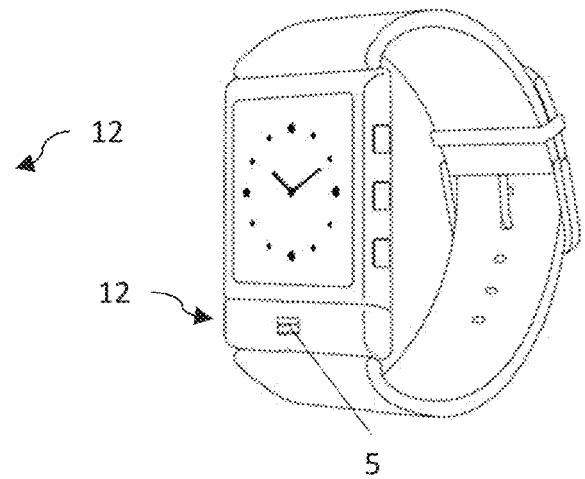
Figure 87C:
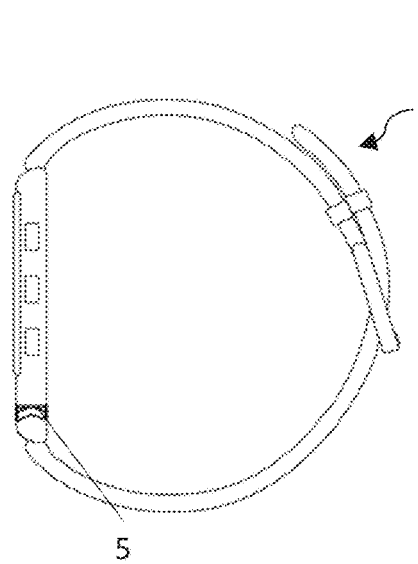
FIG. 87C is a partial cutaway view from side of an optical sensing device having a bi-directional sensing module.
Figure 87D:
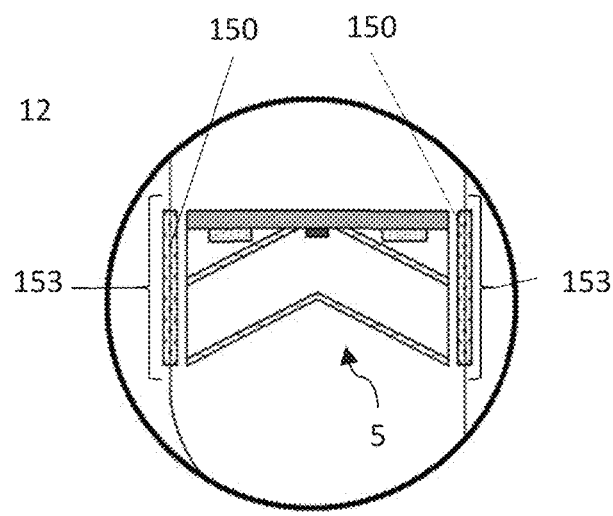
FIG. 87D is an enlarged view of FIG. 87C illustrating a bi-directional sensor module in an optical sensing device having two contact surfaces facing two directions.

A housing provides suitable container to set up the optical module and electronic modules and may provide adequate connection interface for communication with external devices. It also helps measurement consistency on specific body regions and increases the user compliance to the optical sensing device. A housing may be embodied as a housing for a handheld device or a wearable device. A handheld housing 91 features its compact size, light weight, and robustness for mobile applications (FIG. 80A). A wearable housing comprises a body attaching part and a module carrying part. The body attaching part may be an annular shape accessory 96, which attaches to human body by embracing body parts, and may be embodied as, a wrist band (FIG. 80B), a head band, an ankle band, a necklace, a belt, a watch (FIG. 80C), or the like. Also, the body attaching part may be a patch shape accessory 97, which attaches to human body by biocompatible glues or gels, and may be embodied as a tape, a pad (FIG. 80D), a patch, or the like. Furthermore, the body attaching part may be a hook shape, and may be embodied as an earplug, an on-ear accessory, or a spectacle frame. In one example as shown in FIG. 87D, the housing may comprise transparent opening 153 to provide an optical path for the reflective optical sensor module, the optical sensor module, the multi-directional optical sensor module 5, or the dual sensor module. The transparent opening 153 may have a cover 150 and the cover may be configured with microstructure, curvature lens, or thin film on the surfaces of the cover, or any combinations as mentioned.

In the present disclosure, an optical sensing accessory 11 or an optical sensing device 12 may comprise an optical sensor module 10, a multi-directional optical sensor module 5, a dual sensor module 6, or any combinations. For ease of description, an optical sensing accessory or an optical sensing device 12 comprising, but not limited to, an optical sensor module 10 is demonstrated. An optical sensing accessory 11 has a communication module 60 to allow the transmission of acquired signals to a computing device for further signal processing. An optical sensing device 12 has a processor to manage the acquired optical signals. The embodiments of an optical sensing device are exemplified as below.

Figure 81A:
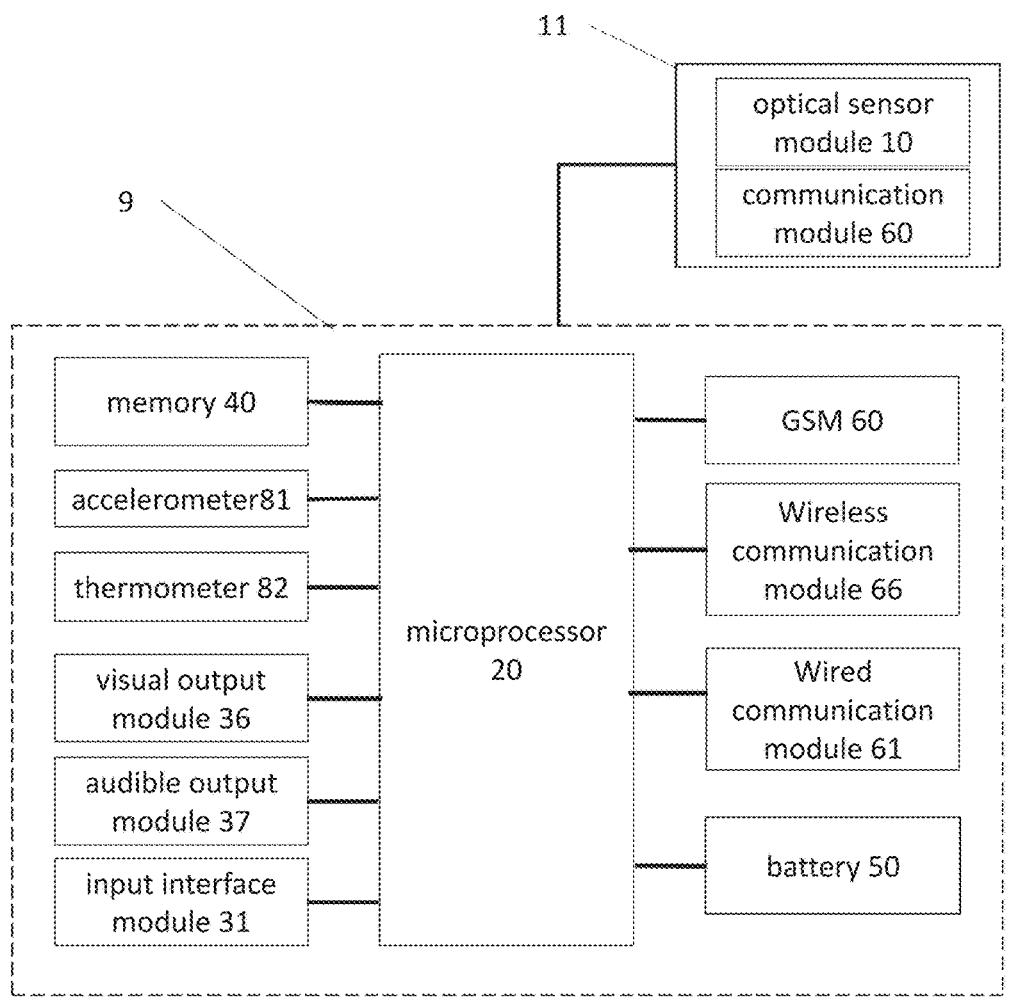
FIG. 81A is a block diagram of an optical sensing accessory connected to a computing device.
Figure 81B:
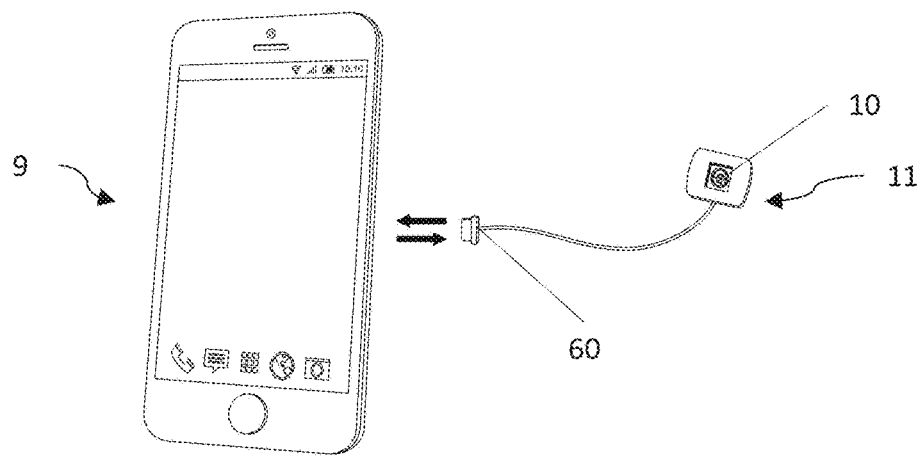
FIGS. 81B and 81C are the schematic diagrams of the optical sensing accessory connected to a computing device.
Figure 81C:
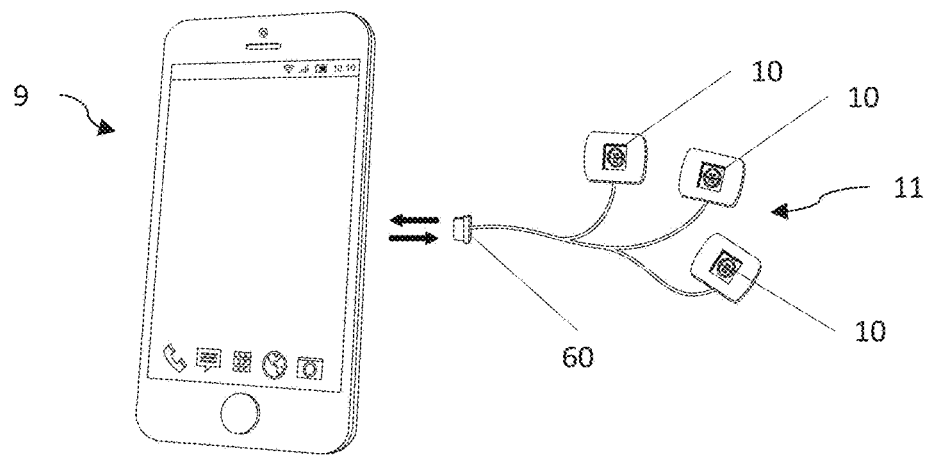
Figure 82A:
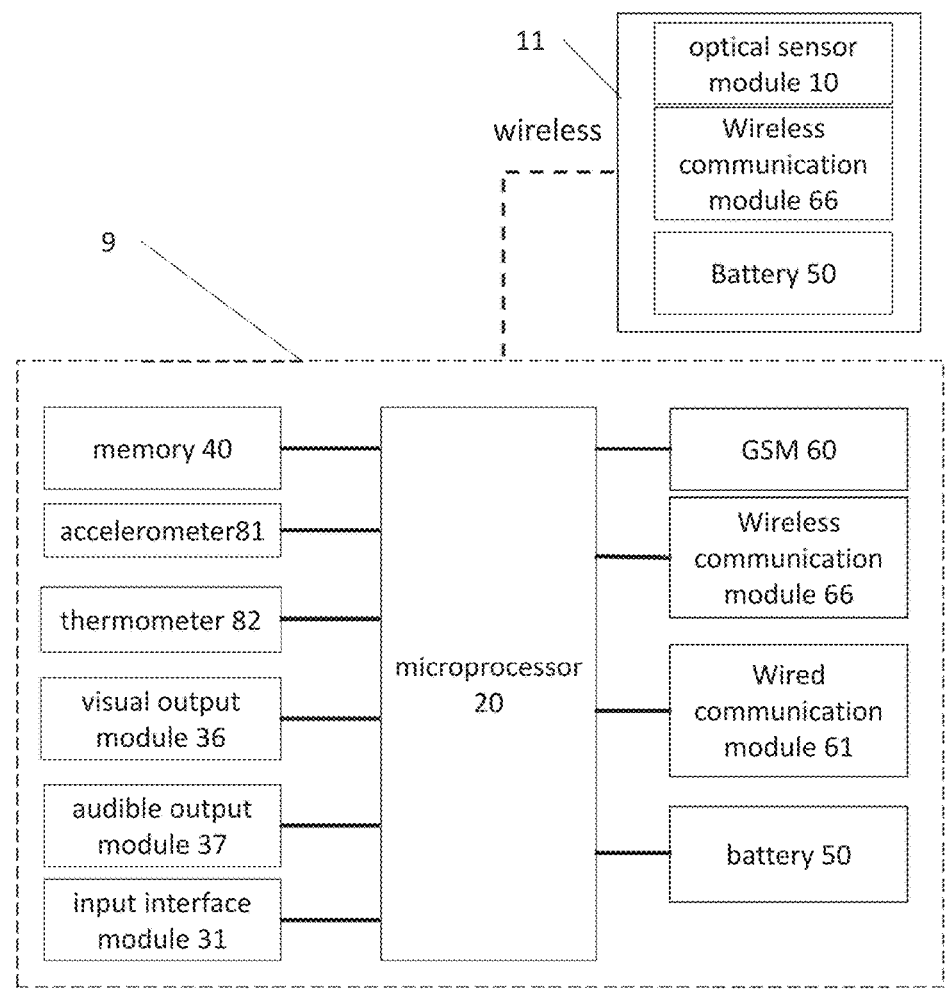
FIG. 82A is a block diagram of a wireless optical sensing accessory connected to a computing device.
Figure 82B:
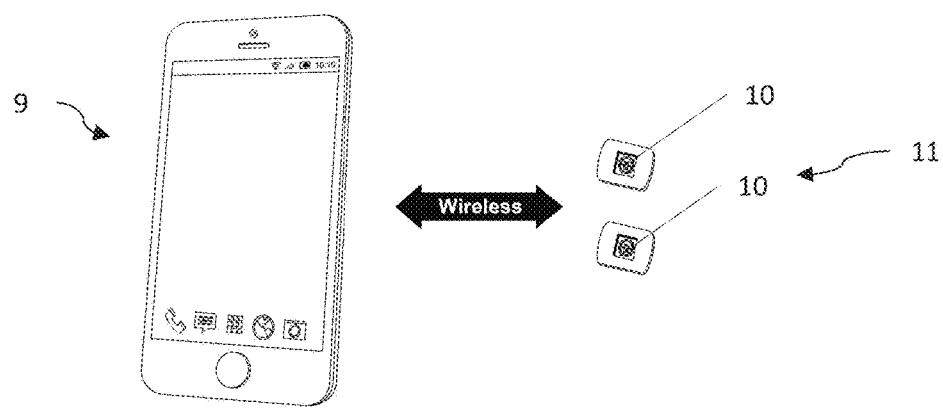
FIG. 82B is a schematic diagram of the wireless optical sensing accessory connected to a computing device.

An optical sensing accessory 11 of the present disclosure is configured to transmit the optical signals from one or more optical sensor modules 10 to a computing device. The optical sensing accessory 11 comprises at least one optical sensor module 10, a communication module 60, and a housing. The optical signals are obtained by the optical sensor module 10, and later, the signals may be conveyed to an independent computing device via the communication module 60 (FIG. 81A). The computing device 9 may be the optical sensing device 12 or a mobile device (for example, smart phone). As depicted in FIGS. 81A-C, an optical sensing accessory 11 to transmit the electrical signals to a computing device. In one example, the optical sensing accessory 11 comprises an optical sensor module 10, a serial cable plug and a wearable housing presented as a wired patch probe. With connection to an external computing device, the optical sensing accessory receives power support and the control signals from the computing device and delivers the converted signals to a computing device via the serial cable (FIG. 81B). In addition, the wired patch probe may comprise multiple optical sensor modules 10 as shown in FIG. 81C. In the case of a wireless optical sensing accessory (FIG. 82A), a battery 50 is necessary to power the signal transmission by radiofrequency. The computing device is capable of triggering the operation of the optical sensing accessory 11 and managing the received signals. As shown in FIG. 82B, multiple wireless optical sensing accessories 11 may be connected and integrated to the computing device.

Also, an optical sensing device 12 of the present embodiments is configured to manage the optical signals from an internal optical sensor module 10 or an external sensing devices 8. An internal optical sensor module 10 is electrically connected to the microprocessor 20, while an external sensing device is connected through a communication module 60. The optical sensing device 12 comprises an optical sensor module 10, a microprocessor 20, a battery 50, a memory 40, and a housing.

Figure 83A:
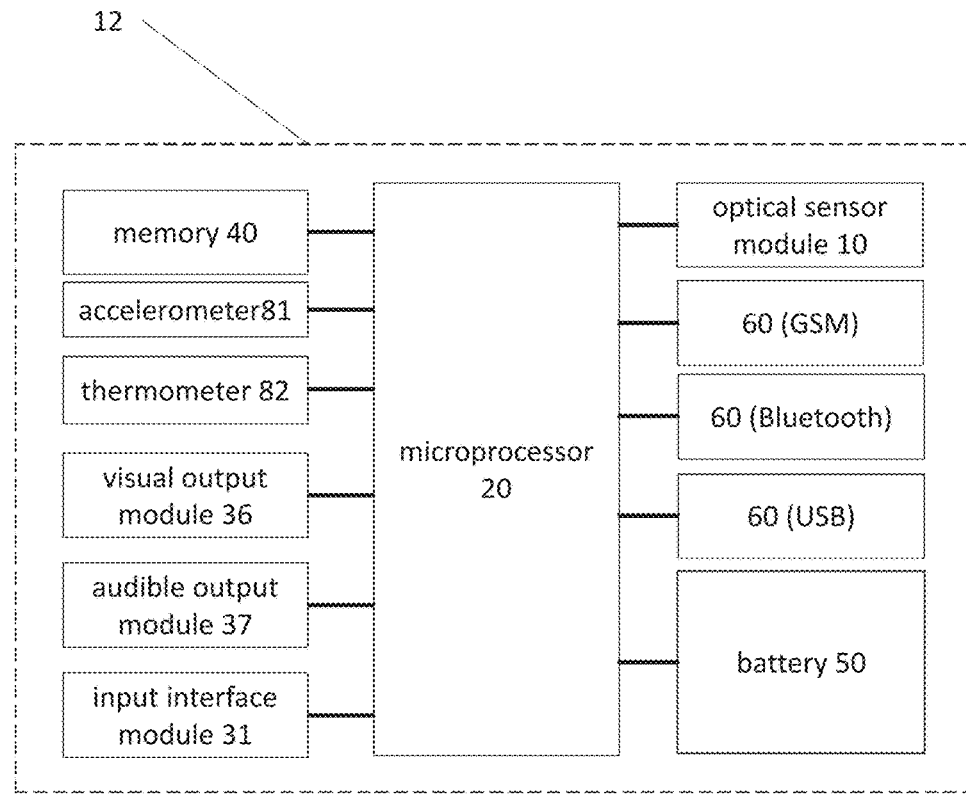
FIG. 83A is a block diagram of an optical sensing device.
Figures 83B, 83C:
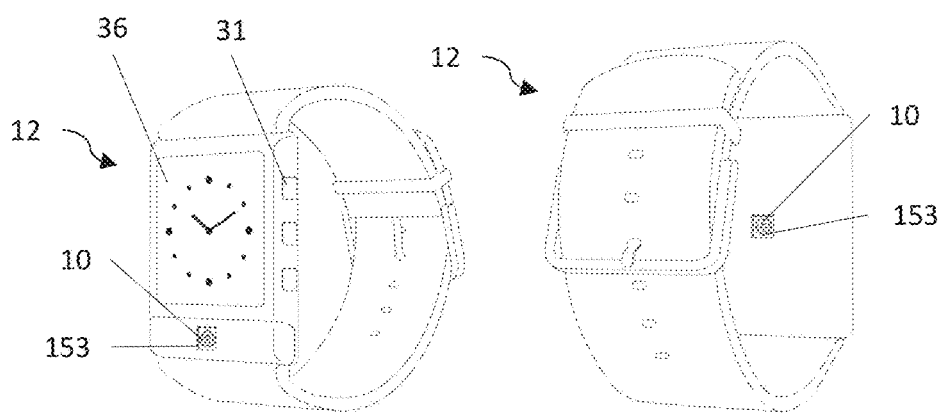
FIGS. 83B and 83C are the schematic diagrams of the optical sensing device comprising an optical sensor module and a wearable housing.

As depicted in FIGS. 83A-C, an optical sensing device 12 is configured to receive, process, store and transmit the optical signals. In at least one example, the optical sensing device 12 comprise an optical sensor module 10, an ARM core microprocessor, a flash memory, and a lithium battery. The optical sensor module 10 may receive and convert the optical signals of a biological tissue to electrical signals and deliver the signals to a microprocessor 20. The general architecture of an optical sensing device 12 is shown as FIG. 83A, and the other electronic modules may be integrated into the optical sensing device 12. The optical signals are obtained by the optical sensor module 10. Later, the electrical signals may be directly delivered to and processed by the optical sensing device 12. The optical sensing device 12 comprising electronic modules is presented as an optical sensing watch 12 (FIGS. 83B and 83C). The acquired optical signal is transduced into the electrical signal and the electrical signal is processed by the microprocessor 20, output as physiological parameters, and then stored in the memory. For example, the infrared and red light absorbance of applied biological tissue is detected by the optical sensor module 10, converted into electrical signals, processed as physiological parameters (for example, oxygen saturation), and stored in a flash memory. In FIG. 83B, an optical sensing watch comprises one transparent opening 153 on the clock face and one optical sensor module 10 is located in the transparent opening. In FIG. 83C, the optical sensing watch comprises the other transparent opening 153 on the case back and the other optical sensor module 10 is located in the transparent opening 153.

The optical sensing device 12 may comprise an optical sensor module 10, an ARM core microprocessor, a flash memory, a lithium battery, and further comprises an input module 31 a visual output module 36, and an audible output module 37. The input interface module 31 may be embodied as a touch screen module. The user may input a request by touch screen to have the optical sensing device 12 send out control signal to the sensor module to acquire signals. The acquired signals are then processed by the microprocessor 20 and stored as physiological information in the memory 40 in the optical sensing device 12. The user may also input a request by touch screen to have the stored physiological information be shown on a display. Additionally, an output module, such as a beeper, may work as a failure-proof reminder or an emergency alerting signal.

Figure 84A:
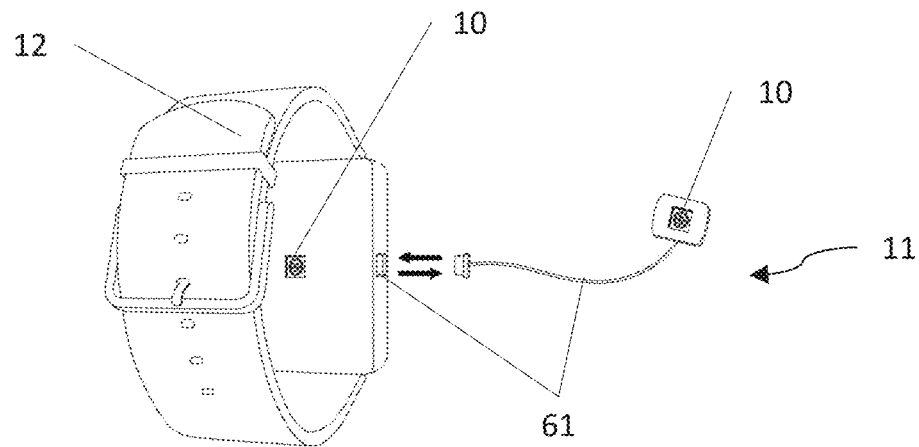
FIG. 84A is a schematic diagram of the optical sensing device connected to an optical sensing accessory.
Figure 84B:
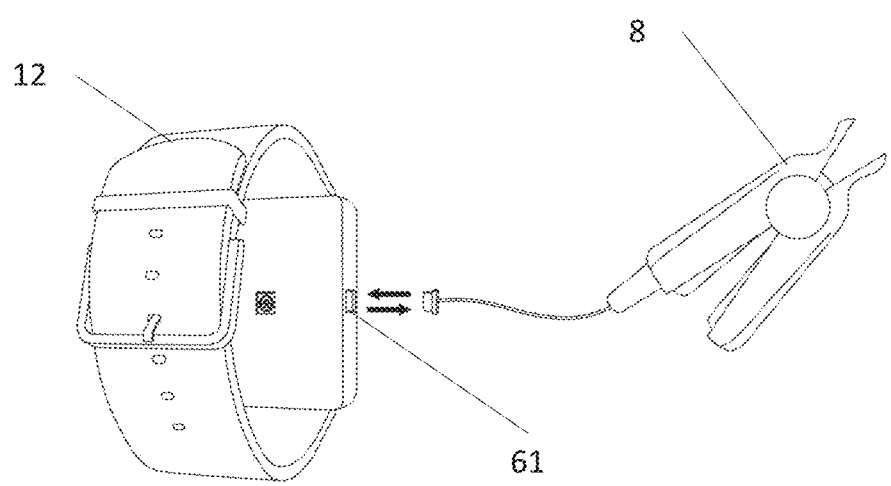
FIG. 84B is a schematic diagram of the optical sensing device connected to another sensing device.

With further comprising a communication module 60, the optical sensing device 12 is capable of integrating the information between the optical sensing device 12 and other external devices. As shown in FIG. 83A, the optical sensing device 12 comprises a microprocessor 20, a communication module 60, a memory 40, and a battery 50. The communication module 60 is embodied as a Bluetooth module communicating with an external device. The optical sensing device 12 may send out control signal to control an external device or receive the signals acquired from an external device. For example, the external device may be an optical sensing accessory 11 (FIG. 84A) so that the optical signals obtained from the optical sensing accessory 11 may be integrated with other health information. Also, the external device may be other accessory sensor devices (FIG. 84B), so that the optical sensing device 12 provides more compatibility for various applications.

The wearable optical sensing device 12 may also connect to the other optical sensing device 12 to deliver the physiological information for further information management. In at least one example, the other computing device may be a handheld optical sensing device 12 or a smart mobile device (for example, iPhone, Android phone, phablet, or tablets), so that the optical sensing device 12 may have lower power consumption, lower hardware requirement, and better compatibility.

Figure 85A:
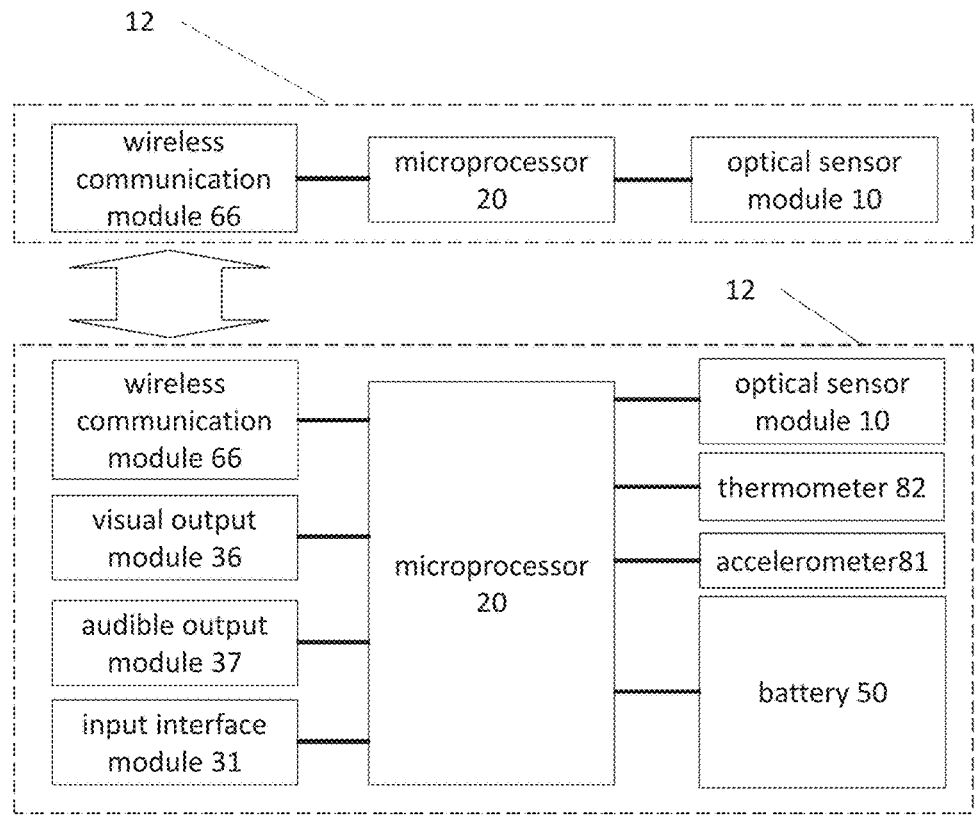
FIG. 85A is a block diagram of a wireless optical sensing device connected to another wireless optical sensing device.
Figure 85B:
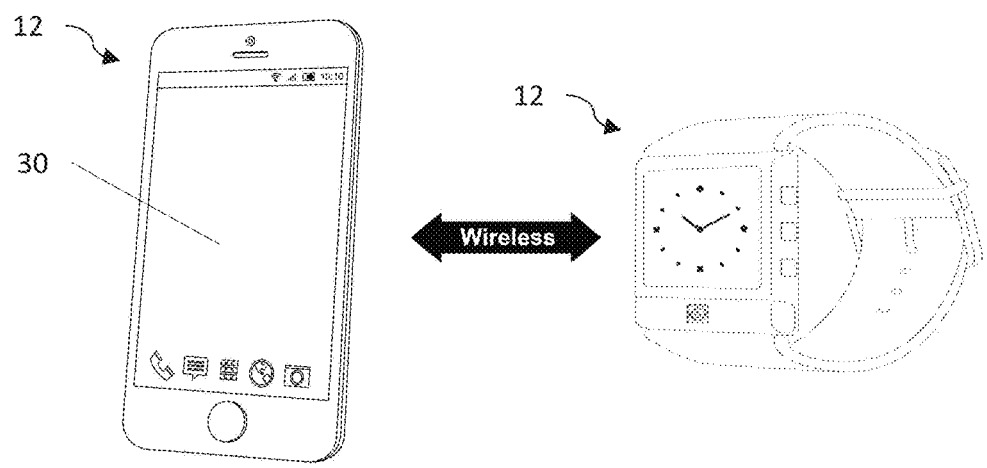
FIG. 85B is a schematic diagram of the wireless optical sensing device connected to another wireless optical sensing device.

In one example as shown in FIG. 85A, an optical sensing device 12 connected to the other optical sensing device 12. One of the optical sensing device has basic electronic modules, including an optical sensor module 10, a microprocessor 20, and a wireless communication module 66, to connect with the other optical sensing device with more functional electronic modules. In FIG. 85B, one of the optical sensing device is a wearable optical sensing watch and the other is an optical sensing smart phone.

Figure 86A:
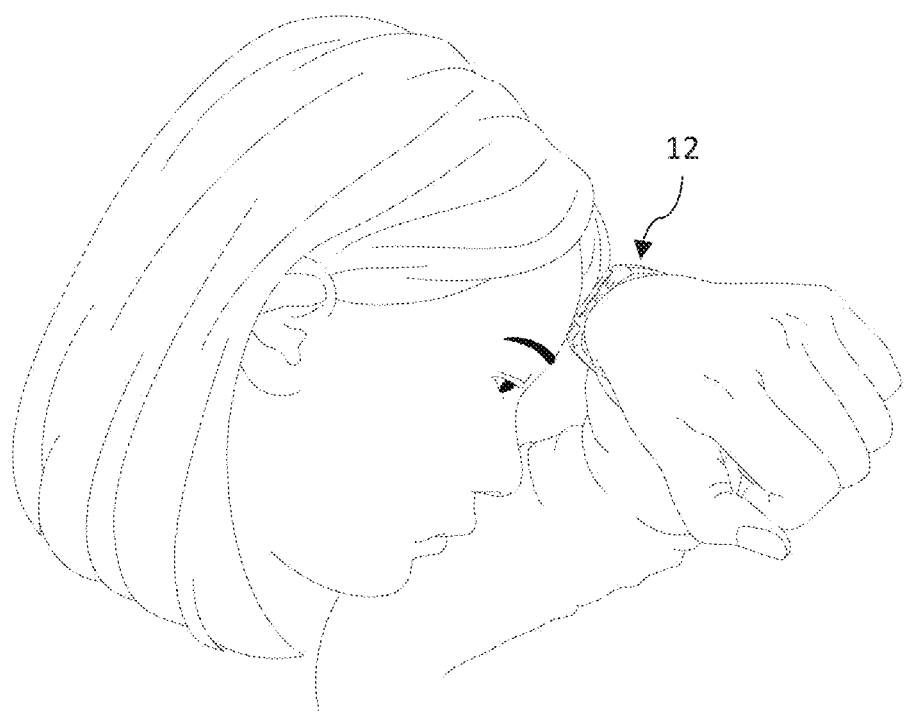
FIGS. 86A and 86B are the schematic diagrams of an application scenario of using an optical sensing device to achieve multi-site measurement.
Figure 86B:
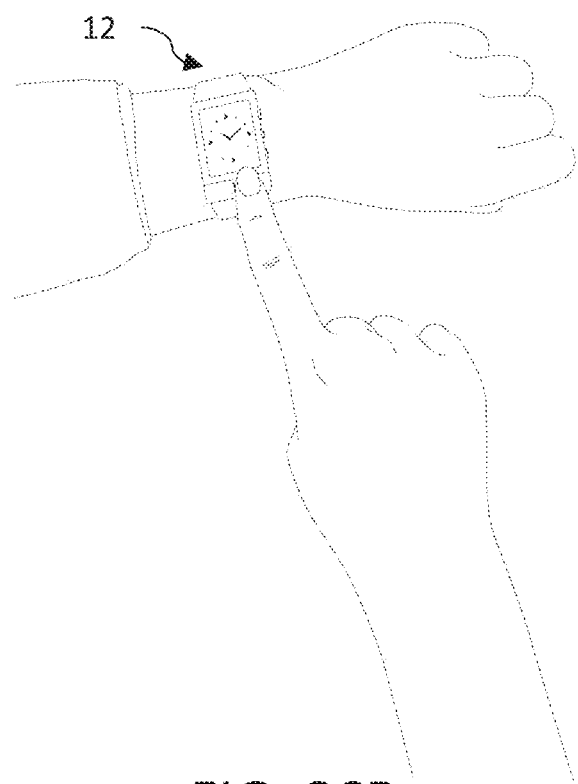

Multi-site measurement is applicable since the wearable optical sensing device improves measurement accuracy and user compliance to record their physiological condition with the aid of the present technology. With the advance performance of the reflective optical sensor module 10, measurement of multiple body regions brings extra useful physiological information. Here, blood oxygenation is illustrated to exploit the utility, while other optical signals from multiple body regions may have further applications. The physiological parameters from multiple body regions demonstrates the regional difference of a physiological parameter among the body parts. For example, the blood oxygenation may vary from forehead and wrist. Also, the phase difference demonstrates the conveyance of a physiological parameter between any two body regions. For example, the pulse wave velocity can be calculated from the pulse phase difference. In addition, continuous multiple body region monitoring may provide a temporal-anatomical distribution of the physiological information. The example in FIGS. 86A and 86B shows the optical sensing device 12. The optical sensing device 12 may be applied to measure forehead and wrist (FIG. 86A), or a wrist and a finger of the contralateral hand (FIG. 86B). Multiple optical measurements may also be acquired through the optical sensing accessory 11 with multiple probes as shown in FIG. 81C. In addition, the multiple optical measurements may be achieved under the integration of multiple optical sensing accessory 11.

In one example, the optical sensing device 12 comprises a bi-directional optical sensor module 5. The optical sensing device 12 may be a wearable watch shown in FIG. 87A-D. In FIG. 87A, the housing of the optical sensing device 12 have one opening on the internal side of the annular housing, and in FIG. 87B, the other opening on the external side of the annular housing. The openings are configured to expose the contact surfaces of the bi-directional optical sensor module 5, so that the light emitted from the light source 110 may be collected by the photodetectors 120 facing different directions. In FIG. 87C, the perspective view from the lateral side shows that the bi-directional sensor module 5 have one contact surface facing toward the external side of the housing and the other contact surface facing toward the internal side of the housing. In FIG. 87D, an enlarged view shows a bi-directional sensor module 5 located in the wearable housing. The bi-directional sensor module 5 is located in the transparent opening 153 of the housing. The transparent opening 153 may further have a cover 150 and the cover may be configured with microstructure, curvature lens, or thin film on the surfaces of the cover, or any combinations as mentioned.

The optical sensing device 12 may comprise an optical sensor module 10, an ARM core microprocessor, a flash memory, a lithium battery, and further comprises other sensor modules, or a GPS receiver module 70, so the other associated information may be stored and processed concomitantly with the physiological information. For example, body temperature may be acquired by an electrical thermometer 82, or electrocardiogram (ECG) by ECG leads. The optical sensing device 12 may store both blood oxygen saturation level and ECG information and further compute the pulse transit time (PTT) as blood pressure. Furthermore, motion information may be acquired by an accelerometer 81 to evaluate the exercise status and applied for sport medicine. With the integrated GPS receiver module 70, the optical sensing device 12 can record the user's physiological information including body temperature, ECG, blood oxygenation, and blood pressure in a time series accompanying the correlated geographic location and exercise status. For example, geographic information obtained by a GPS receiver 70 may be stored with physiological information for geo-medicine applications.

With the present technology, personal health information management may bring great benefits to the user in various applications. For example, the optical sensing device 12 may further comprises a communication module 60 in order to connect to Internet and deliver the information to a cloud server to commit big data collection and analysis. Moreover, the optical sensing device 12 may make an alert to the user or other people around when the optical sensing device 12 sensing abnormal physiological conditions. In emergency situations, the optical sensing device 12 may make a phone call or send out an instant message to inform a concerned authority, such as a hospital or an emergency department, to ask an immediate action. By the present technology, the optical sensing device 12 can realize the point of care (POC) service with comprehensive information. Personal, portable, long-term, and continuous health monitoring can be achieved.

In general, a multi-site sensing device is the integration of multiple optical sensor modules with other electronic modules in a housing. Other electronic modules are configured to assist the optical sensor modules in transmitting, digitizing, processing, or storing the optical signals and to combine the optical signals with other concomitant information; meanwhile, the housing keeps all the electronic modules from external damage and provides a human interface for mobile use. The integration facilitates acquisition of the optical signals and transformation of the acquired optical signals into meaningful information. Specifically, within the range of optical window, incident light can travel in a depth of a biological tissue, and therefore, the information underneath the surface of the biological tissue can be extracted by the reflected light. By studying the spectrum of specific wavelengths, people may further obtain the computed biochemical or physiological parameters. The analysis of optical properties of a biological sample, in vivo, ex vivo, or in vitro, may be accomplished through the operation of the multi-site sensing device. Accordingly, the acquired optical signals are more accessible and applicable with the present technology of the multi-site sensing device.

The multi-site measurement may be acquired by a multi-site optical sensing accessory 15, a multi-site optical sensing device 16, or a multi-site optical sensing system 17. The optical sensing accessory 15, an optical sensing device 16, or an optical sensing system 17 comprises at least two reflective optical sensor modules 109. The reflective optical sensor module 109 is configured to emit light and to measure the reflected light from an object surface. The reflective optical sensor module may be the optical sensor module 10, the multi-directional optical sensor module 5, or the dual sensor module 6. The reflective optical sensor module 109 may also be a sensor module comprising at least the light source 110 and the photodetector 120.

Figure 88:
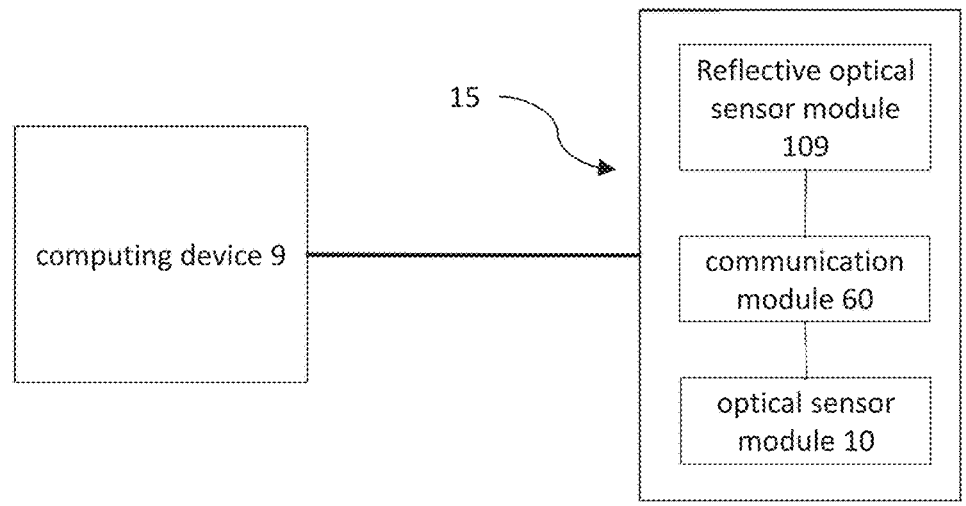
FIG. 88 is a block diagram of a multi-site optical sensing accessory.
Figure 89:
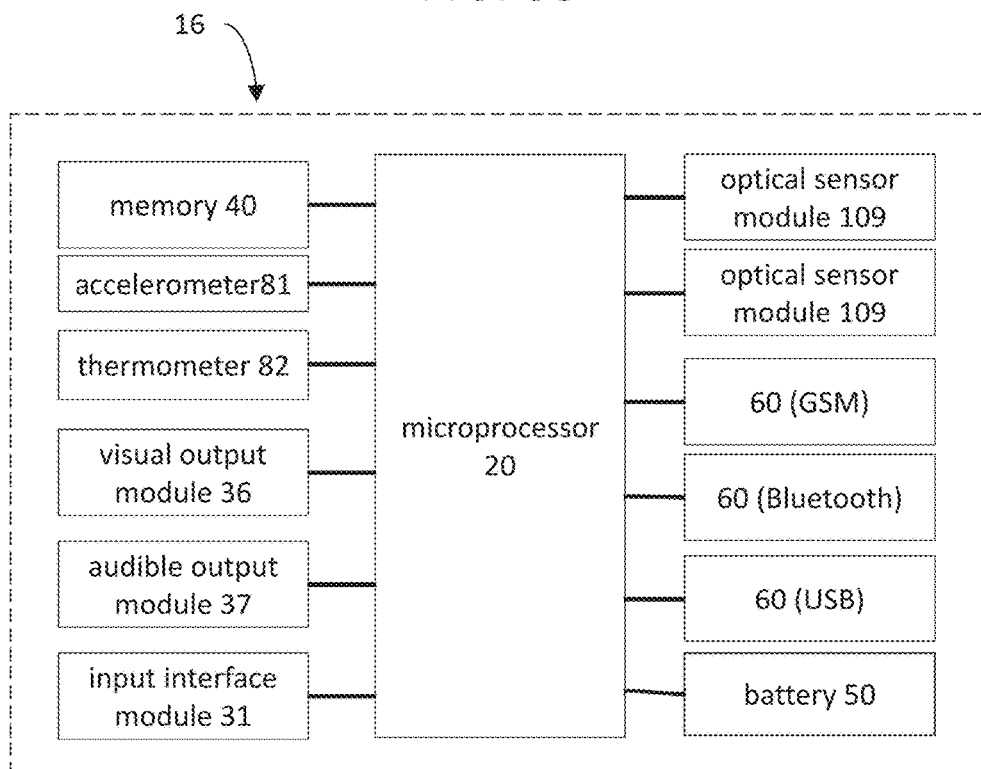
FIG. 89 is a block diagram of a multi-site optical sensing device.
Figure 90:
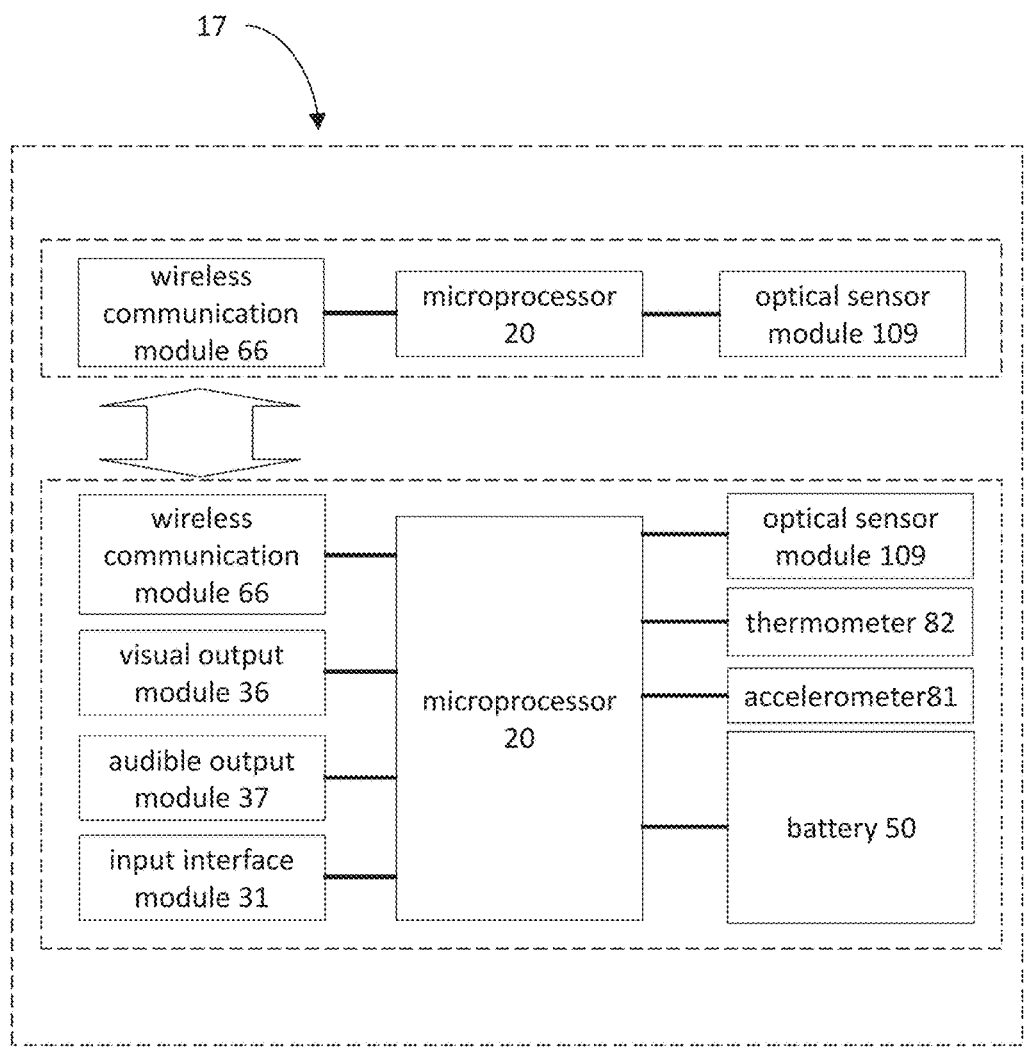
FIG. 90 is a block diagram of a multi-site optical sensing system.

In the present disclosure, the example of a multi-site sensing accessory 15 an optical sensing device 16, and a multi-site sensing system 17 are illustrated in FIG. 88-90.

A multi-site sensing accessory 15 is configured to transmit the optical signals from multiple optical sensor modules to a computing device. A multi-site sensing accessory 15 has a communication module 60 to allow the transmission of acquired signals to a computing device for further signal processing. The multi-site optical sensing accessory 15 comprises plural optical sensor modules, a communication module 60, and a housing. The optical signals are first transduced into electrical signals by the optical sensor modules. Later, the electrical signals may be conveyed to an independent computing device via the communication module 60 (FIG. 88). The optical sensing accessory 15 transmits the electrical signals from multiple optical sensor modules to a computing device through the communication module 60. In at least one example, the multi-site sensing accessory 15 comprises three optical sensor modules, a serial cable plug and a wearable housing presented as a wired patch probe. With connection to an external computing device 9, the optical sensing accessory 15 receives power support and the control signals from the computing device and delivers the converted signals to a computing device via the serial cable. In the case of a wireless communication module 66, a battery 50 is necessary to power the signal transmission by radiofrequency. The coupling external computing device is capable of triggering the operation of the multi-site sensing accessory 15 and managing the received optical signals. The multi-site sensing accessory 15 may have a small volume and be suitable for mobile applications. Most collected physiological information is then transmitted to a mobile device and is further processed.

Also, a multi-site sensing device 16 of the present disclosure is configured to manage the optical signals from an internal optical sensor module or an external sensing devices. Two optical sensor modules 109 are electronically connected to the microprocessor 20, while an external sensing device is connected through a communication module 60. The multi-site optical sensing device 16 comprises at least two optical sensor modules 109, a microprocessor 20, a battery 50, a memory 40, and a housing. The general architecture is shown as FIG. 89, and the other electronic modules may be integrated into the multi-site sensing device 16. The optical signals are obtained by the optical sensor modules. Later, the electrical signals may be directly delivered to and processed by the microprocessor 20.

The optical sensor module may receive and convert the optical signals of a biological tissue to electrical signals and deliver the signals to a microprocessor 20. The multi-site sensing device 16 comprising electronic modules is presented as a multi-site sensing watch (FIGS. 87A-87D). The acquired optical signals are processed by the microprocessor 20, output as physiological parameters, and then stored in the memory 40. For example, the infrared and red light absorbance of applied biological tissue is detected by the optical sensor modules, converted into electrical signals, processed as physiological parameters (for example, oxygen saturation), and stored in a flash memory.

In FIG. 90, the optical sensing system 17 may comprise an optical sensing device with a reflective optical sensor module 109 and an optical sensing accessory with a reflective optical sensor module. The optical sensing device comprises an optical sensor module 109, a microprocessor 20, a battery 50, a memory 40, a communication module 60 and a housing, and the optical sensor module comprises an optical sensor module 109, a communication module 60 and a housing. The communication module 60 may be a wireless communication module 66 which is, for example, a Bluetooth module communicating within the optical sensing system 17. The optical sensing device may send out control signal to control or receive the signals acquired from an optical sensing accessory.

Multi-site measurement is applicable since the multi-site sensing device improves measurement accuracy and user compliance to record their physiological condition with the aid of the present technology. With the advance performance of the multi-site sensing device, measurement of multiple body regions brings extra useful physiological information. Here, blood oxygenation is illustrated to exploit the utility, while other optical signals from multiple body regions may have further applications. First, the physiological parameters from multiple body regions demonstrates the regional difference of a physiological parameter among the body parts. For example, the blood oxygenation may vary from forehead and wrist. Second, the phase difference demonstrates the conveyance of a physiological parameter between any two body regions. For example, the pulse wave velocity can be calculated from the pulse phase difference. Third, continuous multiple body region monitoring may provide a temporal-anatomical distribution of the physiological information.

The optical sensor module is used for the measurement of overall optical reflectance of an object surface. The acquired optical signals may be computed as useful information, especially physiological information, such as the blood oxygen saturation level, which is based on the light absorption rate of particular wavelengths. Further physiological information may be derived from the acquired optical information at multiple parts of human body. For example, the blood oxygen saturation levels may be compared between contralateral sides of extremities, which may indicate regional hypoxia, between upper and lower extremities, for example, the Ankle Brachial Pressure Index indicating the condition of peripheral arteries, or between any two distinct parts of human body.

The embodiments shown and described above are only examples. Many details are often found in the art such as the other features. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, including in matters of shape and arrangement of the parts within the principles of the present disclosure up to, and including the full extent established by the broad general meaning of the terms used in the claims. It will therefore be appreciated that the embodiments described above may be modified within the scope of the claims.

The invention claimed is:

1. A multi-directional optical sensor module comprising:
   a substrate;
   a light source disposed on the substrate;
   a first encapsulant;
   at least two photodetectors disposed on the substrate;
   at least two second encapsulants adjacent to the light source;
   wherein the at least two photodetectors comprise at least a first photodetector and a second photodetector, the light source comprises at least a first side and a second side, the first photodetector is on the first side of the light source and the second photodetector is on the second side of the light source, the first side is a different side from the second side, each of the at least two second encapsulants is formed over a corresponding one of the at least two photodetectors, and the first encapsulant is formed over the light source and the at least two second encapsulants.

2. The multi-directional optical sensor module of claim 1, further comprising a first coating disposed on a top surface of the first encapsulant.

3. The multi-directional optical sensor module of claim 1, further comprising a second coating disposed on a top surface of each of the at least two second encapsulants.

4. The multi-directional optical sensor module of claim 1, wherein the at least two second encapsulants are substantially prismatic or quadrispherical.

5. The multi-directional optical sensor module of claim 1, wherein a top surface of the first encapsulant is composed by at least two intersected planes.

6. The multi-directional optical sensor module of claim 5, wherein the top surface of the first encapsulant is composed by at least two intersected curved planes.

7. The multi-directional optical sensor module of claim 1, wherein the first encapsulant comprises a refractive index $n1$, one of the at least two second encapsulants comprises a refractive index $n2$, and $n1$ is different from $n2$.

8. The multi-directional optical sensor module of claim 1, further comprising at least two contact surfaces, wherein the at least two contact surfaces are side surfaces of the first encapsulant and the at least two second encapsulants, the side surfaces are substantially perpendicular to the substrate and opposite to the light source, and at least a part of the at least two contact surfaces is a microstructure.

9. The multi-directional optical sensor module of claim 1, further comprising at least one of an analogue front end, a microcontroller, an operational amplifier, and a light source driver.

10. A multi-directional optical sensing accessory for detecting optical properties comprising:
- at least one optical sensor module of claim 1;
- a communication module electrically connected to the optical sensor module; and
- a housing containing the optical sensor module, the communication module.

11. A multi-directional optical sensing device for detecting optical properties comprising:
- at least one optical sensor module of claim 1;
- a microprocessor electrically connected to the optical sensor module;
- a memory electrically connected to the optical sensor module and the microprocessor;
- a power supply electrically connected to the optical sensor module and the memory; and
- a housing containing the optical sensor module, the memory and the power supply.

12. The multi-directional optical sensor module of claim 2, wherein the first coating confines light emitted by the light source toward a predetermined direction, and the first coating is a reflective material or a metal film.

13. The multi-directional optical sensor module of claim 3, wherein the second coating blocks light emitted from the light source directly to the at least two photodetectors, and the second coating is a reflective material or a metal film.

14. The multi-directional optical sensor module of claim 5, wherein the top surface of the first encapsulant is composed by at least two intersected inclined planes.

15. The multi-directional optical sensor module of claim 7, wherein the refractive index $n2$ is greater than the refractive index $n1$.

16. The multi-directional optical sensor module of claim 8, wherein the at least two contact surfaces comprise a first contact surface and a second contact surface, the first contact surface is a side surface of the first encapsulant for light emitted from the light source, and the second contact surface is a side surface of the at least two second encapsulants for light reflected to the at least two photodetectors.

17. The multi-directional optical sensor module of claim 8, wherein the microstructure is transparent and is configured for concentrating light toward a predetermined direction.

18. The multi-directional optical sensor module of claim 1, wherein a top surface of the first encapsulant has a predetermined tilting angle or a predetermined curvature.

19. The multi-directional optical sensor module of claim 1, wherein a top surface of the at least two second encapsulants has a predetermined tilting angle or a predetermined curvature.

* * * * *